US011004918B2

(12) United States Patent
Kim et al.

(10) Patent No.: US 11,004,918 B2
(45) Date of Patent: May 11, 2021

(54) ELECTRONIC APPARATUS

(71) Applicant: Samsung Display Co., Ltd., Yongin-si (KR)

(72) Inventors: Yohan Kim, Yongin-si (KR); Yisu Kim, Yongin-si (KR); Wonmin Yun, Yongin-si (KR); Byoungduk Lee, Yongin-si (KR); Yoonhyeung Cho, Yongin-si (KR)

(73) Assignee: Samsung Display Co., Ltd., Yongin-si (KR)

(*) Notice: Subject to any disclaimer, the term of this patent is extended or adjusted under 35 U.S.C. 154(b) by 0 days.

(21) Appl. No.: 16/296,074

(22) Filed: Mar. 7, 2019

(65) Prior Publication Data

US 2019/0280064 A1 Sep. 12, 2019

(30) Foreign Application Priority Data

Mar. 9, 2018 (KR) ........................ 10-2018-0028294
Apr. 6, 2018 (KR) ........................ 10-2018-0040600

(51) Int. Cl.
*H01L 27/32* (2006.01)
*C07C 39/06* (2006.01)
(Continued)

(52) U.S. Cl.
CPC .......... *H01L 27/3246* (2013.01); *C07C 39/06* (2013.01); *C07C 39/38* (2013.01); *C07C 49/115* (2013.01); *C07C 49/303* (2013.01); *C07C 49/323* (2013.01); *C07D 249/20* (2013.01); *C07D 311/86* (2013.01); *C08L 33/10* (2013.01);
(Continued)

(58) Field of Classification Search
CPC . H01L 27/3246; H01L 51/5253; C07C 39/06; C07C 49/115; C07C 49/303; C07C 49/323; C07D 249/20; C07D 311/86; C08L 33/10
See application file for complete search history.

(56) References Cited

U.S. PATENT DOCUMENTS 8,941,003 B2 1/2015 Mandokoro et al.
9,818,972 B2 11/2017 Choi et al.
(Continued)

FOREIGN PATENT DOCUMENTS

KR 10-2012-0125617 A 11/2012
KR 10-2014-0034600 A 3/2014
(Continued)

OTHER PUBLICATIONS

Extended European Search Report for corresponding European Patent Application No. 19161310.8, dated Jul. 11, 2019, 10 pages.

*Primary Examiner* — Anthony Ho

(74) *Attorney, Agent, or Firm* — Lewis Roca Rothgerber Christie LLP

(57) ABSTRACT

Provided is an electronic apparatus including: a substrate; a pixel defined layer defining a plurality of pixel areas and a plurality of non-pixel areas on the substrate; a plurality of light-emitting diodes arranged on the plurality of the pixel areas; and a thin film encapsulation portion including an
(Continued)

organic film and sealing the pixel defined layer, or the plurality of the light-emitting diodes and the pixel defined layer, wherein the organic film includes a curable material of a composition for forming an organic film, the composition including at least one UV absorber.

19 Claims, 6 Drawing Sheets

(51) Int. Cl.

| | |
|---|---|
| ***C07C 39/38*** | (2006.01) |
| ***C07C 49/115*** | (2006.01) |
| ***C07C 49/303*** | (2006.01) |
| ***C07C 49/323*** | (2006.01) |
| ***C07D 249/20*** | (2006.01) |
| ***C07D 311/86*** | (2006.01) |
| ***C08L 33/10*** | (2006.01) |
| ***H01L 51/00*** | (2006.01) |
| ***H01L 51/50*** | (2006.01) |
| ***H01L 51/52*** | (2006.01) |

(52) U.S. Cl.
CPC ...... *H01L 27/3211* (2013.01); *H01L 51/0085* (2013.01); *H01L 51/0087* (2013.01); *H01L 51/0089* (2013.01); *H01L 51/502* (2013.01); *H01L 51/5016* (2013.01); *H01L 51/5253* (2013.01); *H01L 51/5256* (2013.01); *C08L 2203/16* (2013.01)

(56) References Cited

U.S. PATENT DOCUMENTS

| | | | |
|---|---|---|---|
| 9,837,633 | B2 | 12/2017 | Lee et al. |
| 10,381,596 | B2 | 8/2019 | Jeong et al. |
| 2015/0357570 | A1 | 12/2015 | Lee et al. |
| 2016/0329526 | A1 | 11/2016 | Pudleiner et al. |
| 2017/0025485 | A1 | 1/2017 | Kim et al. |
| 2017/0186999 | A1 | 6/2017 | Lee et al. |
| 2017/0244058 | A1 | 8/2017 | Liu et al. |

FOREIGN PATENT DOCUMENTS

| | | | |
|---|---|---|---|
| KR | 10-2015-0008873 | A | 1/2015 |
| KR | 10-2016-0150260 | A | 12/2016 |
| KR | 10-2017-0132639 | A | 12/2017 |
| KR | 10-2019-0017102 | A | 2/2019 |
| WO | WO 2015/110426 | A1 | 7/2015 |

IMAGE OF LIGHTENED APPARATUS BEFORE LIGHT EXPOSURE OF EXAMPLE 1-2

IMAGE OF LIGHTENED APPARATUS BEFORE LIGHT EXPOSURE OF COMPARATIVE EXAMPLE 1-2

IMAGE OF LIGHTENED APPARATUS AFTER LIGHT EXPOSURE OF EXAMPLE 1-2

IMAGE OF LIGHTENED APPARATUS AFTER LIGHT EXPOSURE OF COMPARATIVE EXAMPLE 1-2

EXAMPLE 2-1

COMPARATIVE
EXAMPLE 2-2

ELECTRONIC APPARATUS

CROSS-REFERENCE TO RELATED APPLICATIONS

This application claims priority to and the benefit of Korean Patent Application Nos. 10-2018-0028294, filed on Mar. 9, 2018, and 10-2018-0040600, filed on Apr. 6, 2018, in the Korean Intellectual Property Office, the entire content of each of which is incorporated herein by reference.

BACKGROUND

1. Field

One or more embodiments relate to an electronic apparatus including an ultraviolet (UV) absorber and a pixel defined layer.

2. Description of the Related Art

Light-emitting diodes convert electrical energy into light energy. An electronic apparatus including such a light-emitting diode includes a hole injection electrode, an electron injection electrode, and an emission layer between the hole injection and the electron injection electrode. Such an electronic apparatus may include a substrate and a pixel defined layer which defines a pixel area and a non-pixel area on the substrate, wherein the pixel area includes a light-emitting diode.

As outdoor use of information appliances, such as an electronic apparatus including a light-emitting diode, increases, the time of exposure of an electronic apparatus including a light-emitting diode to sunlight also gradually increases. In addition, in the process of manufacturing a light-emitting diode, irradiating ultraviolet rays is used in many cases. As such, when external ultraviolet light freely reaches regions inside an electronic apparatus, for example, a light-emitting diode and a pixel defined layer, outgas from a pixel defined layer constituting of an organic insulating material to a light-emitting diode located in an adjacent pixel area is caused, resulting in deterioration of the light-emitting diode.

Therefore, studies are being conducted to prevent or reducing outgassing of a pixel defined layer upon ultraviolet transmission into an electronic apparatus.

SUMMARY

An electronic apparatus has a problem of deterioration of a light-emitting diode, due to outgassing of a pixel defined layer an organic layer including an emission layer, when ultraviolet light or the like enters from the outside of the electronic apparatus or enters and penetrates the electronic apparatus during the manufacturing process of the electronic apparatus.

An example of an organic light-emitting device, which is one type (or kind) of light-emitting diode, is a self-emission device that has excellent characteristics in terms of wide viewing angles, high contrast ratios, short response time, luminance, driving voltage, and response speed, compared to other devices in the art. For example, in an organic light-emitting display apparatus, which is one type (or kind) of electronic apparatus including the organic light-emitting device, holes provided from a hole injection electrode, and electrons provided from an electron injection electrode recombine in an organic emission layer to produce excitons.

These excitons transit (e.g., transition or relax) from an excited state to a ground state, thereby generating light.

Such an organic light-emitting display apparatus, which is a self-emission display device, does not require a separate light source, resulting in being driven at a low voltage and configured as a thin and lightweight device. Due to excellent characteristics in terms of viewing angles, high contrast ratios, and short response times, the organic light-emitting display apparatus has been expanded in application range from a personal portable device, such as an MP3 player or a cellular phone, to a television (TV).

Meanwhile, as outdoor use of information appliances, such as an electronic apparatus including an organic light-emitting device, increases, time for exposure of such an electronic apparatus including the organic light-emitting device to sunlight also gradually increases. In addition, in the process of manufacturing an organic light-emitting device, irradiating ultraviolet rays is used in many cases. As such, when external ultraviolet light freely reaches regions inside the organic light-emitting device, for example, an emission layer including an organic material may be seriously damaged.

The present disclosure is directed to reducing the above-described deterioration, and to provide an electronic apparatus capable of reducing an amount of ultraviolet light transmitted into an electronic apparatus. However, these problems are illustrative, and thus the scope of the present disclosure is not limited thereto.

Additional aspects of embodiments will be set forth in part in the description which follows and, in part, will be apparent from the description, or may be learned by practice of the presented embodiments.

According to one or more embodiments, an electronic apparatus includes:

a substrate;

a pixel defined layer defining a plurality of pixel areas and a plurality of non-pixel areas on the substrate;

a plurality of light-emitting diodes arranged on the plurality of the pixel areas;

and a thin film encapsulation portion including an organic film and sealing the plurality of the light-emitting diodes and the pixel defined layer at the same (e.g., substantially the same) time, wherein the organic film includes a cured product of a composition for forming an organic film, the composition including a curable material and an ultraviolet (UV) absorber, wherein the curable material is a (meth)acrylate compound.

According to one or more embodiments, an electronic apparatus includes:

a substrate;

an organic light-emitting device disposed on the substrate and including an emission layer; and a thin film encapsulation portion sealing the organic light-emitting device and including at least one organic film, wherein the emission layer includes an organometallic compound, and the organic film includes a cured product of a composition for forming an organic film, the composition including a curable material and an ultraviolet (UV) absorber, wherein the curable material is a (meth)acrylate compound.

According to one or more embodiments, an electronic apparatus includes:

a substrate;

a pixel defined layer defining a plurality of pixel areas and a plurality of non-pixel areas on the substrate;

a plurality of light-emitting diodes arranged on the plurality of the pixel areas; and a thin film encapsulation portion including an organic film and sealing the pixel defined layer or both the plurality of the light-emitting diodes and the pixel defined layer;

wherein the organic film includes a cured product of a composition for forming an organic film, the composition comprising at least one UV absorber.

BRIEF DESCRIPTION OF THE DRAWINGS

These and/or other aspects of embodiments will become apparent and more readily appreciated from the following description of the embodiments, taken in conjunction with the accompanying drawings in which.

DETAILED DESCRIPTION

Figure 1:
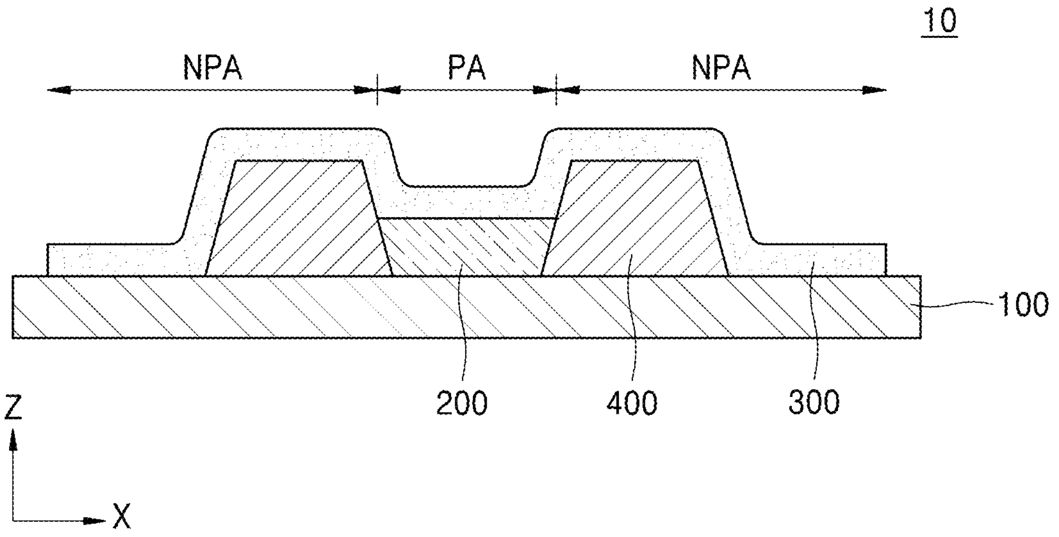
FIG. 1 is a schematic cross-sectional view of a structure of an electronic apparatus according to an embodiment.

Reference will now be made in more detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of embodiments of the present description. Expressions such as "at least one of," when preceding a list of elements, modify the entire list of elements and do not modify the individual elements of the list.

As the present disclosure allows for various changes and numerous embodiments, exemplary embodiments will be illustrated in the drawings and described in detail in the written description. The effects and features of embodiments of the present disclosure and methods of achieving these effects and features will be apparent with reference to Examples described in more detail along with the accompanying drawings. The subject matter of the present disclosure may, however, be embodied in many different forms and should not be construed as limited to the exemplary embodiments set forth herein.

Hereinafter, embodiments will be described in more detail by explaining exemplary embodiments with reference to the accompanying drawings. Like reference numerals in the drawings denote like elements, and redundant descriptions thereof are not repeated herein.

It will be understood that when a layer, film, region, or plate is referred to as being "formed on" another layer, film, region, or plate, it can be "directly" or indirectly formed on the other layer, film, region, or plate. For example, intervening layers, films, regions, or plates may be present. In addition, sizes of components in the drawings may be exaggerated for convenience of explanation. In other words, since sizes and thicknesses of components in the drawings may be arbitrarily illustrated for convenience of explanation, the following embodiments are not limited thereto.

While such terms as "first," "second," etc., may be used to describe various components, such components must not be limited to the above terms. The above terms are used only to distinguish one component from another.

In the following examples, the x-axis, the y-axis and the z-axis are not limited to three axes of the rectangular coordinate system, and may be interpreted in a broader sense. For example, the x-axis, the y-axis, and the z-axis may be perpendicular (e.g., substantially perpendicular) to one another, or may represent different directions that are not perpendicular (e.g., not substantially perpendicular) to one another.

FIG. 1 is a schematic cross-sectional view of a structure of an electronic apparatus according to an embodiment.

Referring to FIG. 1, an electronic apparatus 10 according to an embodiment includes a substrate 100, a light-emitting diode 200, a thin film encapsulation portion 300, and a pixel defined layer 400.

The substrate 100 may be any suitable substrate available in the art for an organic light-emitting display device, and may be an inorganic substrate or an organic substrate, each having excellent mechanical strength, thermal stability, transparency, surface smoothness, ease of handling, and water resistance.

For example, the substrate 100 may be an inorganic substrate made of a transparent glass material containing $SiO_2$ as a main component, but embodiments of the present disclosure are not limited thereto.

For example, the substrate 100 may be an organic substrate having an insulating property. An organic material having an insulating property may be, for example, selected from polyethersulphone (PES), polyacrylate (PAR), polyetherimide (PEI), polyethylene naphthalate (PEN), polyethylene terephthalate (PET), polyphenylene sulfide (PPS), polyallylate, polyimide, polycarbonate (PC), cellulose triacetate (TAC), and cellulose acetate propionate (CAP), but embodiments of the present disclosure are not limited thereto.

The pixel defined layer 400 defining a pixel area (PA) and a non-pixel area (NPA) may be disposed on the substrate 100. In one embodiment, the pixel defined layer 400 may be disposed so as to surround the PA while covering edges of a pixel electrode and exposing a center portion the pixel electrode to the outside.

The pixel defined layer 400 may be formed of any suitable organic insulating material or any suitable inorganic insulating material available in the art. In one embodiment, the pixel defined layer 400 may be formed of a polymer, such as polyimide and/or polyacrylate.

In one embodiment, a light-emitting diode 200 may be disposed over the PA. The light-emitting diode 200 may include a first electrode, an intermediate layer including an emission layer, and a second electrode.

In one embodiment, the light-emitting diode 200 may be an organic light-emitting device.

In one embodiment, a plurality of the light-emitting diodes 200 may be disposed on the substrate 100, so as to be surrounded by the pixel defined layer 400. For example, the pixel defined layer 400 may be provided such that the center portion of the pixel electrode, such as the first electrode, within the PA may be exposed to the outside and the edges of the pixel electrode may be covered by the pixel defined layer 400. Then, a plurality of the light-emitting diodes 200 may be located in a plurality of the center portions exposed to the outside. Accordingly, a plurality of the light-emitting diodes 200 may be insulated from each other.

The first electrode may be formed by, for example, depositing or sputtering a material for forming the first electrode on the substrate 100. When the first electrode is an anode, the material for forming the first electrode may be selected from materials having a high work function to facilitate hole injection.

The first electrode may be a reflective electrode, a semi-transmissive electrode, or a transmissive electrode. When the first electrode is a transmissive electrode, the material for forming the first electrode may be selected from indium tin oxide (ITO), indium zinc oxide (IZO), tin oxide ($SnO_2$), zinc oxide (ZnO), and any combination thereof, but embodiments of the present disclosure are not limited thereto. When the first electrode is a semi-transmissive electrode or a reflective electrode, the material for forming the first electrode may be selected from magnesium (Mg), silver (Ag), aluminum (Al), aluminum-lithium (Al—Li), calcium (Ca), magnesium-indium (Mg—In), magnesium-silver (Mg—Ag), and any combination thereof, but embodiments of the present disclosure are not limited thereto.

The first electrode may have a single-layered structure, or a multi-layered structure including two or more layers. For example, the first electrode may have a three-layered structure of ITO/Ag/ITO, but embodiments of the present disclosure are not limited thereto.

The intermediate layer including the emission layer may be disposed on the first electrode. The emission layer may be referred to the description provided below.

The intermediate layer may further include a hole transport region between the first electrode and the emission layer, and an electron transport region between the emission layer and the second electrode, but embodiments of the present disclosure are not limited thereto.

The second electrode may be disposed on the intermediate layer. The second electrode may be a cathode that is an electron injection electrode, and in this regard, a material for forming the second electrode may be a metal, an alloy, an electrically conductive compound, and any combination thereof.

The second electrode include at least one selected from lithium (Li), silver (Ag), magnesium (Mg), aluminum (Al), aluminum-lithium (Al—Li), calcium (Ca), magnesium-indium (Mg—In), magnesium-silver (Mg—Ag), ITO, and IZO, but embodiments of the present disclosure are not limited thereto. The second electrode may be a transmissive electrode, a semi-transmissive electrode, or a reflective electrode.

The second electrode may have a single-layered structure, or a multi-layered structure including two or more layers.

Then, a thin film encapsulation portion 300 sealing the light-emitting diode 200 and the pixel defined layer 400 at the same (e.g., substantially the same) time and including an organic film may be disposed on the second electrode.

In one embodiment, the organic film may include a cured product of a composition for forming the organic film, the composition including at least one ultraviolet (UV) absorber.

In one embodiment, the UV absorber may include at least one selected from a benzophenone-containing compound, a benzoquinone-containing compound, a anthraquinone-containing compound, a xanthone-containing compound, a benzotriazine-containing compound, a benzotriazinone-containing compound, a benzotriazole-containing compound, a benzoate-containing compound, a cyanoacrylate-containing compound, a triazine-containing compound, an oxanilide-containing compound, a salicylate-containing compound, a pyrene-containing compound, a naphthalene-containing compound, an anthracene-containing compound, and a cathechol-containing compound, each substituted with a hydroxyl group.

The benzophenone-containing compound may be, for example, 2-hydroxybenzophenone, 2,4-dihydroxybenzophenone, 2-hydroxy-4-methoxybenzophenone, 2-hydroxy-4-octylbenzophenone, 4-dodecyloxy-2-hydroxybenzophenone, 4-benzyloxy-2-hydroxybenzophenone, 2,2',4,4'-tetrahydroxybenzophenone, or 2,2'-dihydroxy-4,4'-dimethoxybenzophenone.

The benzoquinone-containing compound may be, for example, 2-hydroxybenzoquinone.

The anthraquinone-containing compound may be, for example, 1-hydroxyanthraquinone, 1,5-hydroxyanthraquinone, or 1,8-hydroxyanthraquinone.

The benzotriazole-containing compound may be, for example, 2-(2-hydroxyphenyl)benzotriazole, 2-(5-methyl-2-hydroxyphenyl)benzotriazole, 2-[2-hydroxy-3,5-bis(α,α-dimethylbenzyl)phenyl]-2H-benzotriazole, 2-(3,5-di-t-butyl-2-hydroxyphenyl)benzotriazole, 2-(3-t-butyl-5-methyl-2-hydroxyphenyl)-5-chlorobenzotriazole, 2-(3,5-di-t-butyl-2-hydroxyphenyl)-5-chlorobenzotriazole, 2-(3,5-di-t-acyl-2-hydroxyphenyl)benzotriazole, or 2-(2'-hydroxy-5'-t-octylphenyl)benzotriazole.

The benzoate-containing compound may be, for example, phenyl 2-hydroxybenzoate or 2,4-di-t-butylphenyl-3',5'-di-t-butyl-4-hydroxybenzoate.

The triazine-containing compound may be, for example, 2-(4,6-diphenyl-1,3,5-triazine-2-yl)phenol, 2-(4,6-diphenyl-1,3,5-triazine-2-yl)-5-(hexyl)oxy-phenol, or 2-[4-[(2-hydroxy-3-dodecyloxypropyl)oxy]-2-hydroxyphenyl]-4,6-bis(2,4-dimethylphenyl)-1,3,5-triazine.

The salicylate-containing compound may be, for example, phenylsalicylate or 4-t-butylphenylsalicylate.

In one embodiment, the UV absorber may include an UV-absorbing compound, and the UV-absorbing compound may include at least one UV-absorbing unit represented by one selected from Formulae 1-1 to 1-4:

Formula 1-1

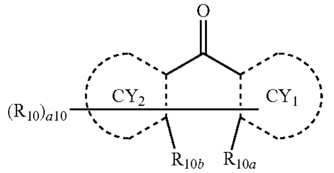

Formula 1-2

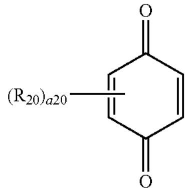

-continued

Formula 1-3

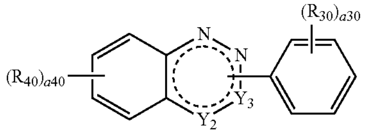

Formula 1-4

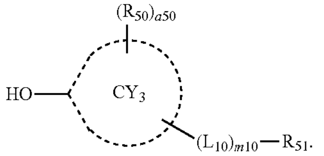

In Formulae 1-1 to 1-4, $CY_1$ to $CY_3$ may each independently be selected from a benzene group, a naphthalene group, an anthracene group, a pyrene group, and a phenanthrene group, $L_{10}$ may be —O—, —S—, S(═O)$_2$—, —C(═O)—, —C(═O)O—, —C(═O)NH—, a $C_1$-$C_{30}$ hydrocarbon group, a $C_5$-$C_{60}$ carbocyclic group, or a $C_2$-$C_{30}$ heterocyclic group, m10 may be an integer of 0 to 5, $L_{10}$ may be a single bond when m10 is 0, $R_{10a}$ and $R_{10b}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —C(═O)($Q_1$), —S(═O)$_2$($Q_1$), and —P(═O)($Q_1$)($Q_2$), $R_{10a}$ and $R_{10b}$ may optionally be linked to form a —$(Y_1)_{k1}$— linking group, $Y_1$ may be —O—, —S—, or —C(═O)—, k1 may be an integer of 1 to 3, at least one of $Y_2$ and $Y_3$ may be N, and the other one may be a single bond, a double bond, or —C(═O)—, $R_{10}$, $R_{20}$, $R_{30}$, $R_{40}$, $R_{50}$, and $R_{51}$ may each independently be selected form hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, —$N(Q_1)(Q_2)$, —$B(Q_1)(Q_2)$, —C(═O)($Q_1$), —S(═O)$_2$($Q_1$), and —P(═O)($Q_1$)($Q_2$), a10 may be an integer of 1 to 8, a20 and a40 may each independently be an integer of 1 to 4, a30 may be an integer of 1 to 5, a50 may be an integer of 1 to 10, at least one of $R_{10}$(s) in the number of a10 may be a hydroxyl group, at least one of $R_{20}$(s) in the number of a20 may be a hydroxyl group, and at least one of $R_{30}$(s) in the number of a30 may be a hydroxyl group.

In one embodiment, the UV-absorbing compound may be represented by Formulae 1-1 to 1-5:

$$A_1\text{-}(X_1)_{n1}\text{-}A_2. \quad \text{Formula 1-5}$$

In Formula 1-5, $A_1$ and $A_2$ may each independently be a monovalent group derived from the UV-absorbing unit, $X_1$ may be a $C_2$-$C_{60}$ hydrocarbon group, and n1 may be an integer of 1 to 5.

For example, the UV-absorbing unit may be represented by one selected from Formulae 2-1 to 2-11, but embodiments of the present disclosure are not limited thereto:

2-1

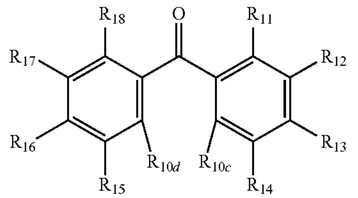

2-2

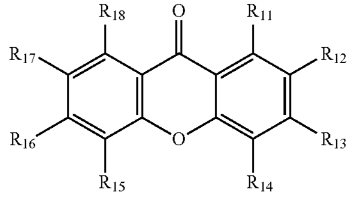

2-3

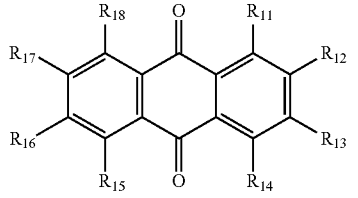

2-4

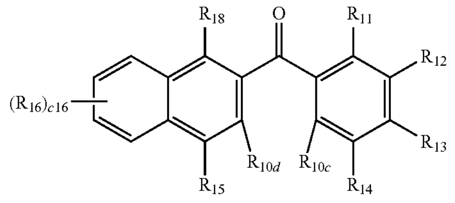

-continued 2-5

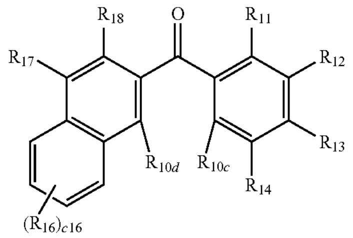

2-6

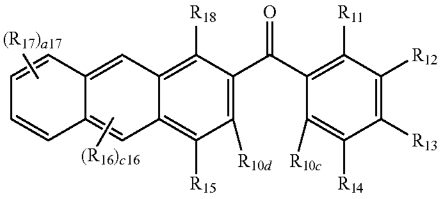

2-7

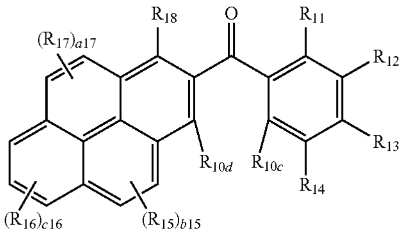

2-8

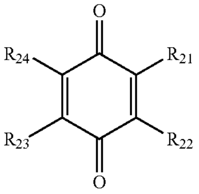

2-9

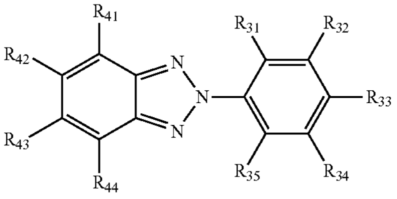

2-10

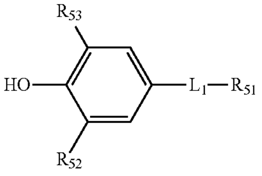

2-11

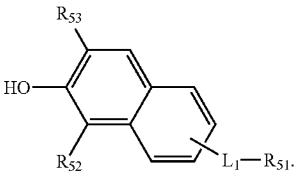

In Formulae 2-1 to 2-11, $L_1$ is defined the same as described above in connection with $L_{10}$, $R_{10c}$, $R_{10d}$, and $R_{11}$ to $R_{18}$ may respectively be defined the same as described above in connection with $R_{10}$, a16 may be 1 or 2, a17 may be 1, 2, 3, or 4, b15 may be 1 or 2, b16 may be 1, 2, or 3, b17 may be 1 or 2, c16 may be 1, 2, 3, or 4, $R_{21}$ to $R_{24}$ may respectively be defined the same as described above in connection with $R_{20}$, $R_{31}$ to $R_{35}$ may respectively be defined the same as described above in connection with $R_{30}$, $R_{41}$ to $R_{44}$ may respectively be defined the same as described above in connection with $R_{40}$, $R_{51}$ to $R_{53}$ are respectively defined the same as described above in connection with $R_{50}$, at least one selected from $R_{11}$ to $R_{18}$, at least one selected from $R_{21}$ to $R_{24}$, and at least one selected from $R_{31}$ to $R_{35}$ may each independently a hydroxyl group, and

* indicates a binding site to a neighboring atom.

In one embodiment, the UV absorber may include a first UV-absorbing compound and a second UV-absorbing compound, wherein the first UV-absorbing compound and the second UV-absorbing compound may each independently be selected from:

a benzophenone-containing compound, a benzoquinone-containing compound, a anthraquinone-containing compound, a xanthone-containing compound, a benzotriazine-containing compound, a benzotriazinone-containing compound, a benzotriazole-containing compound, a benzoate-containing compound, a cyanoacrylate-containing compound, a triazine-containing compound, an oxanilide-containing compound, a salicylate-containing compound, a pyrene-containing compound, a naphthalene-containing compound, and an anthracene-containing compound, and a cathechol-containing compound, each substituted with a hydroxyl group, and a wavelength range of light absorbed by the first UV-absorbing compound may be different from that of light absorbed by the second UV-absorbing compound.

In one embodiment, the UV-absorbing unit may be represented by one selected from Formulae 3-1 to 3-9:

3-1

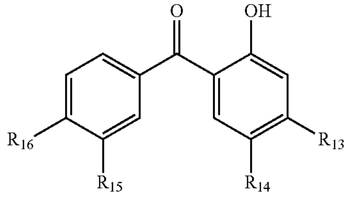

3-2

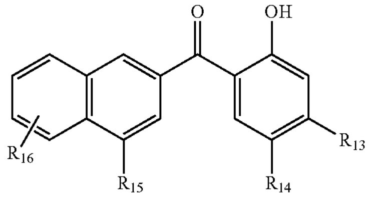

3-3

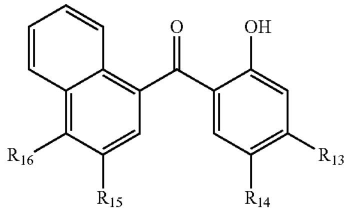

-continued 3-4

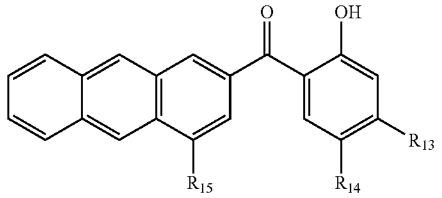

3-5

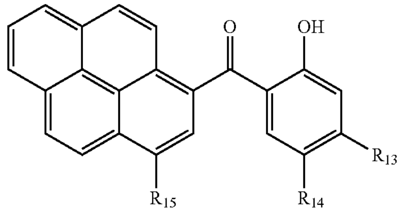

3-6

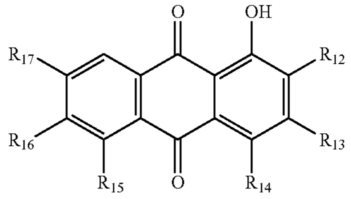

3-7

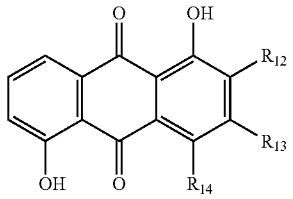

3-8

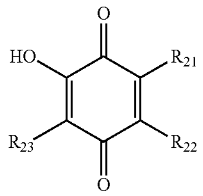

3-9

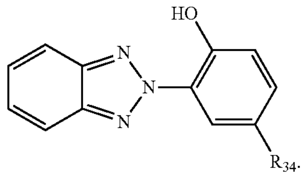

In Formulae 3-1 to 3-9, $R_{13}$, to $R_{17}$ may respectively be defined the same as described above in connection with $R_{10}$, $R_{21}$ to $R_{23}$ may respectively be defined the same as described above in connection with $R_{20}$, $R_{34}$ may be defined the same as described above in connection with $R_{30}$, and

* indicates a binding site to a neighboring atom.

In one embodiment, a wavelength range of light absorbed by the first UV-absorbing compound may be different from that of light absorbed by the second UV-absorbing compound.

In one embodiment, the UV absorber may absorb light having a wavelength between 280 nm and 430 nm. In one or more embodiments, the UV absorber may absorb light having a wavelength between about 340 nm and about 430 nm.

The UV absorber may absorb UV light and prevent the UV light from penetrating the pixel defined layer 400 (or reduce a likelihood or amount of UV light penetrating the pixel defined layer 400). Thus, the electronic apparatus 10 including the UV absorber in the thin film encapsulation portion 300 may be able to prevent or reduce deterioration of the light-emitting diode 200, which is caused by outgassing of the pixel defined layer 400 upon the UV light, and damage of an insulating film or the emission layer including an organic material.

In one embodiment, an amount of the UV absorber may be in a range of about 0.1 parts to about 20 parts by weight, for example, about 0.5 parts to about 5 parts by weight, based on 100 parts by weight of the composition for forming the organic film. By controlling the amount of the UV absorber in the organic film, the maximum absorption wavelength of the organic film may be finely adjusted, and accordingly, the UV absorption spectrum of the organic film may be also controlled. When the amount of the UV absorber is less than about 0.1 parts by weight, the thin film encapsulation portion 300 may fail to sufficiently secure light stability. When the amount of the UV absorber is greater than 20 parts by weight, the transmittance in a visible light area of the thin film encapsulation portion 300 may be inhibited while the light emission efficiently of the organic light-emitting device (e.g., a blue organic light-emitting device having a maximum wavelength between 430 nm and 460 nm) may be inhibited.

When the amount of the UV absorber is in the range above, excellent UV blocking effect may be achieved. For example, when the electronic apparatus 10 includes an organic light-emitting device, the thin film encapsulation portion 300 may have high light stability due to the UV absorber so that the thin film encapsulation portion 300 may be able to effectively protect an organic light-emitting device, for example, an organometallic compound in the emission layer, from UV light.

In one embodiment, the composition for forming the organic film may include the UV absorber and a curable material. The curable material may include at least one selected from an acryl-based material, a methacryl-based material, an acrylate-based material, a methacrylate-based material, a vinyl-based material, an epoxy-based material, a urethane-based material, and a cellulose-based material.

For example, a cured product of the composition including the curable material and the UV absorber for forming the organic film may include a (meth)acrylate resin derived from the (meth)acrylate compound, and may further include at least one selected from an isoprene-based resin, a vinyl-based resin, an epoxy-based resin, an urethane-based resin, a cellulose-based resin, a perylene-based resin, an imide-based resin, and a silicon-based resin that are derived from at least one selected from the vinyl-based compound, the epoxy-based compound, the urethane-based compound, and the cellulose-based compound In one embodiment, the organic film may have a structure in which the UV absorber is dispersed in the cured product of the curable material. Here, the UV absorber may be simply dispersed in the cured product of the curable material, or the UV absorber may be cross-linked with the cured product of the curable material. For example, the UV absorber may include a polymerizable functional group, and the UV absorber may be cross-linked with the cured product of the curable material.

In one embodiment, the curable material may include at least one (meth)acrylate-based compound.

For example, the (meth)acrylate-based compound may have a weight average molecular weight (Mw) in a range of about 50 to about 999.

In one embodiment, the curable material may include at least one di(meth)acrylate compound and at least one mono (meth)acrylate compound.

By controlling the amount ratio of the di(meth)acrylate compound to the mono(meth)acrylate compound, the viscosity of the composition for forming the organic film may be controlled, and accordingly, the thin-film processability (e.g., coatability) may be also improved.

For example, when the composition for forming the organic film has low viscosity (e.g., 50 cp or more), the UV absorber may have excellent dispersibility so that a thin film having a thickness of at least 1 μm may be easily formed and a pattern resolution of at least 1 μm for a thin film may be implemented. In addition, due to the low viscosity, the composition for forming the organic film may be thinned (or coated) through various suitable thinning processes (or various suitable coating processes), such as inkjet printing and vacuum deposition.

In one embodiment, the di(meth)acrylate compound may be selected from:

a compound represented by Formula 1; and ethylene glycol di(meth)acrylate, diethylene glycol di(meth)acrylate, triethylene glycol di(meth)acrylate, propylene glycol di(meth)acrylate, dipropylene glycol di(meth) acrylate, neopentyl glycol di(meth)acrylate, 1,4-butanediol di(meth)acrylate, 1,6-hexanediol di(meth)acrylate, bisphenol-A di(meth)acrylate, pentaerythritol di(meth)acrylate, and dipentaerythritol di(meth)acrylate:

Formula 1

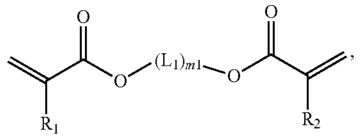

wherein, in Formula 1, $L_1$ may be —O—, —S—, $S(=O)_2$—, —C(=O)—, —C(=O)O—, —C(=O)NH—, —$N(R_6)$—, —$C(R_6)(R_7)$—, —$Si(R_6)(R_7)$—, or an unbranched $C_6$-$C_{20}$ alkylene group, m1 may be an integer of 1 to 10, and $R_1$, $R_2$, $R_6$, and $R_7$ may each independently be selected from hydrogen, deuterium, a $C_1$-$C_{20}$ alkyl group, a $C_2$-$C_{20}$ alkenyl group, a $C_2$-$C_{20}$ alkynyl group, a $C_1$-$C_{20}$ alkoxy group; and deuterium, —F, —Cl, —Br, —I, a hydroxyl group, a cyano group, an epoxy group, a nitro group, an amidino group, a hydrazino group, a hydrazono group, a substituted or unsubstituted $C_1$-$C_{20}$ alkyl group, and a substituted or unsubstituted $C_1$-$C_{20}$ alkoxy group.

For example, at least one of the di(meth)acrylate may be a compound represented by Formula 1.

In one embodiment, the curable material may include a compound represented by Formula 1, and may further include at least one selected from ethylene glycol di(meth) acrylate, diethylene glycol di(meth)acrylate, triethylene glycol di(meth)acrylate, propylene glycol di(meth)acrylate, dipropylene glycol di(meth)acrylate, neopentyl glycol di(meth)acrylate, 1,4-butanediol di(meth)acrylate, 1,6-hexanediol di(meth)acrylate, bisphenol-A di(meth)acrylate, pentaerythritol di(meth)acrylate, and dipentaerythritol di(meth)acrylate.

In one embodiment, the mono(meth)acrylate compound may be selected from biphenyloxy ethyl (meth)acrylate, methyl (meth)acrylate, ethyl (meth)acrylate, n-propyl (meth)acrylate, isopropyl (meth)acrylate, n-butyl (meth) acrylate, isoamyl (meth)acrylate, isobutyl (meth)acrylate, isooctyl (meth)acrylate, sec-butyl (meth)acrylate, t-butyl (meth)acrylate, n-pentyl (meth)acrylate, 3-methylbutyl (meth)acrylate, n-hexyl (meth)acrylate, 2-ethyl-n-hexyl (meth)acrylate, n-octyl (meth)acrylate, cyclohexyl (meth) acrylate, isobornyl (meth)acrylate, dicyclopentanyl (meth) acrylate, dicyclopentanyloxyethyl (meth)acrylate, isomyristyl (meth)acrylate, lauryl (meth)acrylate, methoxydipropylene glycol (meth)acrylate, methoxytripropylene glycol(meth)acrylate, benzyl(meth)acrylate, 2-hydroxyethyl (meth)acrylate, 2-hydroxypropyl (meth)acrylate, 3-hydroxypropyl (meth)acrylate, 4-hydroxybutyl (meth) acrylate, 5-hydroxypentyl (meth)acrylate, 6-hydroxyhexyl (meth)acrylate, 4-hydroxycyclohexyl (meth)acrylate, neopentylglycol mono(meth)acrylate, 3-chloro-2-hydroxypropyl (meth)acrylate, (1,1-dimethyl-3-oxobutyl) (meth)acrylate, 2-acetoacetoxyethyl (meth)acrylate, 2-methoxyethyl (meth)acrylate, 2-ethoxyethyl (meth)acrylate, neopentylglycol mono(meth)acrylate, ethylene glycol monomethyl ether (meth)acrylate, glycerin mono(meth)acrylate, 2-acryloyloxyethyl phthalate, 2-acryloyloxy 2-hydroxyethyl phthalate, 2-acryloyloxyethyl hexahydrophthalate, 2-acryloyloxy propylphthalate, neopentylglycolbenzoate (meth)acrylate, nonylphenoxypolyethylene glycol (meth)acrylate, nonylphenoxypolypropylene glycol (meth)acrylate, paracumylphenoxyethylene glycol (meth)acrylate, ECH modified phenoxy acrylate, phenoxyethyl (meth)acrylate, phenoxydiethylene glycol (meth)acrylate, phenoxyhexaethylene glycol (meth)acrylate, phenoxytetraethylene glycol (meth)acrylate, polyethylene glycol (meth)acrylate, polyethylene glycol phenylether (meth)acrylate, polyethylene glycol-polypropylene glycol (meth)acrylate, polypropylene glycol (meth) acrylate, stearyl (meth)acrylate, ethoxylated phenol acrylate (Phenol (EO) acrylate), ethoxylated cresol (meth)acrylate, dipropylene glycol (meth)acrylate, ethoxylated phenyl (meth)acrylate, ethoxylated succinate (meth)acrylate, tert-butyl (meth)acrylate, tribromophenyl (meth)acrylate, ethoxylated tribromophenyl (meth)acrylate, tridodecyl (meth)acrylate, and tetrahydrofurfuryl (meth)acrylate(Tetrahydofurfuryl (meth)acrylate), but embodiments of the present disclosure are not limited thereto.

For example, at least one of the mono(meth)acrylate compound may be biphenyloxy ethyl(meth)acrylate.

In one embodiment, the curable material may include the biphenyloxy ethyl (meth)acrylate, and may further include at least one compound selected from methyl (meth)acrylate, ethyl (meth)acrylate, n-propyl (meth)acrylate, isopropyl (meth)acrylate, n-butyl (meth)acrylate, isoamyl (meth)acrylate, isobutyl (meth)acrylate, isooctyl (meth)acrylate, sec-butyl (meth)acrylate, t-butyl (meth)acrylate, n-pentyl (meth) acrylate, 3-methylbutyl (meth)acrylate, n-hexyl (meth) acrylate, 2-ethyl-n-hexyl (meth)acrylate, n-octyl (meth) acrylate, cyclohexyl (meth)acrylate, isobornyl (meth) acrylate, dicyclopentanyl (meth)acrylate, dicyclopentanyloxyethyl (meth)acrylate, isomyristyl (meth) acrylate, lauryl (meth)acrylate, methoxydipropylene glycol (meth)acrylate, methoxytripropylene glycol(meth)acrylate, benzyl(meth)acrylate, 2-hydroxyethyl (meth)acrylate, 2-hydroxypropyl (meth)acrylate, 3-hydroxypropyl (meth)acrylate, 4-hydroxybutyl (meth)acrylate, 5-hydroxypentyl (meth)acrylate, 6-hydroxyhexyl (meth)acrylate, 4-hydroxy-cyclohexyl (meth)acrylate, neopentylglycol mono(meth) acrylate, 3-chloro-2-hydroxypropyl (meth)acrylate, (1,1-dimethyl-3-oxobutyl) (meth)acrylate, 2-acetoacetoxyethyl (meth)acrylate, 2-methoxyethyl (meth)acrylate, 2-ethoxy-ethyl (meth)acrylate, neopentylglycol mono(meth)acrylate, ethylene glycol monomethyl ether (meth)acrylate, glycerin mono(meth)acrylate, 2-acryloyloxyethyl phthalate, 2-acryloyloxy 2-hydroxyethyl phthalate, 2-acryloyloxyethyl hexahydrophthalate, 2-acryloyloxy propylphthalate, neopentylglycolbenzoate (meth)acrylate, nonylphenoxypolyethylene glycol (meth)acrylate, nonylphenoxypolypropylene glycol (meth)acrylate, paracumylphenoxyethylene glycol (meth)acrylate, ECH modified phenoxy acrylate, phenoxyethyl (meth)acrylate, phenoxydiethylene glycol (meth)acrylate, phenoxyhexaethylene glycol (meth)acrylate, phenoxytetraethylene glycol (meth)acrylate, polyethylene glycol (meth)acrylate, polyethylene glycol phenylether (meth)acrylate, polyethylene glycol-polypropylene glycol (meth)acrylate, polypropylene glycol (meth) acrylate, stearyl (meth)acrylate, ethoxylated phenol acrylate (Phenol (EO) acrylate), ethoxylated cresol (meth)acrylate, dipropylene glycol (meth)acrylate, ethoxylated phenyl (meth)acrylate, ethoxylated succinate (meth)acrylate, tert-butyl (meth)acrylate, tribromophenyl (meth)acrylate, ethoxylated tribromophenyl (meth)acrylate, tridodecyl (meth)acrylate, and tetrahydrofurfuryl (meth)acrylate(Tetrahydofurfuryl (meth)acrylate).

In one embodiment, the curable material may include the di(meth)acrylate compound and the mono(meth)acrylate compound, and may further include multifunctional (meth) acrylate having at least 3 functional groups.

In one embodiment, the multifunctional (meth)acrylate having at least 3 functional groups may include pentaerythritol tri(meth)acrylate, pentaerythritol tetra(meth)acrylate, pentaerythritol hexa(meth)acrylate, dipentaerythritol tri (meth)acrylate, dipentaerythritol penta(meth)acrylate, dipentaerythritol hexa(meth)acrylate, trimethylolpropane tri (meth)acrylate, tris(meth)acryloyloxyethyl phosphate, ethoxylated trimethylolpropane tri(meth)acrylate, ethoxylated pentaerythritol tetra(meth)acrylate, ethoxylated glycerol tri(meth)acrylate, phosphine oxide (PO) modified glycerol tri(meth)acrylate, pentaerythritol tri(meth)acrylate, ethoxylated phosphoric acid triacrylate, trimethylolpropane tri(meth)acrylate, caprolactone modified trimethylolpropanetri(meth)acrylate, ethoxylated trimethylolpropanetri(meth) acrylate, PO modified trimethylolpropanetri(meth)acrylate, tris(acryloxyethyl)isocyanurate, dipentaerythritolhexa (meth)acrylate, caprolactone modified dipentaerythritolhexa (meth)acrylate, dipentaerythritolhydroxypenta(meth)acrylate, alkyl modified dipentaerythritolpenta(meth)acrylate, dipentaerythritolpoly(meth)acrylate, alkyl modified dipentaerythritoltri(meth)acrylate, or any combination thereof.

In one or more embodiments, the multifunctional (meth) acrylate monomer having at least 3 functional groups may include a multifunctional (meth)acrylate monomer having at least 4 functional groups.

In one or more embodiments, the multifunctional (meth) acrylate monomer having at least 3 functional groups may include pentaerythritol tetra(meth)acrylate, pentaerythritol hexa(meth)acrylate, dipentaerythritol penta(meth)acrylate, dipentaerythritol hexa(meth)acrylate, ethoxylated pentaerythritol tetra(meth)acrylate, caprolactone modified dipentaerythritol hexa(meth)acrylate, dipentaerythritol hydroxypenta(meth)acrylate, alkyl modified dipentaerythritol penta(meth)acrylate, or any combination thereof.

In one or more embodiments, the multifunctional (meth) acrylate monomer having at least 3 functional groups may include tetra-functional (meth)acrylate and hexa-functional (meth)acrylate.

In one or more embodiments, the multifunctional (meth) acrylate monomer having at least 3 functional groups may include pentaerythritol tetra(meth)acrylate, dipentaerythritol tetra(meth)acrylate, ethoxylated pentaerythritol tetra(meth) acrylate, ethoxylated dipentaerythritol tetra(meth)acrylate pentaerythritol hexa(meth)acrylate, dipentaerythritol hexa (meth)acrylate, or any combination thereof.

In one embodiment, an amount of the curable material may be in a range of about 90 parts to about 99 parts by weight based on 100 parts by weight of the composition for forming the organic film.

In one embodiment, the composition for forming the organic film may further include a photopolymerization initiator.

In one embodiment, the photopolymerization initiator may be any suitable material available in the art without particular limitation, and for example, may be a material curable at a wavelength range between 360 nm and 450 nm.

In one embodiment, the composition for forming the organic film may further include two or more types (or kinds) of the photopolymerization initiator. For example, among the two or more types (or kinds) of the photopolymerization initiator, one type (or kind) of the photopolymerization initiator may be cured in an UV region (for example, having a wavelength range between 360 nm and 450 nm), and the other type (or kind) of the photopolymerization initiator may be cured in a visible ray region (for example, having a wavelength range between 450 nm and 770 nm). In one or more embodiments, the two or more types (or kinds) of the photopolymerization initiator may be all cured in the UV region or in the visible ray region.

In one embodiment, the photopolymerization initiator may include at least one selected from an organic peroxide-based compound, an azo-based compound, a benzophenone-based compound, an oxime-based compound, and a phosphine oxide-based compound. For example, the photopolymerization initiator may be a phosphine oxide-based compound.

In one embodiment, an amount of the photopolymerization initiator may be in a range of about 0.5 parts to about 5 parts by weight based on 100 parts by weight of the composition for forming the organic film.

In one or more embodiments, the composition for forming the organic film may further include an adhesive, a radical scavenger, and the like, as needed.

In one embodiment, the thin film encapsulation portion 300 may further include a metal, a metal halide, a metal nitride, a metal oxide, a metal oxynitride, a silicon nitride, a silicon oxide, and a silicon oxynitride.

For example, the thin film encapsulation portion 300 may include at least one selected from $MgF_2$, LiF, $AlF_3$, NaF, silicon oxide, silicon nitride, silicon oxynitride, aluminum oxide, aluminum nitride, aluminum oxynitride, titanium oxide, titanium nitride, tantalum oxide, tantalum nitride, hafnium oxide, hafnium nitride, zirconium oxide, zirconium nitride, cerium oxide, cerium nitride, tin oxide, tin nitride, and magnesium oxide, but embodiments of the present disclosure are not limited thereto.

In one embodiment, the thin film encapsulation portion 300 including the organic film formed by the composition for forming the organic film may have transmittance of less than about 10% for light having a wavelength range between about 400 nm and about 420 nm (for example, about 405 nm).

In one or more embodiments, the thin film encapsulation portion 300 including the organic film formed by the composition for forming the organic film may have transmittance of less than about 10% for light having a wavelength range between about 400 nm and about 420 nm (for example, about 405 nm), and also may have transmittance of greater than 80% for light having a wavelength of 430 nm or more.

In one embodiment, the organic film may have transmittance of greater than about 80% for light having a wavelength range between 430 nm and 800 nm, and may also have transmittance of 10% or less for light having a wavelength of about 405 nm or less.

In one embodiment, the organic film may have transmittance of about 10% or less (for example, about 8% or less) for light having a wavelength range between about 400 nm and about 410 nm (for example, about 405 nm).

In one or more embodiments, the organic film may have transmittance of about 80% or more (for example, about 90% or more) for light having a wavelength of about 430 nm or more, and may also have transmittance of about 10% or less for light having a wavelength of about 405 nm or less.

In one or more embodiments, the thin film encapsulation portion 300 including the organic film formed by the composition for forming the organic film may have a change in transmittance of less than about 1% at a wavelength of about 405 nm, when exposed to UV light (having a wavelength range between about 380 nm to about 400 nm) at an exposure amount of about 52,000 $Wh/m^2$.

In one embodiment, the organic film may have a change in transmittance of less than about 3% at a wavelength range of about 400 nm or more and less than about 410 nm, when exposed to light at an exposure amount of about 52,000 $Wh/m^2$.

In one or more embodiments, the organic film may have a change in transmittance of less than about 1% at wavelength range of about 400 nm or more and less than about 405 nm, when exposed to light at an exposure amount of about 52,000 $Wh/m^2$.

In one embodiment, the organic film may have a change in transmittance of less than about 3% at a wavelength range of about 400 nm or more and less than about 410 nm, when exposed to light having a maximum emission wavelength of about 405 nm or light having a wavelength range between about 380 nm and about 410 nm at an exposure amount of about 52,000 $Wh/m^2$.

In one or more embodiments, the organic film may have a change in transmittance of less than about 1% at wavelength range of about 400 nm or more and less than about 405 nm, when exposed to light having a maximum emission wavelength of about 405 nm or light having a wavelength range between about 380 nm and about 410 nm at an exposure amount of about 52,000 $Wh/m^2$.

The change in transmittance in the wavelength range above may be measured by, for example, exposing the organic film to an LED lamp emitting light having a wavelength range between about 380 nm and about 410 nm and a maximum emission wavelength of about 405 nm.

In one embodiment, a thickness of the organic film may be in a range between about 10 nm and 20 μm, and for example, between about 10 nm and about 10 μm.

In one embodiment, the organic film my further include a matrix resin, and the matrix resin may include at least one selected from an acryl-based resin, a methacryl-based resin, an isoprene-based resin, a vinyl-based resin, an epoxy-based resin, an urethane-based resin, a cellulose-based resin, a perylene-based resin, an imide-based resin, and a silicon-based resin.

In one or more embodiments, the at least one organic film may further include an initiator in addition to the curable material and the UV absorber. The initiator is defined the same as described above.

In one or more embodiments, the at least one organic film may further include the matrix resin and the initiator.

The at least one organic film may be formed in a set or predetermined region by using one or more suitable methods selected from vacuum deposition, spin coating, casting, Langmuir-Blodgett (LB) deposition, ink-jet printing, laser-printing, and laser-induced thermal imaging (LITI). Here, the number and thickness of the organic film may be suitably or appropriately selected in consideration of productivity and device characteristics.

In one embodiment, the thin film encapsulation portion 300 may include at least one organic film, and the at least one organic film may include a first organic film, wherein the first organic film may include a cured product of the composition for forming the organic film, the composition including the curable material and the UV absorber.

In one embodiment, the thin film encapsulation portion 300 may further include at least one inorganic film, and the at least one inorganic film may include a first inorganic film.

In one embodiment, the thin film encapsulation portion 300 may further include at least one inorganic film, and the at least one inorganic film may include a first inorganic film.

The at least one organic film may include the first organic film, and the first organic film may include a cured product of the composition for forming the organic film, the composition including the curable material and the UV absorber.

In one embodiment, the first organic film may be disposed between the organic light-emitting device 200 and the first inorganic film, or the first inorganic film may be disposed between the organic light-emitting device 200 and the first organic film.

In one embodiment, the thin film encapsulation portion 300 may further include at least one inorganic film, and the at least one inorganic film may include the first inorganic film.

In one embodiment, the thin film encapsulation portion 300 may further include at least one inorganic film, and the thin film encapsulation portion 300 may include a sealing unit in which the organic film and the inorganic film are stacked, in the number of n, wherein n is an integer of 1 or more.

In one embodiment, the inorganic film may include a metal, a metal halide, a metal nitride, a metal oxide, a metal oxynitride, a silicon nitride, a silicon oxide, and a silicon oxynitride.

For example, the inorganic film may include at least one selected from $MgF_2$, LiF, $AlF_3$, NaF, silicon oxide, silicon nitride, silicon oxynitride, aluminum oxide, aluminum nitride, aluminum oxynitride, titanium oxide, titanium nitride, tantalum oxide, tantalum nitride, hafnium oxide, hafnium nitride, zirconium oxide, zirconium nitride, cerium oxide, cerium nitride, tin oxide, tin nitride, and magnesium oxide, but embodiments of the present disclosure are not limited thereto.

The at least one inorganic film may be formed in a set or predetermined region by using one or more suitable methods selected from chemical vapor deposition (CVD), plasma enhanced chemical vapor deposition (PECVD), sputtering, atomic layer deposition (ALD), and thermal evaporation.

Here, the number and thickness of the inorganic film may be suitably or appropriately selected in consideration of productivity and device characteristics.

In one embodiment, the at least one organic film may include the first organic film, and the at least one inorganic film may include the first inorganic film, wherein the first organic film may be disposed between the organic light-emitting device 200 and the first inorganic film. For example, the at least one organic film may include the first organic film, and the at least one inorganic film may include the first inorganic film, wherein the first organic film and the second inorganic film may be stacked in this stated order from the organic light-emitting device 200. Here, the meaning of the expression "stacked in this stated order" is understood that a case where a layer is disposed between the organic light-emitting device 200 and the first organic film, and/or a case where a layer is disposed between the first organic film and the first inorganic film is not excluded.

In one or more embodiments, the at least one organic film may include the first organic film, and the at least one inorganic film may include the first inorganic film, wherein the first inorganic film may be disposed between the organic light-emitting device 200 and the first organic film. For example, the at least one organic film may include the first organic film, and the at least one inorganic film may include the first inorganic film, wherein the first inorganic film and the first organic film may be stacked in this stated order from the organic light-emitting device 200.

In one or more embodiments, the at least one organic film may include the first organic film, and the at least one inorganic film may include the first inorganic film and the second inorganic film, wherein the first inorganic film, the first organic film, and the second inorganic film may be stacked in this stated order from the organic light-emitting device 200.

In one or more embodiments, the at least one organic film may include the first organic film and the second organic film, and the at least one inorganic film may include the first inorganic film, wherein the first organic film, the first inorganic film, and the second organic film may be stacked in this stated order from the organic light-emitting device 200.

In one or more embodiments, the at least one organic film may include the first organic film and the second organic film, and the at least one inorganic film may include the first inorganic film and the second inorganic film, wherein the first inorganic film, the first organic film, the second inorganic film, and the second organic film may be stacked in this stated order from the organic light-emitting device 200.

In one or more embodiments, the at least one organic film may include the first organic film and the second organic film, and the at least one inorganic film may include the first inorganic film and the second inorganic film, wherein the first organic film, the first inorganic film, the second organic film, and the second inorganic film may be stacked in this stated order from the organic light-emitting device 200.

In one or more embodiments, the at least one organic film may include the first organic film and the second organic film, and the at least one inorganic film may include the first inorganic film and the second inorganic film, wherein the first inorganic film, the second inorganic film, the first organic film, and the second organic film may be stacked in this stated order from the organic light-emitting device 200.

In one or more embodiments, the at least one organic film may include the first organic film and the second organic film, and the at least one inorganic film may include the first inorganic film and the second inorganic film, wherein the first organic film, the second organic film, the first inorganic film, and the second inorganic film may be stacked in this stated order from the organic light-emitting device 200.

In one or more embodiments, the at least one organic film may include the first organic film and the second organic film, and the at least one inorganic film may include the first inorganic film, the second inorganic film, and a third inorganic film, wherein the first inorganic film, the first organic film, the second inorganic film, the second organic film, and the third inorganic film may be stacked in this stated order from the organic light-emitting device 200.

In one or more embodiments, the at least one organic film may include the first organic film, the second organic film and the third organic film, and the at least one inorganic film may include the first inorganic film and the second inorganic film, wherein the first organic film, the first inorganic film, the second organic film, the second inorganic film, and the third organic film may be stacked in this stated order from the organic light-emitting device 200, but embodiments of the present disclosure are not limited thereto. Not only the number of the organic film and the inorganic film, but also the stacking order of the inorganic film and the organic film may be suitably or appropriately modified according to the design.

The thin film encapsulation portion 300 may further include at least one low inorganic film or low organic film between the sealing unit and the light-emitting diode 200 or between the sealing unit and the pixel defined layer 400.

In one embodiment, a thin-film unit may include an organic-inorganic composite layer in which the organic film and the inorganic film are stacked in this stated order from the light-emitting diode 200 and the pixel defined layer 400, or an inorganic-organic composite film in which the inorganic film and the organic film are stacked in this stated order from the light-emitting diode 200 and the pixel defined layer 400.

In one embodiment, the thin film encapsulation portion 300 may include at least one thin-film unit, and may further include at least one organic film between the sealing unit and the light-emitting diode 200 or between the sealing unit and the pixel defined layer 400.

In one embodiment, the thin film encapsulation portion 300 may include at least one thin-film unit, and may further include at least one inorganic film between the sealing unit and the light-emitting diode 200 or between the sealing unit and the pixel defined layer 400.

In one embodiment, the thin film encapsulation portion 300 may include two types (or kinds) of the thin-film unit.

In one embodiment, the thin film encapsulation portion 300 may include two types (or kinds) of the thin-film unit, and may further include at least one organic film between the thin-film unit and the light-emitting diode 200 or between the thin-film unit and the pixel defined layer 400.

In one embodiment, the thin film encapsulation portion 300 may include two types (or kinds) of the thin-film unit, and may further include at least one inorganic film between the thin-film unit and the light-emitting diode 200 or between the thin-film unit and the pixel defined layer 400.

For example, the thin film encapsulation portion 300 may have a first inorganic film/first organic film/second inorganic film structure, a first organic film/first inorganic film/second organic film/second inorganic film structure, a first inorganic film/second inorganic film/first organic film/third inorganic film/second organic film structure, or a first organic film/second organic film/first inorganic film/third organic film/ second inorganic film structure, but embodiments of the present disclosure are not limited thereto. Here, the number and stacking order of the organic film and the inorganic film may be suitably or appropriately modified.

In one embodiment, between the sealing unit and the light-emitting diode 200 or between the sealing unit and the pixel defined layer 400, at least one of a capping layer and a protection layer may be further disposed.

Figure 2:
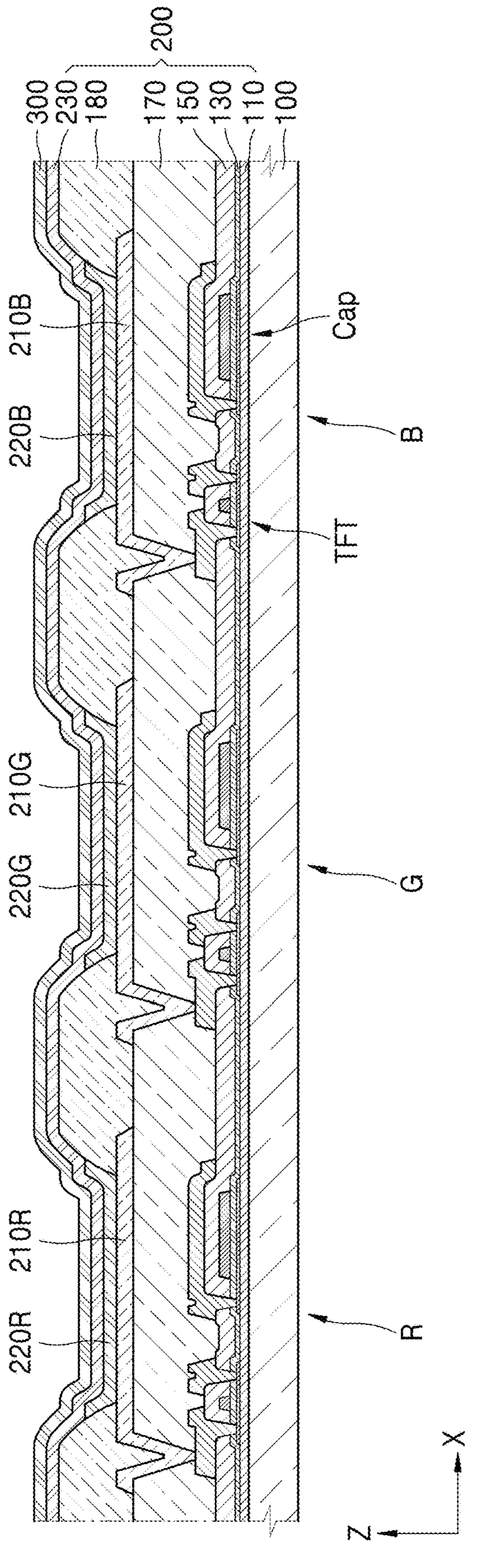
FIG. 2 is a schematic cross-sectional view of a structure of an electronic apparatus according to an embodiment.

FIG. 2 is a schematic cross-sectional view of a structure of an electronic apparatus according to an embodiment.

Referring to FIG. 2, first, a backplane may be formed. Here, the backplane may include at least a portion of a substrate 100, a plurality of first electrodes 210R, 210G, and 2108 formed on the substrate 100, and the pixel defined layer 180 formed to expose at least a portion of a plurality of center portions of the plurality of the first electrodes 210R, 210G, 210B. Here, the pixel defined layer 180 may have a protruding shape (in the +z direction) beyond the plurality of the first electrodes 210R, 210G, and 2108, with respect to the substrate 100.

The plurality of the first electrodes 210R, 210G, and 2108 may be understood as a plurality of pixel electrodes. Among the plurality of the pixel electrodes, a pixel electrode 210R may be understood as a first pixel electrode, a pixel electrode 210G may be understood as a second pixel electrode, and a pixel electrode 2108 may be understood as a third pixel electrode, in consideration that an intermediate layer formed on each of the first to third pixel electrodes may be different from each other. Hereinafter, for convenience, the terms pixel electrodes 210R, 210G, and 2108 will be used rather than the terms first, second, and third pixel electrodes. The pixel electrode may be defined in the same manner as the first electrode.

The pixel defined layer 180 of FIG. 2 may have openings corresponding to the respective sub-pixels, and that is, central portions of each of the pixel electrodes 210R, 210G, and 210B, or openings to expose the entire of the pixel electrodes 210R, 210G, and 210B, so as to define a pixel. In addition, the pixel defined layer 180 of FIG. 2 may prevent or reduce the occurrence of arcs at the ends of the pixel electrodes 210R, 210G, and 2108 by increasing the distance between the ends of the pixel electrodes 210R, 210G, and 2108 and the second electrode above the pixel electrodes 210R, 210G, and 210B.

Such a backplane may further include various suitable other components as needed. For example, as shown in FIG. 2, a thin-film transistor (TFT) or a capacitor (Cap) may be formed on the substrate 100. In addition, the backplane may include a buffer layer 110 formed to prevent impurities from penetrating into a semiconductor layer of a TFT (or to reduce a likelihood or amount of impurities penetrating into a semiconductor layer of a TFT), a gate insulating film 130 for insulating a semiconductor layer of a TFT and a gate electrode, an intermediate insulating layer for insulating a source electrode/drain electrode and a gate electrode of a TFT, a planarization layer 170 having a flat top by covering a TFT, and the like.

As such, following the formation of the backplane, intermediate layers 220R, 220G, and 220B may be formed. The intermediate layers 220R, 220G, and 220B may each have a multi-layered structure including the emission layer. Here, unlike shown in the figure, some of the intermediate layers 220R, 220G, and 220B may serve as common layers that approximately correspond to the entire surface of the substrate 100 while the other intermediate layers 220R, 220G, and 220B may serve as pattern layers that are patterned to correspond to the pixel electrodes 210R, 210G, and 210B.

Following the formation of the intermediate layers 220R, 220G, and 220B, a second electrode 230 may be formed on the intermediate layers 220R, 220G, and 220B.

At least one layer selected from a hole injection layer, a hole transport layer, an emission auxiliary layer, and an electron blocking layer may be included between the emission layer and the first electrode, and at least one layer selected from a buffer layer, a hole blocking layer, an electron transport layer, and an electron injection layer may be included between the emission layer and the second electrode.

In one embodiment, the emission layer may be patterned into a red emission layer, a green emission layer, or a blue emission layer, according to a sub-pixel. In one or more embodiments, the emission layer may have a stacked structure of two or more layers selected from a red emission layer, a green emission layer, and a blue emission layer, in which the two or more layers contact each other or are separated from each other. In one or more embodiments, the emission layer may include two or more materials selected from a red light-emitting material, a green light-emitting material, and a blue light-emitting material, in which the two or more materials are mixed with each other in a single layer to emit white light.

In one embodiment, the emission layer may include an organic material, an inorganic material, or any combination thereof.

In one embodiment, the emission layer may include a host and a dopant. The dopant may include at least one selected from a phosphorescent dopant and a fluorescent dopant.

In the emission layer, an amount of the dopant may be generally in a range of about 0.01 parts by weight to about 30 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. When the thickness of the emission layer is in this range, excellent emission characteristics may be obtained without a substantial increase in driving voltage.

In one embodiment, the emission layer may include an organometallic compound.

Host in Emission Layer

The host may include a compound represented by Formula 301:

$$[Ar_{301}]_{xb11}\text{-}[(L_{301})_{xb1}\text{-}R_{301}]_{xb21}. \qquad \text{Formula 301}$$

In Formula 301, $Ar_{301}$ may be a substituted or unsubstituted $C_5$-$C_{60}$ carbocyclic group or a substituted or unsubstituted $C_1$-$C_{60}$ heterocyclic group, xb11 may be 1, 2, or 3, $L_{301}$ may be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xb1 may be an integer of 0 to 5, $R_{301}$ may be selected from deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_{301})(Q_{302})(Q_{303})$, —$N(Q_{301})(Q_{302})$, —$B(Q_{301})(Q_{302})$, —$C(=O)(Q_{301})$, —$S(=O)_2(Q_{301})$, and —$P(=O)(Q_{301})(Q_{302})$, xb21 may be an integer of 1 to 5, and $Q_{301}$ to $Q_{303}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In one embodiment, in Formula 301, $Ar_{301}$ may be selected from:

a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group; and a naphthalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, a dibenzofuran group, and a dibenzothiophene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_{31}$ to $Q_{33}$ may each independently be selected from a $C_1$-$C_{10}$ alkyl group, a $C_1$-$C_{10}$ alkoxy group, a phenyl group, a biphenyl group, a terphenyl group, and a naphthyl group, but embodiments of the present disclosure are not limited thereto.

In Formula 301, when xb11 is two or more, two or more of $Ar_{301}$(s) may be linked via a single bond.

In one or more embodiments, the compound represented by Formula 301 may be represented by Formula 301-1 or 301-2:

Formula 301-1

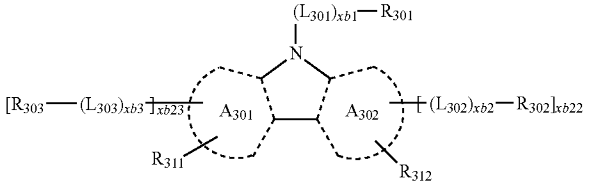

Formula 301-2

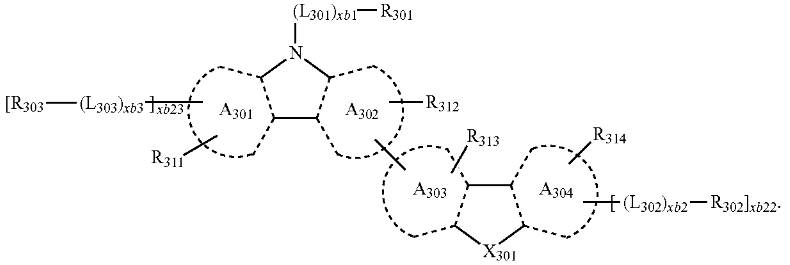

In Formulae 301-1 to 301-2, $A_{301}$ to $A_{304}$ may each independently be selected from a benzene group, a naphthalene group, a phenanthrene group, a fluoranthene group, a triphenylene group, a pyrene group, a chrysene group, a pyridine group, a pyrimidine group, an indene group, a fluorene group, a spiro-bifluorene group, a benzofluorene group, a dibenzofluorene group, an indole group, a carbazole group, a benzocarbazole group, a dibenzocarbazole group, a furan group, a benzofuran group, a dibenzofuran group, a naphthofuran group, a benzonaphthofuran group, a dinaphthofuran group, a thiophene group, a benzothiophene group, a dibenzothiophene group, a naphthothiophene group, a benzonaphthothiophene group, and a dinaphthothiophene group, $X_{301}$ may be O, S, or N-$[(L_{304})_{xb4}$-$R_{304}]$, $R_{311}$ to $R_{314}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, xb22 and xb23 may each independently be 0, 1, or 2, $L_{301}$, xb1, $R_{301}$, and $Q_{31}$ to $Q_{33}$ may respectively be defined the same as described above, $L_{302}$ to $L_{304}$ may respectively be defined the same as described in connection with $L_{301}$, xb2 to xb4 may respectively be defined the same as described in connection with xb1, and $R_{302}$ to $R_{304}$ may respectively be defined the same as described in connection with $R_{301}$.

For example, in Formulae 301, 301-1, and 301-2, $L_{301}$ to $L_{304}$ may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, a pyridinylene group, an imidazolylene group, a pyrazolylene group, a thiazolylene group, an isothiazolylene group, an oxazolylene group, an isoxazolylene group, a thiadiazolylene group, an oxadiazolylene group, a pyrazinylene group, a pyrimidinylene group, a pyridazinylene group, a triazinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a phenanthridinylene group, an acridinylene group, a phenanthrolinylene group, a phenazinylene group, a benzimidazolylene group, an isobenzothiazolylene group, a benzoxazolylene group, an isobenzoxazolylene group, a triazolylene group, a tetrazolylene group, an imidazopyridinylene group, an imidazopyrimidinylene group, and an azacarbazolylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, $—Si(Q_{31})(Q_{32})(Q_{33})$, $—N(Q_{31})(Q_{32})$, $—B(Q_{31})(Q_{32})$, $—C(=O)(Q_{31})$, $—S(=O)_2(Q_{31})$, and $—P(=O)(Q_{31})(Q_{32})$, and $Q_{31}$ to $Q_{33}$ may respectively be defined the same as described above.

In one embodiment, in Formulae 301, 301-1, and 301-2, $R_{301}$ to $R_{304}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, and an azacarbazolyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, an imidazolyl group, a pyrazolyl group, a thiazolyl group, an isothiazolyl group, an oxazolyl group, an isoxazolyl group, a thiadiazolyl group, an oxadiazolyl group, a pyrazinyl group, a pyrimidinyl group, a pyridazinyl group, a triazinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzimidazolyl group, an isobenzothiazolyl group, a benzoxazolyl group, an isobenzoxazolyl group, a triazolyl group, a tetrazolyl group, an imidazopyridinyl group, an imidazopyrimidinyl group, an azacarbazolyl group, —Si($Q_{31}$)($Q_{32}$)($Q_{33}$), —N($Q_{31}$)($Q_{32}$), —B($Q_{31}$)($Q_{32}$), —C(=O)($Q_{31}$), —S(=O)$_2$($Q_{31}$), and —P(=O)($Q_{31}$)($Q_{32}$), and $Q_{31}$ to $Q_{33}$ may respectively be defined the same as described above.

In one embodiment, the host may include an alkaline earth metal complex. For example, the host may be selected from a Be complex (for example, Compound H55), a Mg complex, and a Zn complex.

The host may include at least one selected from 9,10-di(2-naphthyl)anthracene (ADN), 2-methyl-9,10-bis(naphthalen-2-yl)anthracene (MADN), 9,10-di-(2-naphthyl)-2-t-butyl-anthracene (TBADN), 4,4'-bis(N-carbazolyl)-1,1'-biphenyl (CBP), 1,3-di-9-carbazolylbenzene (mCP), 1,3,5-tri(carbazol-9-yl)benzene (TCP), and Compounds H1 to H55, but embodiments of the present disclosure are not limited thereto:

H1

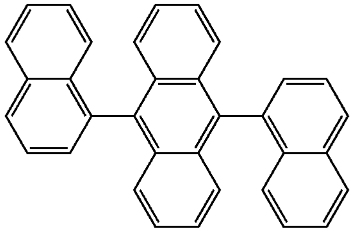

-continued

H2

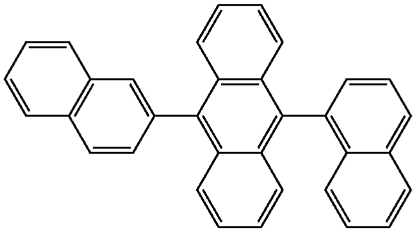

H3

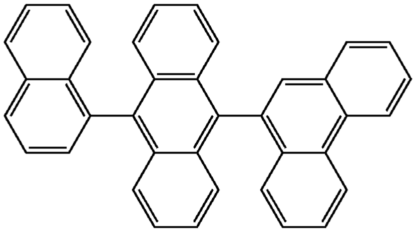

H4

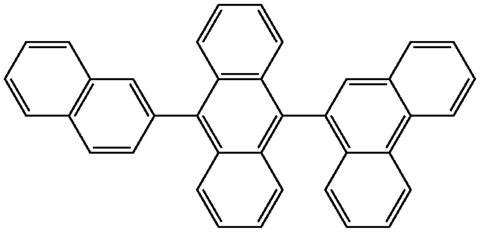

H5

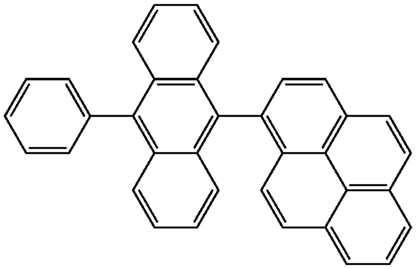

H6

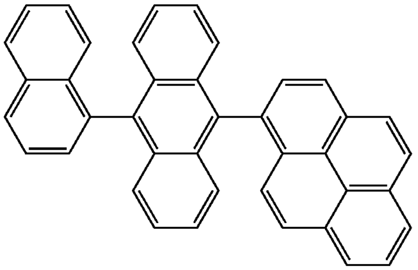

H7

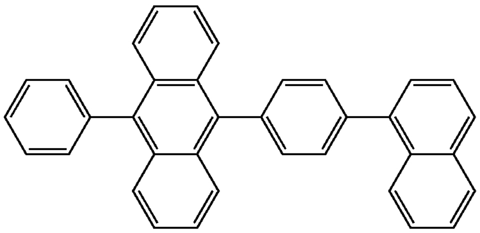

-continued
H8
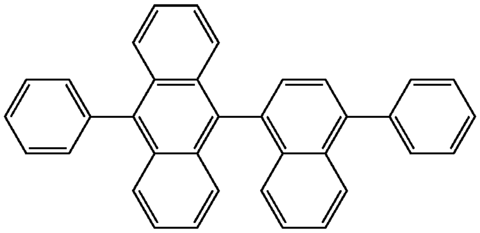
H9
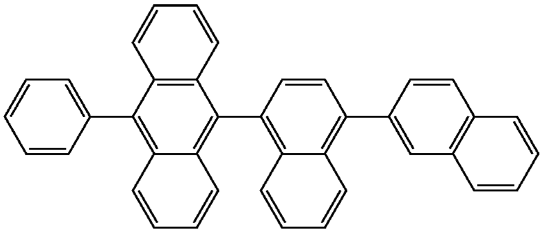
H10
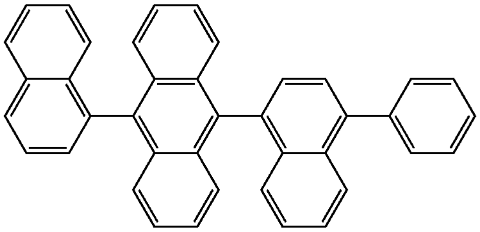
H11
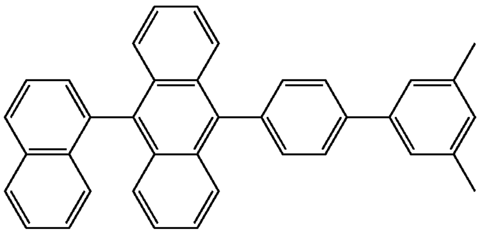
H12
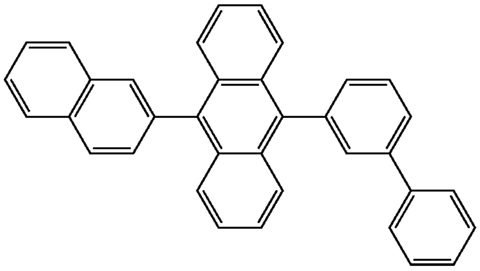
H13
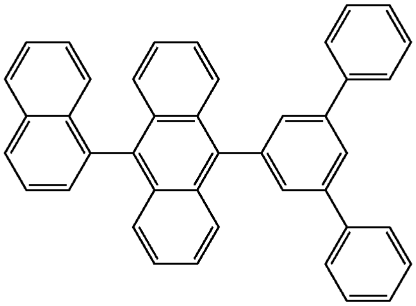
-continued
H14
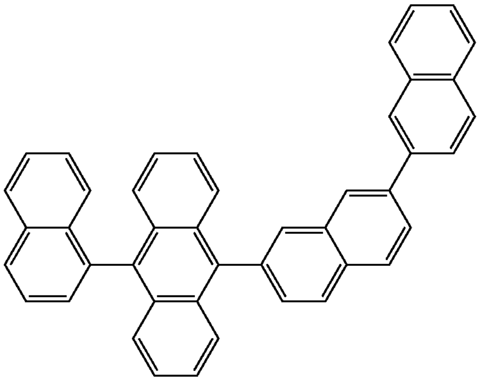
H15
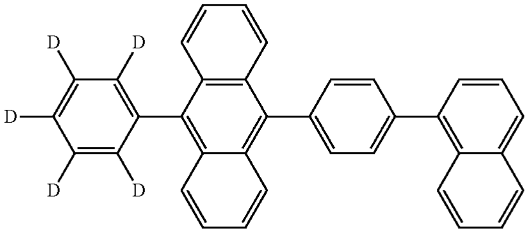
H16
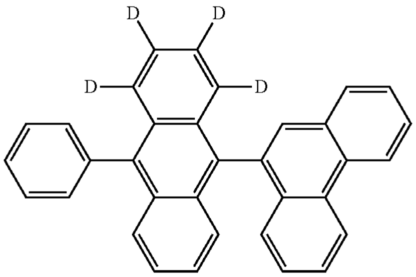
H17
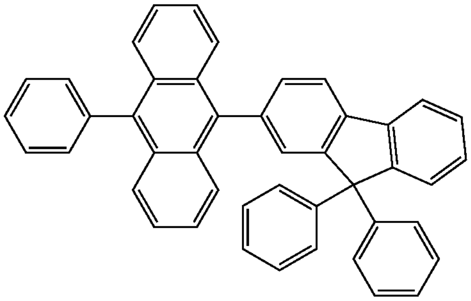
H18
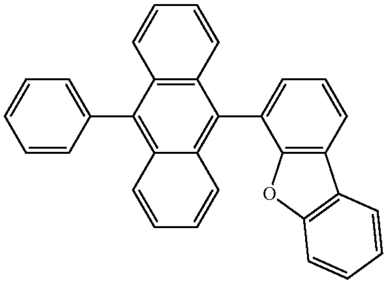

-continued
H19
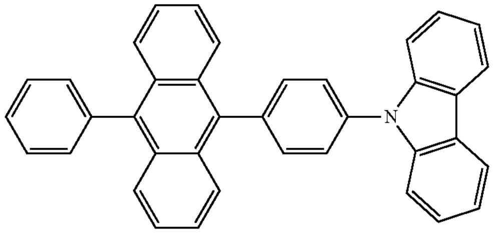
H20
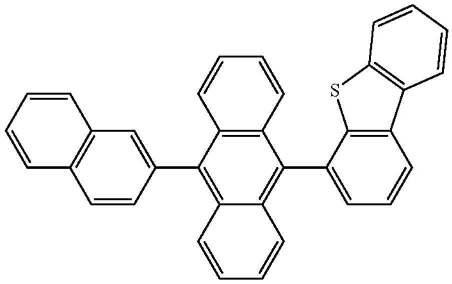
H21
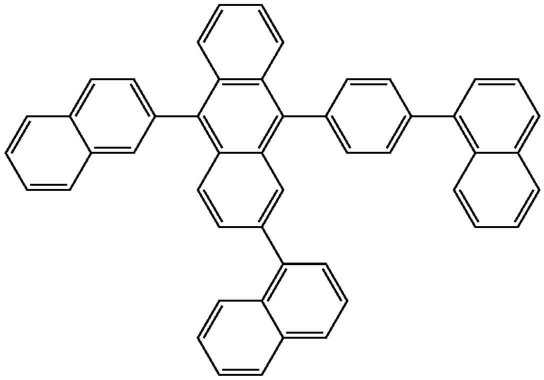
H22
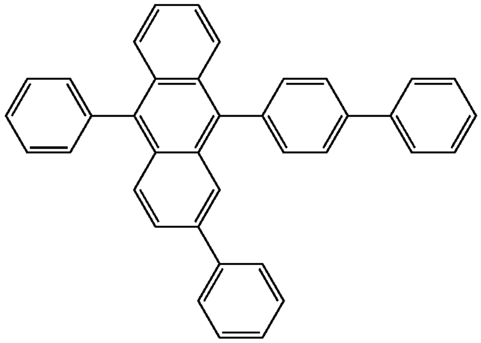
-continued
H23
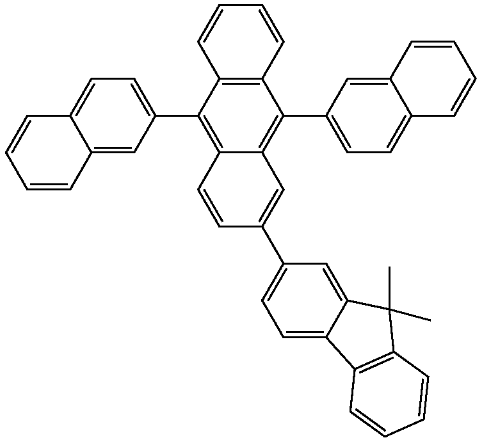
H24
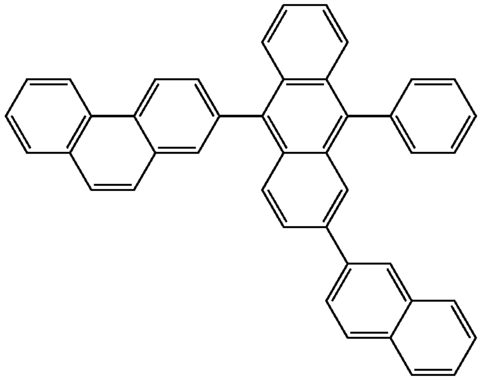
H25
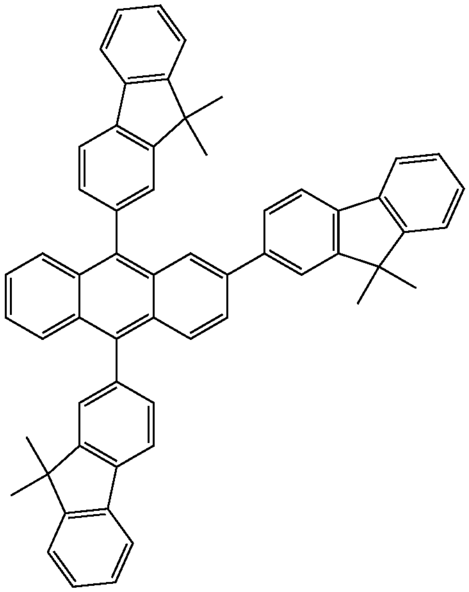

-continued
H26
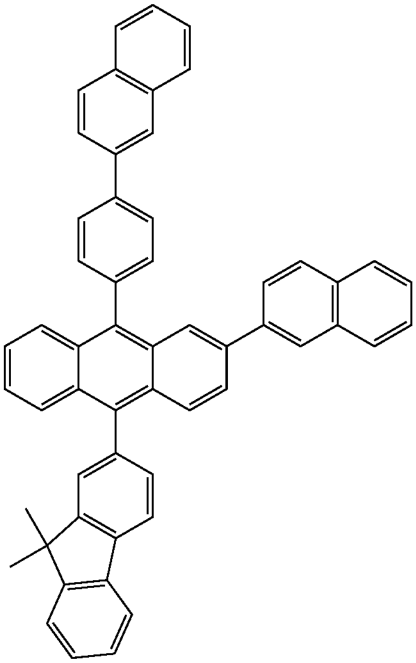
H27
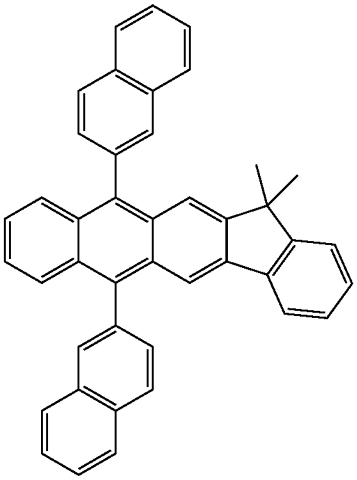
H28
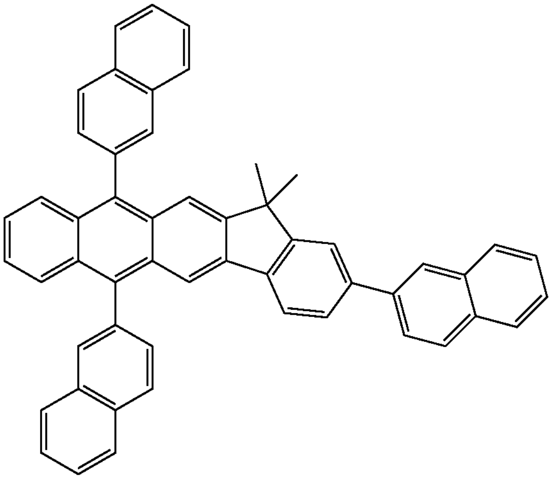
-continued
H29
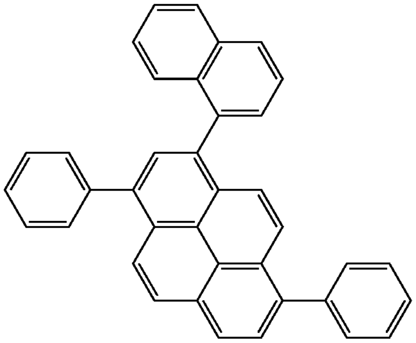
H30
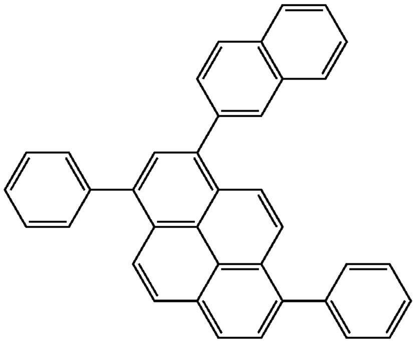
H31
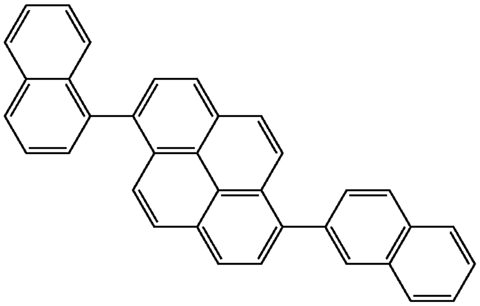
H32
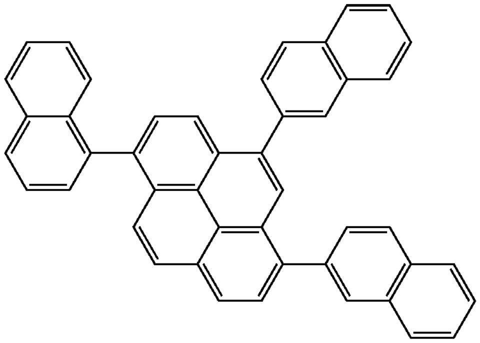
H33
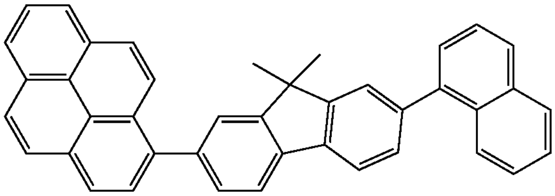

-continued
H34
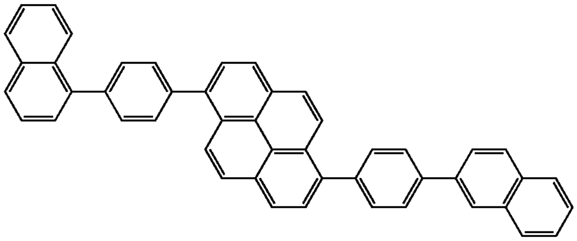
H35
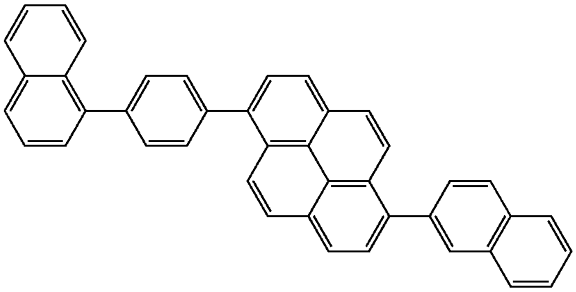
H36
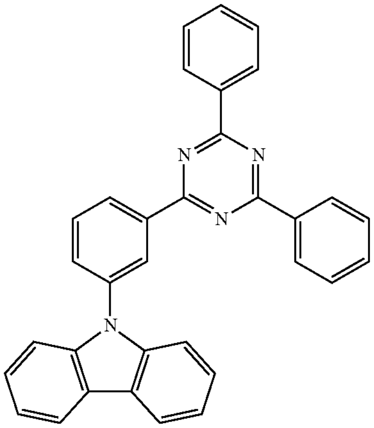
H37
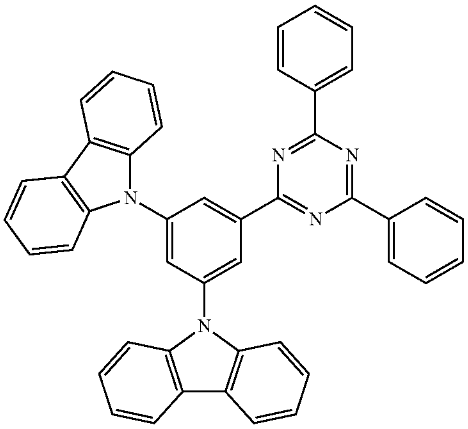
-continued
H38
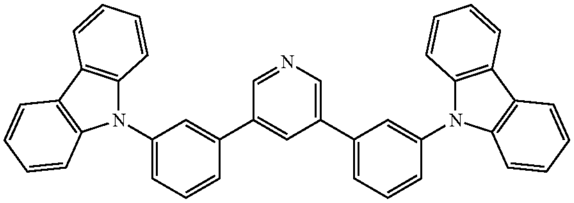
H39
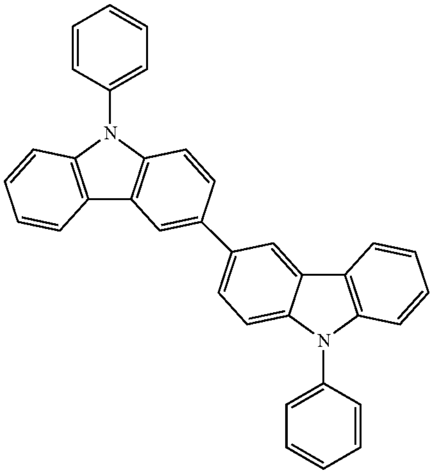
H40
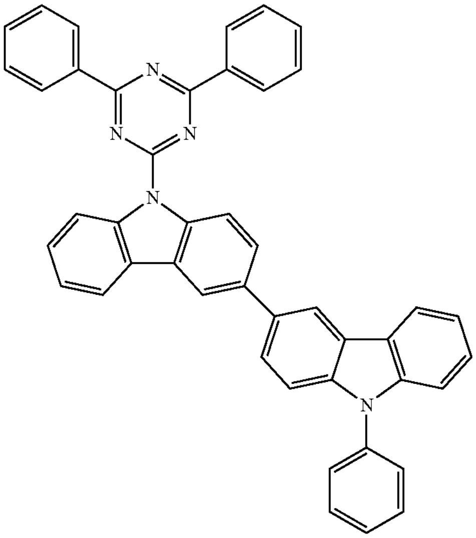

-continued
H41
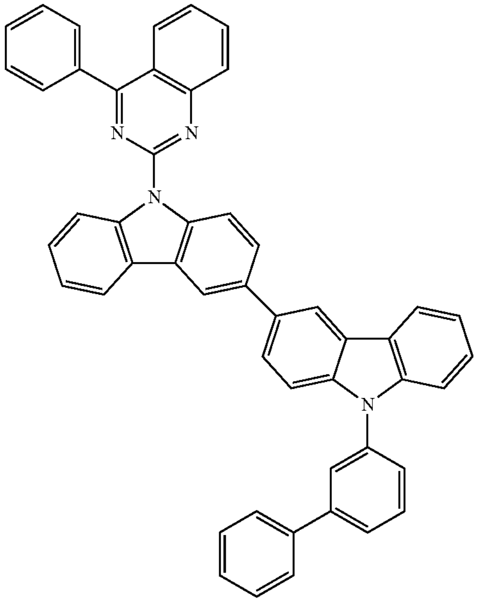
H42
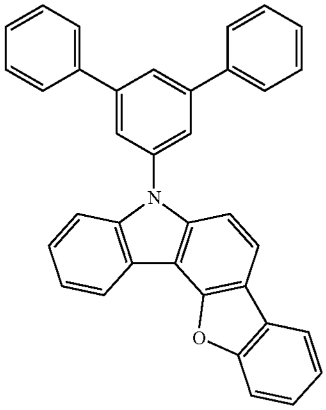
H43
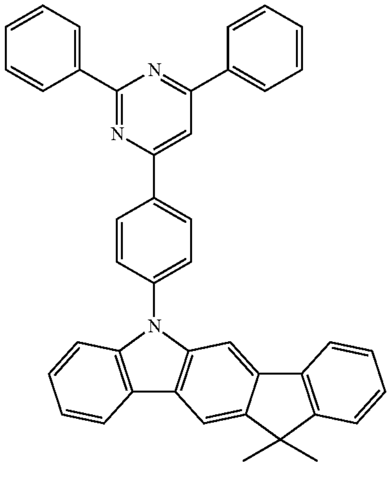
-continued
H44
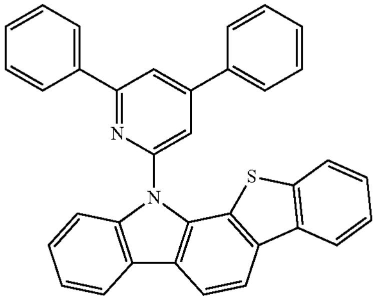
H45
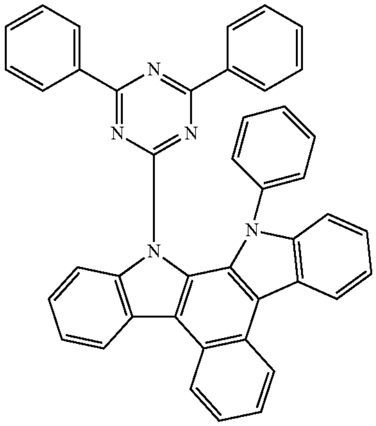
H46
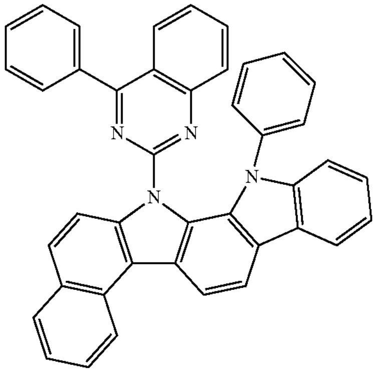
H47
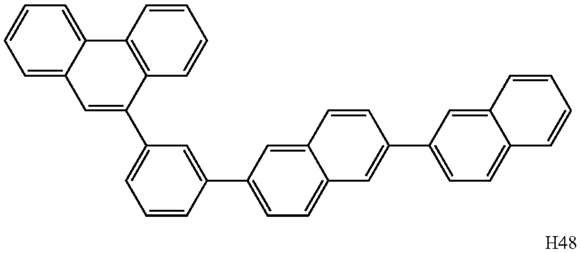
H48
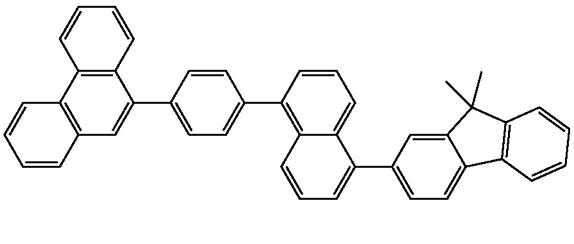

-continued

H49

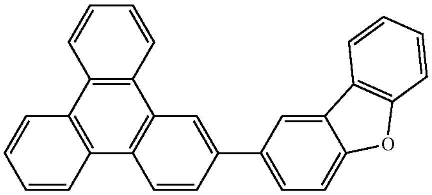

H50

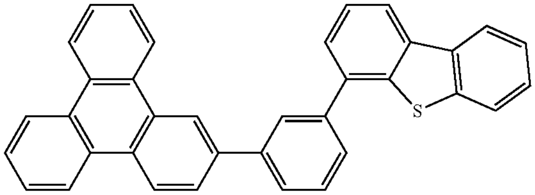

H51

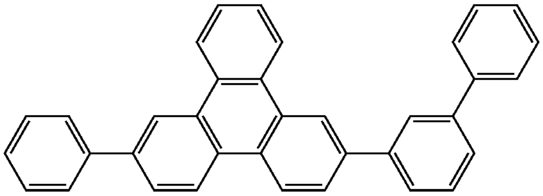

H52

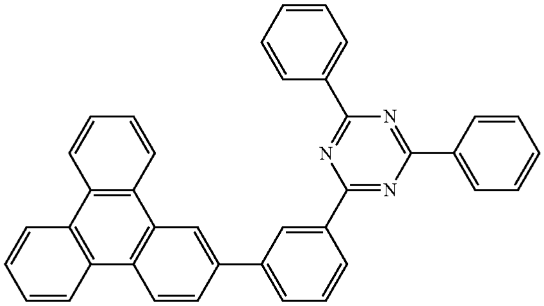

H53

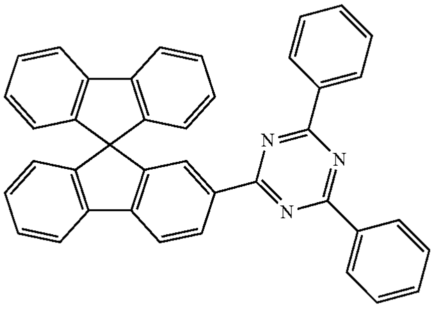

-continued

H54

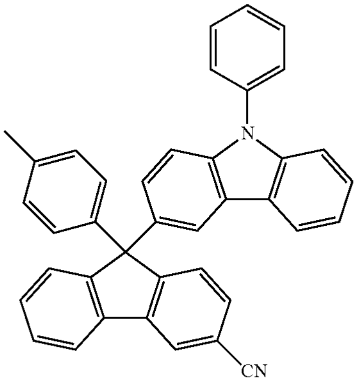

H55

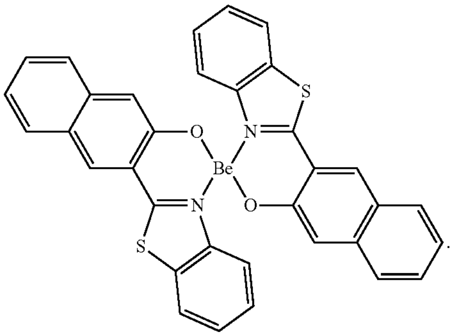

Phosphorescent Dopant in Emission Layer of Organic Layer 150

In one embodiment, the organometallic compound included in the emission layer may be a phosphorescent dopant.

In one embodiment, the phosphorescent dopant may include an organometallic complex represented by Formula 401:

Formula 401

$$M(L_{401})_{xc1}(L_{402})_{xc2}$$

Formula 402

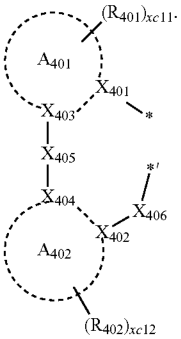

In Formulae 401 and 402,

M may be selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ may be selected from a ligand represented by Formula 402, and xc1 may be 1, 2, or 3. When xc1 is two or more, two or more of L401(s) may be identical to or different from each other, $L_{402}$ may be an organic ligand, and xc2 may be an integer of 0 to 4. When xc2 is two or more, two or more of L402(s) may be identical to or different from each other, $X_{401}$ to $X_{404}$ may each independently be nitrogen or carbon, $X_{401}$ and $X_{403}$ may be linked each other via a single bond or a double bond, and $X_{402}$ and $X_{404}$ may be linked each other via a single bond or a double bond, $A_{401}$ and $A_{402}$ may each independently be a C5-C60 carbocyclic group or a C1-C60 heterocyclic group, $X_{405}$ may be a single bond, *—O—*', *—S—*', *—C(=O)—*', *—N(Q411)-*', *—C(Q411)(Q412)-*', *—C(Q411)=C(Q412)-*', *—C(Q411)=*', or *=C(Q411)=*', wherein Q411 and Q412 may be hydrogen, deuterium, a C1-C20 alkyl group, a C1-C20 alkoxy group, a phenyl group, a biphenyl group, a terphenyl group, or a naphthyl group, $X_{406}$ may be a single bond, O or S, $R_{401}$ and $R_{402}$ may each independently be selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group —$Si(Q_{401})(Q_{402})(Q_{403})$, —$N(Q_{401})(Q_{402})$, —$B(Q_{401})(Q_{402})$, —$C(=O)(Q_{401})$, —$S(=O)_2(Q_{401})$, and —$P(=O)(Q_{401})(Q_{402})$, wherein $Q_{401}$ to $Q_{403}$ may each independently be selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 may each independently be an integer of 0 to 10, and in Formula 402, * and *' each indicate a binding site to M of Formula 401.

In one embodiment, in Formula 402, $A_{401}$ and $A_{402}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group.

In one or more embodiment, in Formula 402, $A_{401}$ may be a benzene group, and $A_{402}$ may be a pyridine group.

In one or more embodiments, in Formula 402, i) $X_{401}$ may be nitrogen, and $X_{402}$ may be carbon, or ii) $X_{401}$ and $X_{402}$ may be both nitrogen.

In one or more embodiments, in Formula 402, $R_{401}$ and $R_{402}$ may each independently be selected from:

hydrogen, deuterium, —F, —Cl, —Br, —I, a hydroxyl group, a cyano group, a nitro group, an amidino group, a hydrazino group, a hydrazono group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amidino group, a hydrazino group, a hydrazono group, a phenyl group, a naphthyl group, a cyclopentyl group, a cyclohexyl group, an adamantanyl group, a norbornanyl group, and a norbornenyl group;

a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group;

a cyclopentyl group, a cyclohexyl group, an adamantanyl group, a norbornanyl group, a norbornenyl group a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a cyclopentyl group, a cyclohexyl group, an adamantanyl group, a norbornanyl group, a norbornenyl group, a phenyl group, a biphenyl group, a terphenyl group, a naphthyl group, a fluorenyl group, a pyridinyl group, a pyrazinyl group, a pyrimidinyl group, a pyridazinyl group, a triazinyl group, a quinolinyl group, an isoquinolinyl group, a quinoxalinyl group, a quinazolinyl group, a carbazolyl group, a dibenzofuranyl group, and a dibenzothiophenyl group; and —$Si(Q_{401})(Q_{402})(Q_{403})$, —$N(Q_{401})(Q_{402})$, —$B(Q_{401})(Q_{402})$, —$C(=O)(Q_{401})$, —$S(=O)_2(Q_{401})$, and —$P(=O)(Q_{401})(Q_{402})$, and $Q_{401}$ to $Q_{403}$ may each independently be selected from a $C_1$-$C_{10}$ alkyl group, a $C_1$-$C_{10}$ alkoxy group, a phenyl group, a biphenyl group, and a naphthyl group, but embodiments of the present disclosure are not limited thereto.

In one or more embodiments, in Formula 401, when xc1 is two or more, two A401(s) among a plurality of L401(s) may optionally be linked via a linking group, X407, or two A402(s) may optionally be linked via a linking group, X408 (see Compounds PD1 to PD4 and PD7). X407 and X408 may each independently be a single bond, *—O—*', *—S—*', *—C(=O)—*', *—N(Q413)-*', *—C(Q413)(Q414)-*', or *—C(Q413)=C(Q414)-*' (wherein Q413 and Q414 may each independently be hydrogen, deuterium, a C1-C20 alkyl group, a C1-C20 alkoxy group, a phenyl group, a biphenyl group, a terphenyl group, or a naphthyl group), but embodiments of the present disclosure are not limited thereto.

L402 in Formula 401 may be a monovalent, divalent, or trivalent organic ligand. For example, L402 may be selected from halogen, diketone (for example, acetylacetonate), carboxylic acid (for example, picolinate), —C(=O), isonitrile, —CN, and phosphorus (for example, phosphine, or phosphite), but embodiments of the present disclosure are not limited thereto.
In one or more embodiments, the phosphorescent dopant may be selected from, for example, Compounds PD1 to PD25, but embodiments of the present disclosure are not limited thereto:
PD1
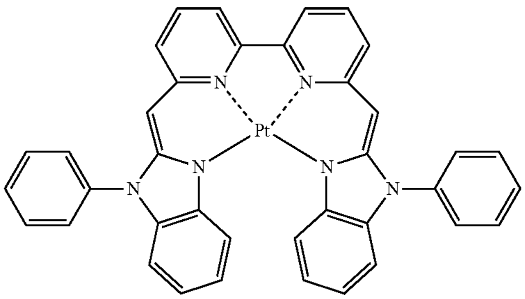
PD2
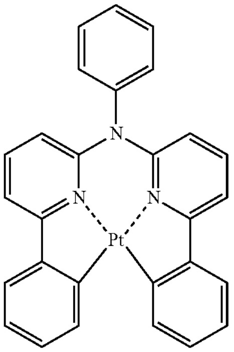
PD3
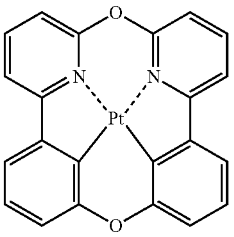
PD4
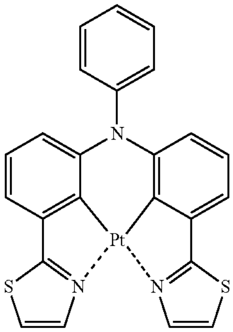
-continued
PD5
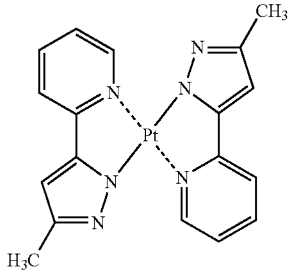
PD6
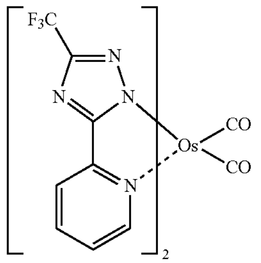
PD7
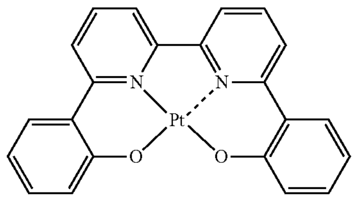
PD8
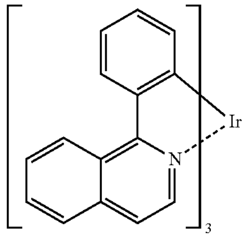
PD9
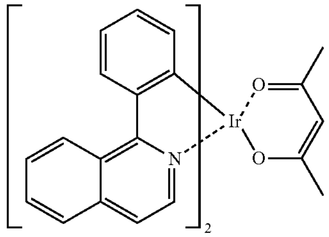
PD10
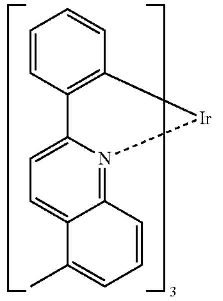

-continued
PD11
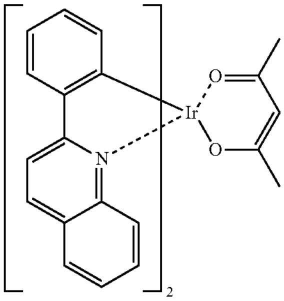
PD12
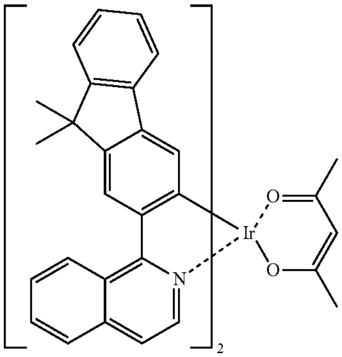
PD13
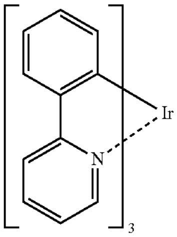
PD14
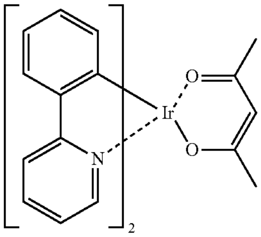
PD15
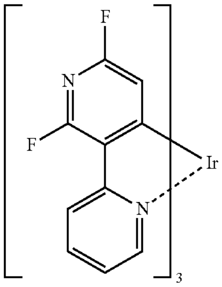
-continued
PD16
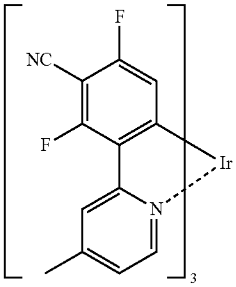
PD17
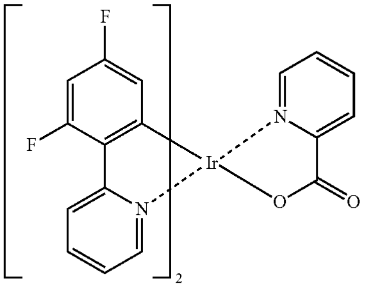
PD18
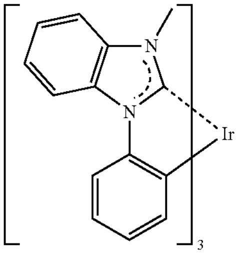
PD19
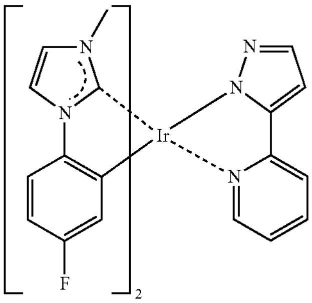
PD20
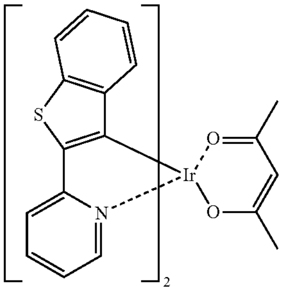

-continued

PD21

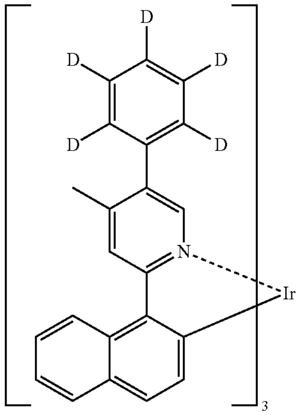

PD22

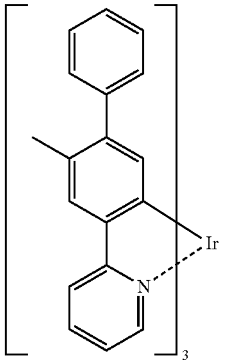

PD23

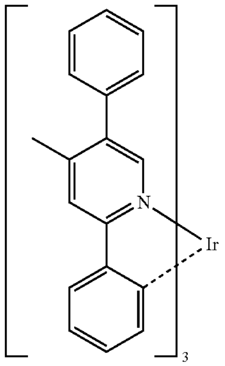

PD24

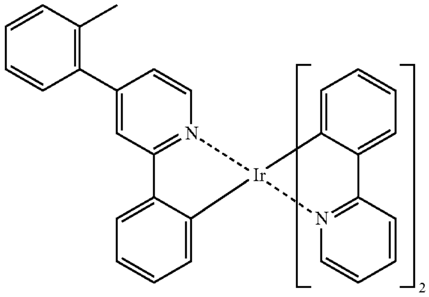

-continued

PD25

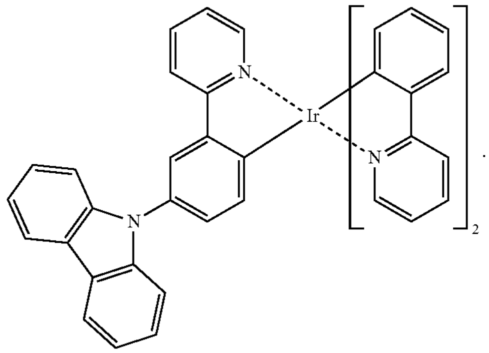

In one embodiment, the emission layer may emit red phosphorescence having a maximum emission wavelength range between about 590 nm and about 780 nm.

In one embodiment, the organometallic compound included in the emission layer, for example, the organometallic compound emitting light having a long wavelength range between about 590 nm and about 780 nm may be subjected to dissociation of a metal-ligand complex due to exposure to UV light. The electronic apparatus according to an embodiment may include the cured product of the composition for forming the organic film in the thin film encapsulation portion, the composition including the UV absorber and the curable material including the (meth)acrylate compound, thereby preventing or reducing deterioration of the organometallic compound in the wavelength range of UV light.

Fluorescent Dopant in Emission Layer

The fluorescent dopant may include an arylamine compound or a styrylamine compound.

The fluorescent dopant may include a compound represented by Formula 501:

Formula 501

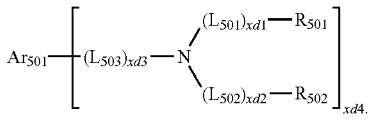

In Formula 501, $Ar_{501}$ may be a substituted or unsubstituted $C_5$-$C_{60}$ carbocyclic group or a substituted or unsubstituted $C_1$-$C_{60}$ heterocyclic group, $L_{501}$ to $L_{503}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group, xd1 to xd3 may each independently be an integer of 0 to 3, $R_{501}$ and $R_{502}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and xd4 may be an integer of 1 to 6.

In one embodiment, $Ar_{501}$ in Formula 501 may be selected from:

a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group; and a naphthalene group, a heptalene group, a fluorene group, a spiro-bifluorene group, a benzofluorene group, a dibenzofluorene group, a phenalene group, a phenanthrene group, an anthracene group, a fluoranthene group, a triphenylene group, a pyrene group, a chrysene group, a naphthacene group, a picene group, a perylene group, a pentaphene group, an indenoanthracene group, and an indenophenanthrene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, and a naphthyl group.

In one or more embodiments, $L_{501}$ to $L_{503}$ in Formula 501 may each independently be selected from:

a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group; and a phenylene group, a naphthylene group, a fluorenylene group, a spiro-bifluorenylene group, a benzofluorenylene group, a dibenzofluorenylene group, a phenanthrenylene group, an anthracenylene group, a fluoranthenylene group, a triphenylenylene group, a pyrenylene group, a chrysenylene group, a perylenylene group, a pentaphenylene group, a hexacenylene group, a pentacenylene group, a thiophenylene group, a furanylene group, a carbazolylene group, an indolylene group, an isoindolylene group, a benzofuranylene group, a benzothiophenylene group, a dibenzofuranylene group, a dibenzothiophenylene group, a benzocarbazolylene group, a dibenzocarbazolylene group, a dibenzosilolylene group, and a pyridinylene group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group.

In one or more embodiments, in Formula 501, $R_{501}$ and $R_{502}$ may each independently be selected from:

a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group; and a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, and a pyridinyl group, each substituted with at least one selected from deuterium, —F, —Cl, —Br, —I, a hydroxyl group, a cyano group, a nitro group, an amidino group, a hydrazino group, a hydrazono group, a $C_1$-$C_{20}$ alkyl group, a $C_1$-$C_{20}$ alkoxy group, a phenyl group, a biphenyl group, a terphenyl group, a naphthyl group, a fluorenyl group, a spiro-bifluorenyl group, a benzofluorenyl group, a dibenzofluorenyl group, a phenanthrenyl group, an anthracenyl group, a fluoranthenyl group, a triphenylenyl group, a pyrenyl group, a chrysenyl group, a perylenyl group, a pentaphenyl group, a hexacenyl group, a pentacenyl group, a thiophenyl group, a furanyl group, a carbazolyl group, an indolyl group, an isoindolyl group, a benzofuranyl group, a benzothiophenyl group, a dibenzofuranyl group, a dibenzothiophenyl group, a benzocarbazolyl group, a dibenzocarbazolyl group, a dibenzosilolyl group, a pyridinyl group, and —Si($Q_{31}$)($Q_{32}$)($Q_{33}$), and $Q_{31}$ to $Q_{33}$ may each independently selected from a $C_1$-$C_{10}$ alkyl group, a $C_1$-$C_{10}$ alkoxy group, a phenyl group, a biphenyl group, a terphenyl group, and a naphthyl group.

In one or more embodiments, xd4 in Formula 501 may be 2, but embodiments of the present disclosure are not limited thereto.

For example, the fluorescent dopant may be selected from Compounds FD1 to FD22:
FD1
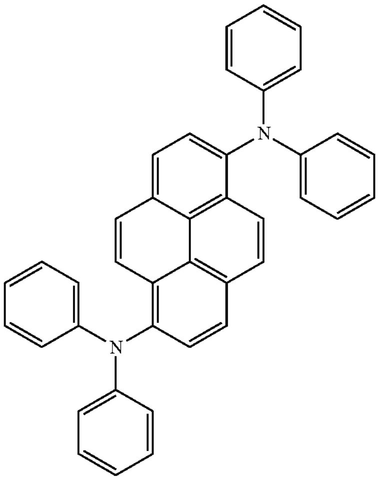
FD2
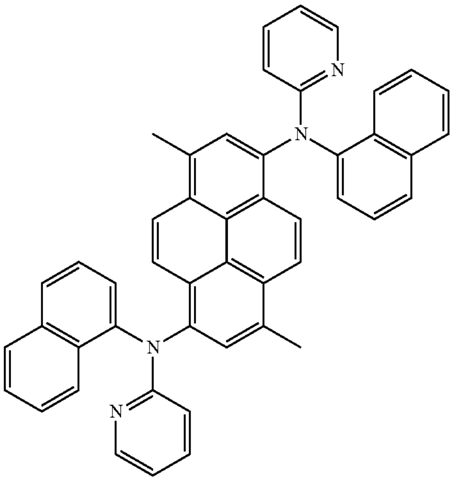
FD3
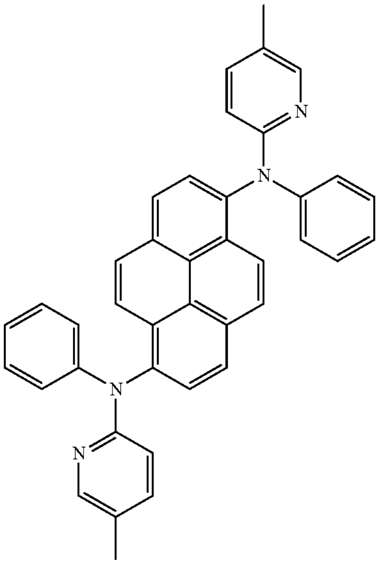
-continued
FD4
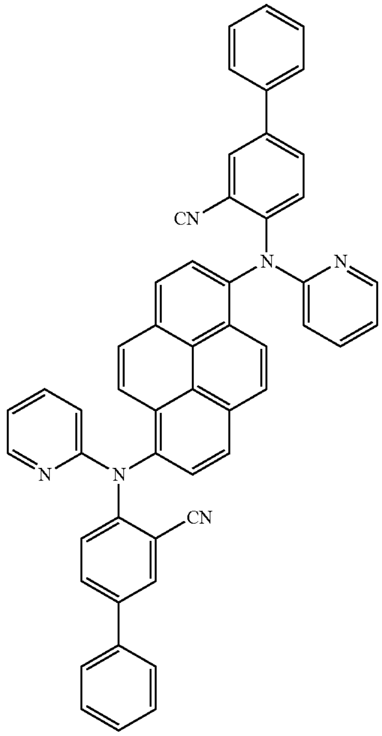
FD5
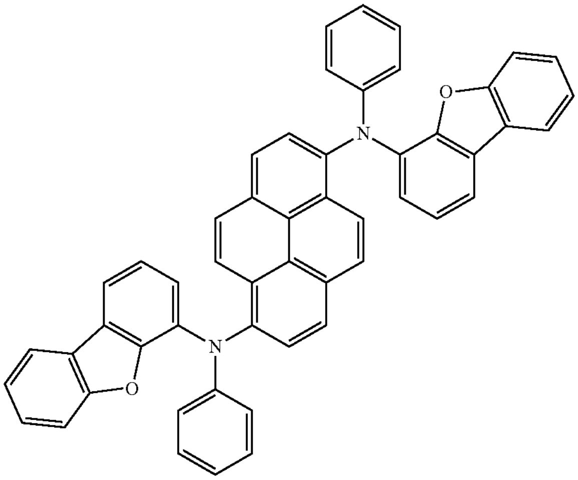

-continued
FD6
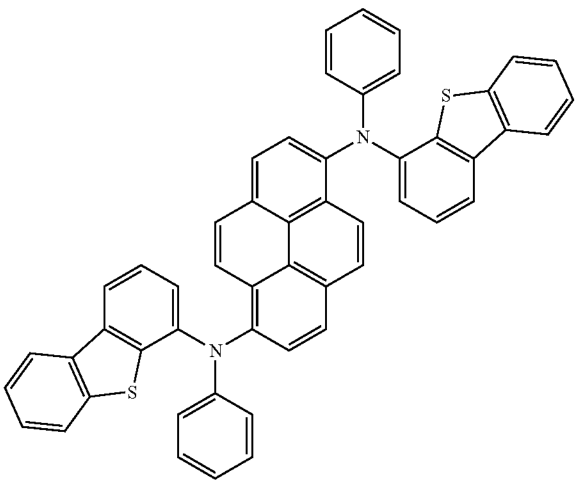
FD7
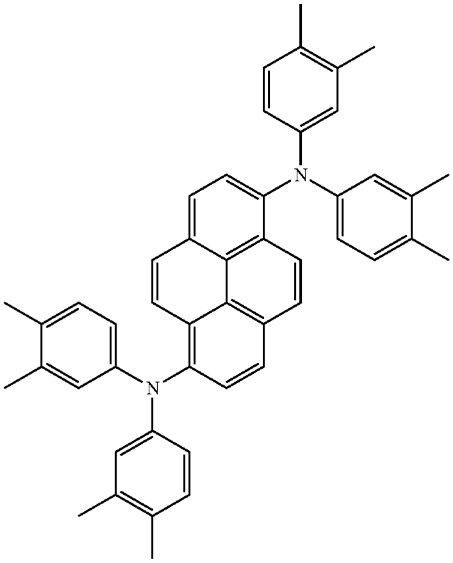
FD8
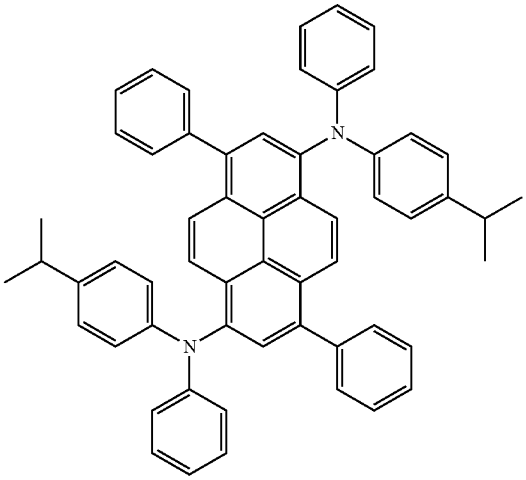
-continued
FD9
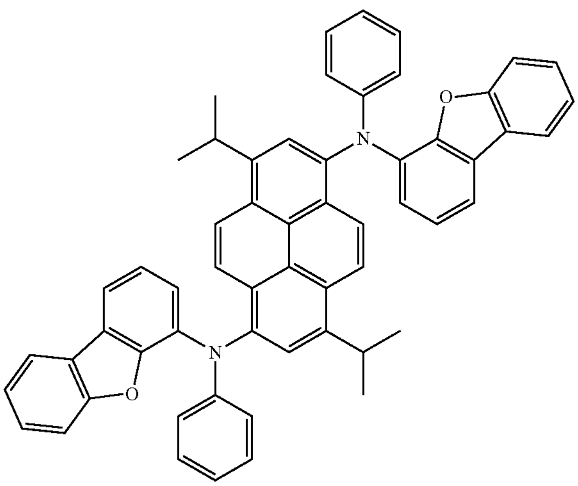
FD10
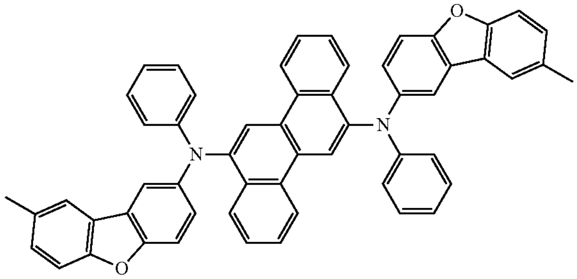
FD11
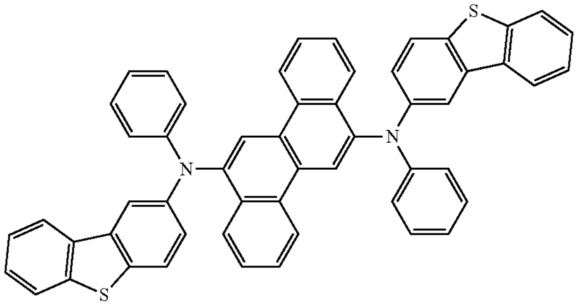
FD12
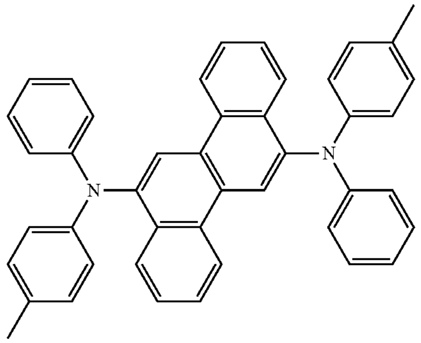

-continued
FD13
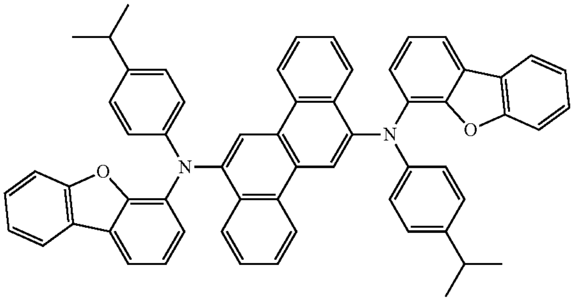
FD14
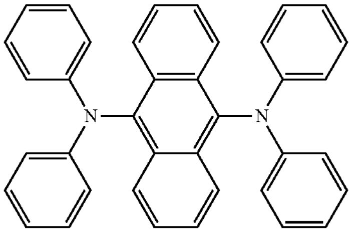
FD15
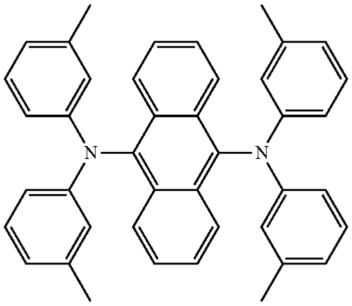
FD16
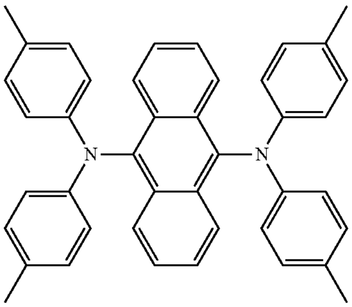
-continued
FD17
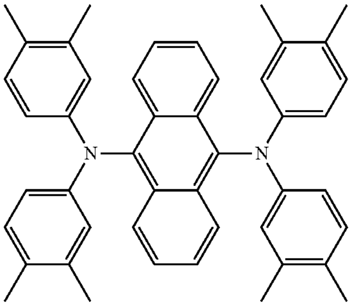
FD18
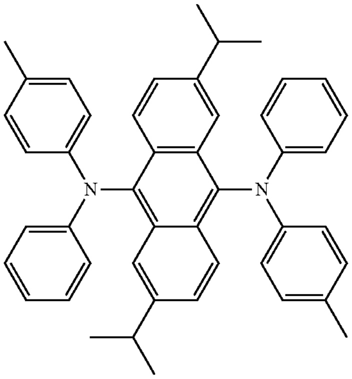
FD19
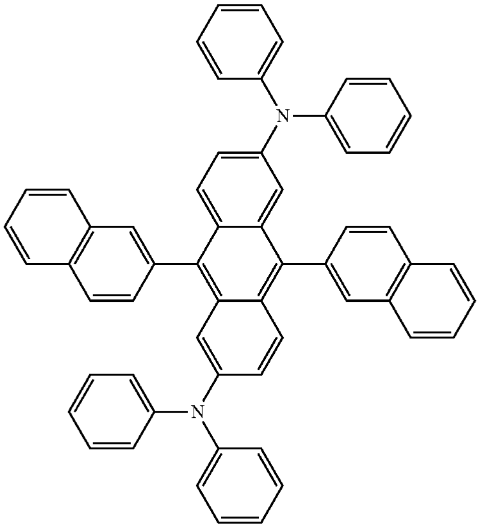
FD20
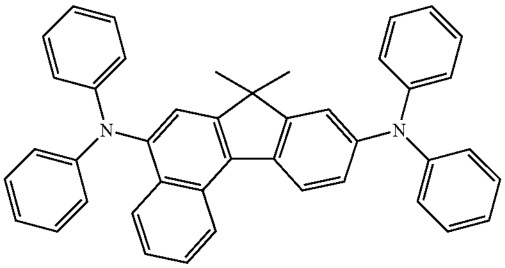

-continued
FD21
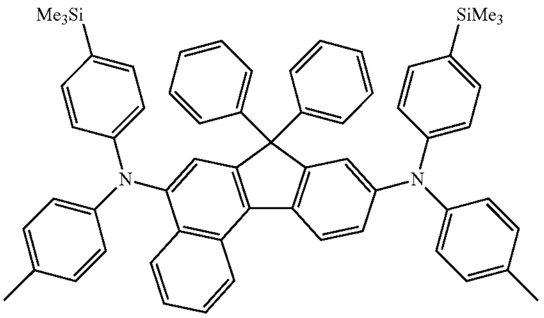
-continued
FD22
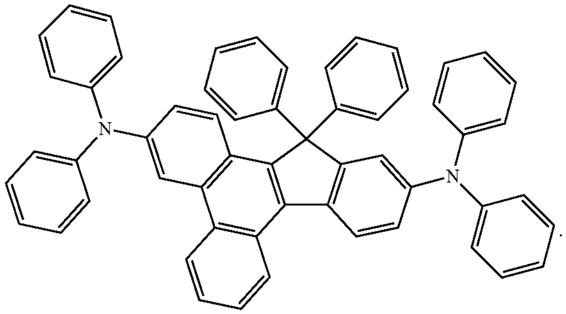
In one or more embodiments, the fluorescent dopant may be selected from the following compounds, but embodiments of the present disclosure are not limited thereto:
DPVBi
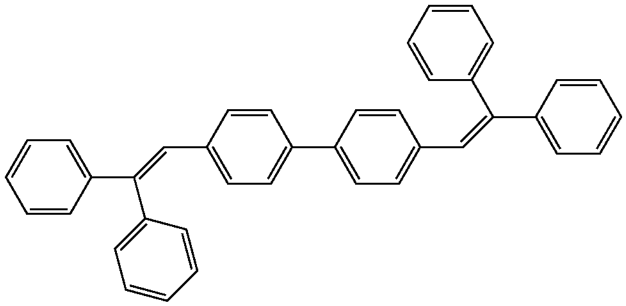
DPAVBi
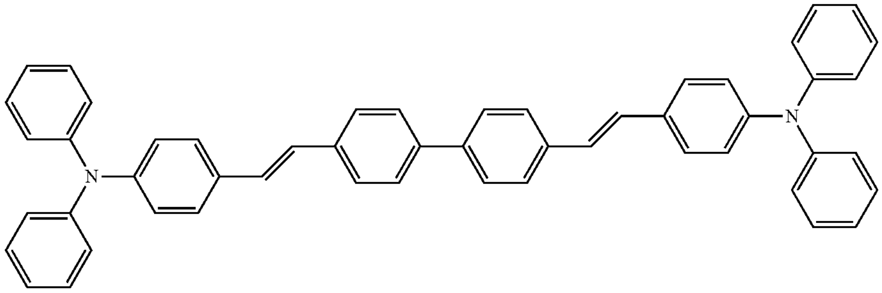
TBPe
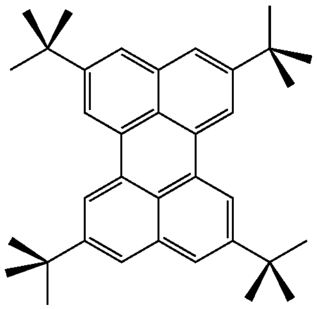
DCM
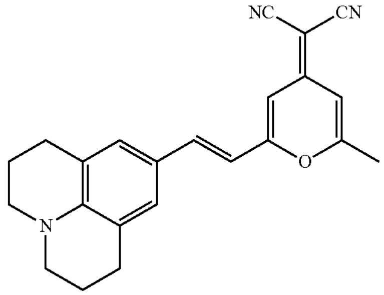

-continued

DCJTB

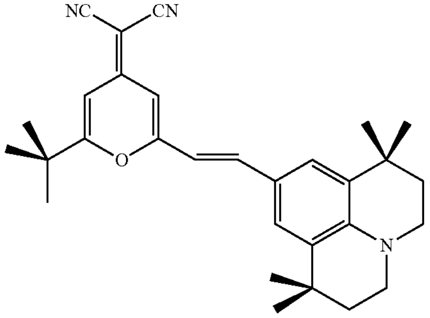

C545T

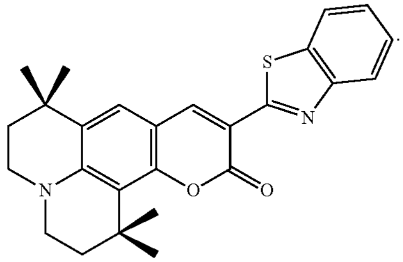

Coumarin 6

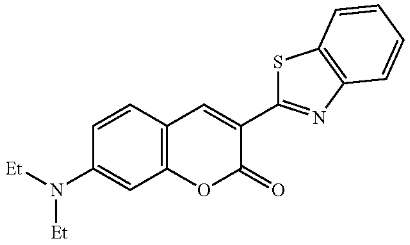

In one embodiment, the plurality of the light-emitting diodes may include at least one emission layer including an inorganic material, wherein the inorganic material may include a quantum confined semiconductor nanoparticle.

The plurality of the light-emitting diodes may each include a quantum confined semiconductor nanoparticle having a different particle diameter in each emission layer. Here, the particle diameter of the quantum confined semiconductor nanoparticle may be several nanometers to several hundred nanometers, for example, about 20 nm to about 900 nm.

The quantum confined semiconductor nanoparticles may be selected from compounds of Groups II-VI, compounds of Groups III-V, compounds of Groups IV-VI, elements of Group IV, compounds of Group IV, and any combination thereof, and an alloy of thereof. The alloy may include an alloy of the above-described compound and a transition metal.

The quantum confined semiconductor nanoparticle may have a core-shell structure including a core and a shell covering the core.

For example, the compounds of Groups II-VI may be selected from: dyad compounds selected from CdO, CdS, CdSe, CdTe, ZnO, ZnS, ZnSe, ZnTe, HgS, HgSe, HgTe, MgSe, MgS, and any combination thereof; triad compounds selected from CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, and any combination thereof; and tetrad compounds selected from HgZnTeS, CdZnSeS, CdZnSeTe, CdZnSTe, CdHgSeS, CdHgSeTe, CdHgSTe, HgZnSeS, HgZnSeTe and HgZnSTe, and any combination thereof, or alloys thereof.

For example, the compounds of Groups III-V may be selected from: dyad compounds selected from GaN, GaP, GaAs, AlN, AlP, AlAs, InN, InP, InAs, InSb, and any combination thereof; triad compounds selected from GaNP, GaNAs, GaNSb, GaPAs, GaPSb, AlNP, AlNAs, AlNSb, AlPAs, AlPSb, InNP, InNAs, InPAs, InPSb, GaAlNP, and any combination thereof; and tetrad compounds selected from GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, and any combination thereof, or alloys thereof.

For example, the compounds of Groups IV-VI may be selected from: dyad compounds selected from SnS, SnSe, SnTe, PbS, PbSe, PbTe, and any combination thereof; triad compounds selected from SnSeS, SnSeTe, SnSTe, PbSeS, PbSeTe, PbSTe, SnPbS, SnPbSe, SnPbTe, and any combination thereof, and tetrad compounds selected from SnPbSSe, SnPbSeTe, SnPbSTe, and any combination thereof, or alloys thereof.

For example, the element of Group IV may be selected from Si, Ge, and any combination thereof.

For example, the compound of Group IV may be selected from diad compounds selected from SiC, SiGe, and any combination thereof, or alloys thereof.

Here, the dyad compound, the triad compound, or the tetrad compound may be present in the particle at an even concentration, or may be divided into partially different states in the same particle according to the concentration distribution. In addition, the quantum confined semiconductor nanoparticle may have a core/shell structure in which one quantum confined semiconductor nanoparticles is surrounded by other quantum confined semiconductor nanoparticles. An interface between the core and the shell may have a concentration gradient in which the concentration of the element in the shell becomes lower toward the center of the particle.

The core may include at least one compound selected from CdS, CdSe, ZnS, ZnSe, ZnTe, HgS, HgSe, HgTe, CdTe, CdSeS, CdSeTe, CdZnS, CdZnSe, GaN, GaP, GaAs, GaInP, GaInN, InP, InAs, InZnP, and ZnO, or an alloy thereof.

The shell may include at least one compound selected from CdS, CdSe, ZnSe, ZnSeS, ZnS, ZnTe, CdTe, CdO, ZnO, InP, GaN, GaP, GaInP, GaInN, HgS, and HgSe, or an alloy thereof.

In one or more embodiments, the plurality of the light-emitting diodes may include at least one emission layer including an inorganic material, and the inorganic material may include a perovskite compound represented by Formula 3:

$$[A][B][X]_3. \qquad \text{Formula 3}$$

In Formula 3,

A may be at least one monovalent organic-cation, monovalent inorganic-cation, or any combination thereof, B may be at least one divalent inorganic-cation, and X may be at least one monovalent anion.

In Formula 1, A may be at least one monovalent organic-cation, monovalent inorganic-cation, or any combination thereof. For example, A may be i) at least one monovalent organic-cation, ii) at least one monovalent inorganic-cation, iii) at least two monovalent organic-cations that are different from each other, iv) at least two monovalent inorganic-cations that are different from each other, or v) a combination of at least one monovalent organic-cation and at least one monovalent inorganic-cation.

In one embodiment, A may be $(R_1R_2R_3C)^+$, $(R_1R_2R_3R_4N)^+$, $(R_1R_2R_3R_4P)^+$, $(R_1R_2R_3R_4As)^+$, $(R_1R_2R_3R_4Sb)^+$, $(R_1R_2N{=}C(R_3){-}NR_4R_5)^+$, a substituted or unsubstituted cycloheptatrienium, a substituted or unsubstituted nitrogen-containing 5-membered monovalent cation, a substituted or unsubstituted nitrogen-containing 6-membered monovalent cation, $Li^+$, $Na^+$, $K^+$, $Rb^+$, $Cs^+$, $Fr^+$, or any combination thereof, $R_1$ to $R_5$ may each independently be selected from hydrogen, deuterium, —F, —Cl, —Br, —I, a hydroxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_6$-$C_{60}$ aryl group, and $—N(Q_1)(Q_2)$, at least one substituent of the substituted cycloheptatrienium, the substituted nitrogen-containing 5-membered monovalent cation, and the substituted nitrogen-containing 6-membered monovalent cation each independently may be selected from deuterium, —F, —Cl, —Br, —I, a hydroxyl group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_6$-$C_{60}$ aryl group, and $—N(Q_3)(Q_4)$, and $Q_1$ to $Q_4$ may each independently be selected from hydrogen, deuterium, a hydroxyl group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_6$-$C_{60}$ aryl group.

The terms "nitrogen-containing 5-membered" and "nitrogen-containing 6-membered" each refer to an organic cyclic group including, as a ring-constituting atom, at least one N and at least one C.

For example, the "nitrogen-containing 5-membered ring" may be an imidazole, a pyrazole, a thiazole, an oxazole, a pyrrolidine, a pyrroline, a pyrrole, or a triazolyl, and the "nitrogen-containing 6-membered ring" may be a pyridine, a pyridazine, a pyrimidine, a pyrazine, or a piperidine, but embodiments of the present disclosure are not limited thereto.

For example, A in Formula 1 may be $(R_1R_2R_3C)^+$, $(R_1R_2R_3R_4N)^+$, $(R_1R_2R_3R_4P)^+$, $(R_1R_2R_3R_4As)^+$, $(R_1R_2R_3R_4Sb)^+$, $(R_1R_2N{=}C(R_3){-}NR_4R_5)^+$, a substituted or unsubstituted cycloheptatrienium, a substituted or unsubstituted imidazolium, a substituted or unsubstituted pyridinium, a substituted or unsubstituted pyridazinium, a substituted or unsubstituted pyrimidinium, a substituted or unsubstituted pyrazinium, a substituted or unsubstituted pyrazolium, a substituted or unsubstituted thiazolium, a substituted or unsubstituted oxazolium, a substituted or unsubstituted piperidinium, a substituted or unsubstituted pyrrolidinium, a substituted or unsubstituted pyrrolinium, a substituted or unsubstituted pyrrolium, a substituted or unsubstituted triazolium, $Li^+$, $Na^+$, $K^+$, $Rb^+$, $Cs^+$, $Fr^+$, or any combination thereof, $R_1$ to $R_5$ may each independently be selected from:

hydrogen, deuterium, —F, —Cl, —Br, —I, a hydroxyl group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, and a hydroxyl group;

a phenyl group, a naphthyl group, a biphenyl group, and a terphenyl group;

a phenyl group, a naphthyl group, a biphenyl group, and a terphenyl group, each substituted with at least one selected from deuterium, —F, —Cl, —Br, —I, a hydroxyl group, a $C_1$-$C_{20}$ alkyl group, and a $C_1$-$C_{20}$ alkoxy group; and $—N(Q_1)(Q_2)$, at least one substituent of the substituted cycloheptatrienium, the substituted imidazolium, the substituted pyridinium, the substituted pyridazinium, the substituted pyrimidinium, the substituted pyrazinium, the substituted pyrazolium, the substituted thiazolium, the substituted oxazolium, the substituted piperidinium, the substituted pyrrolidinium, the substituted pyrrolium, the substituted pyrrolium, and the substituted triazolium may each independently be selected from:

deuterium, —F, —Cl, —Br, —I, a hydroxyl group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, and a hydroxyl group;

a phenyl group, a naphthyl group, a biphenyl group, and a terphenyl group;

a phenyl group, a naphthyl group, a biphenyl group, and a terphenyl group, each substituted with at least one selected from deuterium, —F, —Cl, —Br, —I, a hydroxyl group, a $C_1$-$C_{20}$ alkyl group, and a $C_1$-$C_{20}$ alkoxy group; and $—N(Q_3)(Q_4)$, and $Q_1$ to $Q_4$ may each independently be selected from hydrogen, deuterium, a hydroxyl group, a $C_1$-$C_{20}$ alkyl group, a $C_1$-$C_{20}$ alkoxy group, a phenyl group, a naphthyl group, a biphenyl group, and a terphenyl group.

In one embodiment, A in Formula 1 may be $(R_1R_2R_3R_4N)^+$, $(R_1R_2R_3R_4P)^+$, $(R_1R_2R_3R_4As)^+$, $(R_1R_2R_3R_4Sb)^+$, $Li^+$, $Na^+$, $K^+$, $Rb^+$, $Cs^+$, $Fr^+$, or any combination thereof, $R_1$ to $R_4$ may each independently be selected from hydrogen, deuterium, —F, —Cl, —Br, —I, a hydroxyl group, a $C_1$-$C_{20}$ alkyl group, a $C_1$-$C_{20}$ alkoxy group, and $—N(Q_1)(Q_2)$, and $Q_1$ and $Q_2$ may each independently be selected from hydrogen, deuterium, a hydroxyl group, a $C_1$-$C_{20}$ alkyl group, and a $C_1$-$C_{20}$ alkoxy group.

In one or more embodiments, A in Formula 1 may be $(R_1R_2R_3R_4N)^+$, $K^+$, $Rb^+$, $Cs^+$, or any combination thereof, $R_1$ to $R_4$ may each independently be selected from hydrogen, deuterium, —F, —Cl, —Br, —I, a hydroxyl group, a $C_1$-$C_{20}$ alkyl group, a $C_1$-$C_{20}$ alkoxy group, and $—N(Q_1)(Q_2)$, and $Q_1$ and $Q_2$ may each independently be selected from hydrogen, deuterium, a hydroxyl group, a $C_1$-$C_{20}$ alkyl group, and a $C_1$-$C_{20}$ alkoxy group.

In one or more embodiments, A in Formula 1 may be $(NH_4)^+$, $(PH_4)^+$, $(AsH_4)^+$, $(SbH_4)^+$, $(NF_4)^+$, $(PF_4)^+$, $(NCl_4)^+$, $(PCl_4)^+$, $(CH_3NH_3)^+$, $(CH_3PH_3)^+$, $(CH_3AsH_3)^+$, $(CH_3SbH_3)^+$, $((CH_3)_2NH_2)^+$, $((CH_3)_2PH_2)^+$, $((CH_3)_2AsH_2)^+$, $((CH_3)_2SbH_2)^+$, $((CH_3)_3NH)^+$, $((CH_3)_3PH)^+$, $((CH_3)_3AsH)^+$, $((CH_3)_3SbH)^+$, $((CH_3CH_2)NH_3)^+$, $((CH_3CH_2)PH_3)^+$, $((CH_3CH_2)AsH_3)^+$, $((CH_3CH_2)SbH_3)^+$, $(CH_2N_2H_4)^+$, $(C_7H_7)^+$, $(NH_3OH)^+$, $(NH_3NH_2)^+$, $((CH_2)_3NH_2)^+$, $(CH(NH_2)_2)^+$, $(C_3N_2H_5)^+$, $(NC_4H_8)^+$, $((NH_2)_3C)^+$, $K^+$, $Rb^+$, $Cs^+$, or any combination thereof, but embodiments of the present disclosure are not limited thereto.

In Formula 1, B may be at least one divalent inorganic-cation. For example, B may be i) at least one divalent inorganic-cation, or ii) at least two divalent inorganic-cations that are different from each other.

In one embodiment, B in Formula 1 may include a divalent cation of a rare earth metal, a divalent cation of an alkaline earth metal, a divalent cation of a transition metal, a divalent cation of a post-transition metal, or any combination thereof. For example, B in Formula 1 may include $La^{2+}$, $Ce^{2+}$, $Pr^{2+}$, $Nd^{2+}$, $Pm^{2+}$, $Eu^{2+}$, $Gd^{2+}$, $Tb^{2+}$, $Ho^{2+}$, $Er^{2+}$, $Tm^{2+}$, $Yb^{2+}$, $Lu^{2+}$, $Be^{2+}$, $Mg^{2+}$, $Ca^{2+}$, $Sr^{2+}$, $Ba^{2+}$, $Ra^{2+}$, $Pb^{2+}$, $Sn^{2+}$, or any combination thereof.

In one embodiment, B in Formula 1 may include $Tm^{+2}$, $La^{2+}$, $Ce^{2+}$, $Pr^{2+}$, $Nd^{2+}$, $Pm^{2+}$, $Eu^{2+}$, $Gd^{2+}$, $Tb^{2+}$, $Ho^{2+}$, $Er^{2+}$, $Yb^{2+}$, $Lu^{2+}$, $Be^{2+}$, $Mg^{2+}$, $Ca^{2+}$, $Sr^{2+}$, $Ba^{2+}$, $Ra^{2+}$, $Pb^{2+}$, $Sn^{2+}$, or any combination thereof, but embodiments of the present disclosure are not limited thereto.

In Formula 1, X may be at least one monovalent cation. For example, X may be i) at least one monovalent anion, or ii) at least two monovalent anions that are different from each other.

In one embodiment, X in Formula 1 may include at least one halide anion (for example, —F, —Cl, —Br, or —I). For example, X in Formula 1 may be i) at least one halide anion, or ii) at least two halide anions that are different from each other.

In one or more embodiments, X in Formula 1 may be —I, but embodiments of the present disclosure are not limited thereto.

The perovskite compound may be selected from, for example, $[CH_3NH_3][Pb][I]_3$, $[CH_3NH_3][Pb_nSr_{(1-n)}][I]_3$, $[CH_3NH_3][Pb_nMg_{(1-n)}][I]_3$, $[CH_3NH_3][Pb_nCa_{(1-n)}][I]_3$, $[CH_3NH_3][Pb_nBa_{(1-n)}][I]_3$, $[CH_3NH_3][Pb_nEu_{(1-n)}][I]_3$, $[CH_3NH_3][Pb_nYb_{(1-n)}][I]_3$, $[CH_3NH_3][Pb_nTm_{(1-n)}][I]_3$, $[CH_3NH_3][Pb_nLa_{(1-n)}][I]_3$, $[CH_3NH_3][Pb_nCe_{(1-n)}][I]_3$, $[CH_3NH_3][Pb_nPr_{(1-n)}][I]_3$, $[CH_3NH_3][Pb_nNd_{(1-n)}][I]_3$, $[CH_3NH_3][Pb_nPm_{(1-n)}][I]_3$, $[CH_3NH_3][Pb_nGd_{(1-n)}][I]_3$, $[CH_3NH_3][Pb_nTb_{(1-n)}][I]_3$, $[CH_3NH_3][Pb_nHo_{(1-n)}][I]_3$, $[CH_3NH_3][Pb_nEr_{(1-n)}][I]_3$, $[Cs][Pb][I]_3$, $[Cs][Pb_nSr_{(1-n)}][I]_3$, $[Cs][Pb_nMg_{(1-n)}][I]_3$, $[Cs][Pb_nCa_{(1-n)}][I]_3$, $[Cs][Pb_nBa_{(1-n)}][I]_3$, $[Cs][Pb_nEu_{(1-n)}][I]_3$, $[Cs][Pb_nYb_{(1-n)}][I]_3$, $[Cs][Pb_nTm_{(1-n)}][I]_3$, $[Cs][Pb_nLa_{(1-n)}][I]_3$, $[Cs][Pb_nCe_{(1-n)}][I]_3$, $[Cs][Pb_nPr_{(1-n)}][I]_3$, $[Cs][Pb_nNd_{(1-n)}][I]_3$, $[Cs][Pb_nPm_{(1-n)}][I]_3$, $[Cs][Pb_nGd_{(1-n)}][I]_3$, $[Cs][Pb_nTb_{(1-n)}][I]_3$, $[Cs][Pb_nHo_{(1-n)}][I]_3$, $[Cs][Pb_nEr_{(1-n)}][I]_3$, $[Rb][Pb][I]_3$, $[Rb][Pb_nSr_{(1-n)}][I]_3$, $[Rb][Pb_nMg_{(1-n)}][I]_3$, $[Rb][Pb_nCa_{(1-n)}][I]_3$, $[Rb][Pb_nBa_{(1-n)}][I]_3$, $[Rb][Pb_nEu_{(1-n)}][I]_3$, $[Rb][Pb_nYb_{(1-n)}][I]_3$, $[Rb][Pb_nTm_{(1-n)}][I]_3$, $[Rb][Pb_nLa_{(1-n)}][I]_3$, $[Rb][Pb_nCe_{(1-n)}][I]_3$, $[Rb][Pb_nPr_{(1-n)}][I]_3$, $[Rb][Pb_nNd_{(1-n)}][I]_3$, $[Rb][Pb_nPm_{(1-n)}][I]_3$, $[Rb][Pb_nGd_{(1-n)}][I]_3$, $[Rb][Pb_nTb_{(1-n)}][I]_3$, $[Rb][Pb_nHo_{(1-n)}][I]_3$, $[Rb][Pb_nEr_{(1-n)}][I]_3$, $[K][Pb][I]_3$, $[K][Pb_nSr_{(1-n)}][I]_3$, $[K][Pb_nMg_{(1-n)}][I]_3$, $[K][Pb_nCa_{(1-n)}][I]_3$, $[K][Pb_nBa_{(1-n)}][I]_3$, $[K][Pb_nEu_{(1-n)}][I]_3$, $[K][Pb_nYb_{(1-n)}][I]_3$, $[K][Pb_nTm_{(1-n)}][I]_3$, $[K][Pb_nLa_{(1-n)}][I]_3$, $[K][Pb_nCe_{(1-n)}][I]_3$, $[K][Pb_nPr_{(1-n)}][I]_3$, $[K][Pb_nNd_{(1-n)}][I]_3$, $[K][Pb_nPm_{(1-n)}][I]_3$, $[K][Pb_nGd_{(1-n)}][I]_3$, $[K][Pb_nTb_{(1-n)}][I]_3$, $[K][Pb_nHo_{(1-n)}][I]_3$, $[K][Pb_nEr_{(1-n)}][I]_3$, $[CH_3NH_3][Tm][I]_3$, $[CH_3NH_3][Tm_nSr_{(1-n)}][I]_3$, $[CH_3NH_3][Tm_nMg_{(1-n)}][I]_3$, $[CH_3NH_3][Tm_nCa_{(1-n)}][I]_3$, $[CH_3NH_3][Tm_nBa_{(1-n)}][I]_3$, $[CH_3NH_3][Tm_nEu_{(1-n)}][I]_3$, $[CH_3NH_3][Tm_nYb_{(1-n)}][I]_3$, $[CH_3NH_3][Tm_nLa_{(1-n)}][I]_3$, $[CH_3NH_3][Tm_nCe_{(1-n)}][I]_3$, $[CH_3NH_3][Tm_nPr_{(1-n)}][I]_3$, $[CH_3NH_3][Tm_nNd_{(1-n)}][I]_3$, $[CH_3NH_3][Tm_nPm_{(1-n)}][I]_3$, $[CH_3NH_3][Tm_nGd_{(1-n)}][I]_3$, $[CH_3NH_3][Tm_nTb_{(1-n)}][I]_3$, $[CH_3NH_3][Tm_nHo_{(1-n)}][I]_3$, $[CH_3NH_3][Tm_nEr_{(1-n)}][I]_3$, $[Cs][Tm][I]_3$, $[Cs][Tm_nSr_{(1-n)}][I]_3$, $[Cs][Tm_nMn_{(1-n)}][I]_3$, $[Cs][Tm_nCa_{(1-n)}][I]_3$, $[Cs][Tm_nBa_{(1-n)}][I]_3$, $[Cs][Tm_nEu_{(1-n)}][I]_3$, $[Cs][Tm_nYb_{(1-n)}][I]_3$, $[Cs][Tm_nLa_{(1-n)}][I]_3$, $[Cs][Tm_nCe_{(1-n)}][I]_3$, $[Cs][Tm_nPr_{(1-n)}][I]_3$, $[Cs][TmnNd_{(1-n)}][I]_3$, $[Cs][Tm_nPm_{(1-n)}][I]_3$, $[Cs][Tm_nGd_{(1-n)}][I]_3$, $[Cs][Tm_nTb_{(1-n)}][I]_3$, $[Cs][Tm_nHo_{(1-n)}][I]_3$, $[Cs][Tm_nEr_{(1-n)}][I]_3$, and any combination thereof, wherein n is a real number satisfying $0<n<1$. Here, n may be, for example, a real number satisfying $0<n\leq 0.6$. In one embodiment, n may be a real number satisfying $0.001\leq n\leq 0.6$. In one or more embodiments, n may be a real number satisfying $0.05\leq n\leq 0.4$, but embodiments of the present disclosure are not limited thereto.

Following the formation of the second electrode 230, the plurality of the light-emitting diodes 200, each including the pixel electrodes 210R, 210G, and 210B, the intermediate layers 220R, 220G, and 220B, and the second electrode 230 may form the thin film encapsulation portion 300 to protect the plurality of the light-emitting diodes 200 from impurities such as external oxygen or moisture.

Each of the plurality of the Pas may be provided with at least one light-emitting diode, but embodiments of the present disclosure are not limited thereto. For example, one PA may be provided with at least two light-emitting diodes that are stacked each other.

The plurality of the light-emitting diodes (for example, at least two light-emitting diodes) may each independently emit light having a different wavelength, or the plurality of the light-emitting diodes may include a first light-emitting diode and a second light-emitting diode, wherein the second light-emitting diode absorbs incident light from the first light-emitting diode, thereby emitting light having a different wavelength from that of the incident light.

Here, the second light-emitting diode may be a light-emitting diode including the quantum confined semiconductor nanoparticle or the perovskite compound, but embodiments of the present disclosure are not limited thereto.

The thin film encapsulation portion 300 may extent to cover not only the top surface of the light-emitting diode 200, but also the side surfaces of the light-emitting diode 200, so as to be in contact with a portion of the substrate 100. Accordingly, the penetration of external oxygen and moisture into the light-emitting diode 200 may be effectively prevented or reduced.

The thin film encapsulation portion 300 may include the organic film including the cured product of the composition for forming the organic film, the composition including at least one UV-absorbing unit represented by one selected from Formulae 1-1 to 1-4.

The electronic apparatus according to an embodiment may be, for example, an organic light-emitting display apparatus including the organic light-emitting device. Such an organic light-emitting display apparatus may include a plurality of the organic light-emitting devices. Therefore, according to an embodiment, an organic light-emitting display device includes: a substrate, an organic light-emitting unit including a plurality of organic light-emitting devices on the substrate; and a thin film encapsulation portion on the organic light-emitting unit sealing the organic light-emitting unit, wherein the thin film encapsulation portion 300 includes a curable material and an UV absorber. The curable material and the UV absorber may respectively be defined the same as described above.

According to an aspect of embodiment of the present disclosure, there is provided a method of preparing an electronic apparatus, the method including:

providing a substrate with a pixel defined unit defining a pixel area and a non-pixel area;

providing the pixel area with a light-emitting diode; and providing a thin film encapsulation portion including an organic film and sealing the light-emitting diode and the pixel defined unit at the same (e.g., substantially the same) time, wherein the providing of the thin film encapsulation portion includes forming the organic film by providing and curing a thin-film sealing composition, so as to cover the light-emitting diode and the pixel defined unit at the same (e.g., substantially the same) time, wherein the thin-film sealing composition includes at least one UV absorber.

The substrate may be any suitable substrate available in the art for an organic light-emitting display device, and may be an inorganic substrate or an organic substrate, each having excellent mechanical strength, thermal stability, transparency, surface smoothness, ease of handling, and water resistance.

For example, the substrate may be an inorganic substrate made of a transparent glass material containing $SiO_2$ as a main component, but embodiments of the present disclosure are not limited thereto.

For example, may be an organic substrate having an insulating property. An organic material having an insulating property may be, for example, selected from PES, PAR, PEI, PEN, PET, PPS, polyallylate, polyimide, PC, TAC, and CAP, but embodiments of the present disclosure are not limited thereto.

The providing of the substrate with the pixel defined unit defining a pixel area and a non-pixel area may be performed by a photolithography method.

For example, the pixel defined unit may be formed by coating the substrate with a photosensitive material, optionally exposing a pixel area to light by using a photomask exposing a pixel area, and removing the pixel area.

The providing of the thin film encapsulation portion including the organic film may include irradiating light having a wavelength between about 360 nm and about 470 nm. Here, the light may have an exposure amount of about 3,000 mJ, for example, about 1,000 mJ.

According to another aspect of an embodiment of the present disclosure, there is provided a method of preparing an electronic apparatus, the method including:

forming an organic light-emitting device on a substrate, the organic light-emitting device including an emission layer; and forming a thin film encapsulation portion sealing the organic light-emitting device formed on the substrate, the thin film encapsulation portion including an organic film, wherein the forming of the thin film encapsulation portion includes forming the organic film by providing and curing a composition for forming an organic film, so as to cover the organic light-emitting device, the emission layer includes an organometallic compound, the composition for forming the organic film includes a cured product thereof including a curable material and an UV absorber, and the curable material includes a (meth)acrylate compound.

In one embodiment, the forming of the organic film may include irradiating light having a maximum emission wavelength range between about 360 nm and about 470 nm.

The thin film encapsulation portion, the organic light-emitting device, the organometallic compound, the curable material, the UV absorber, and the organic film may respectively be defined in the same manner as described above.

When an electronic apparatus is prepared according to the method described above, UV light entering from the outside may reach the organic light-emitting device, and accordingly, the deterioration of the organometallic compound included in the emission layer may be blocked, thereby preventing or reducing damage that may be caused by continuous exposure of the organic light-emitting device to UV light. Accordingly, the organic light-emitting device and the electronic apparatus including the same may have improved durability.

The term "$C_1$-$C_{60}$ alkyl group," as used herein, refers to a linear or branched aliphatic saturated hydrocarbon monovalent group having 1 to 60 carbon atoms, and examples thereof include a methyl group, an ethyl group, a propyl group, an isobutyl group, a sec-butyl group, a tert-butyl group, a pentyl group, an isoamyl group, and a hexyl group. The term "$C_1$-$C_{60}$ alkylene group," as used herein, refers to a divalent group having substantially the same structure as the $C_1$-$C_{60}$ alkyl group.

The term "$C_2$-$C_{60}$ alkenyl group," as used herein, refers to a hydrocarbon group having at least one carbon-carbon double bond at a main chain (e.g., in the middle) or at a terminus of the $C_2$-$C_{60}$ alkyl group, and examples thereof include an ethenyl group, a propenyl group, and a butenyl group. The term "$C_2$-$C_{60}$ alkenylene group," as used herein, refers to a divalent group having substantially the same structure as the $C_2$-$C_{60}$ alkenyl group.

The term "$C_2$-$C_{60}$ alkynyl group," as used herein, refers to a hydrocarbon group having at least one carbon-carbon triple bond at a main chain (e.g., in the middle) or at a terminus of the $C_2$-$C_{60}$ alkyl group, and examples thereof include an ethynyl group, and a propynyl group. The term "$C_2$-$C_{60}$ alkynylene group," as used herein, refers to a divalent group having substantially the same structure as the $C_2$-$C_{60}$ alkynyl group.

The term "$C_1$-$C_{60}$ alkoxy group," as used herein, refers to a monovalent group represented by —$OA_{101}$ (wherein $A_{101}$ is the $C_1$-$C_{60}$ alkyl group), and examples thereof include a methoxy group, an ethoxy group, and an isopropyloxy group.

The term "$C_3$-$C_{10}$ cycloalkyl group," as used herein, refers to a monovalent saturated hydrocarbon monocyclic group having 3 to 10 carbon atoms, and examples thereof include a cyclopropyl group, a cyclobutyl group, a cyclopentyl group, a cyclohexyl group, and a cycloheptyl group. The term "$C_3$-$C_{10}$ cycloalkylene group," as used herein, refers to a divalent group having substantially the same structure as the $C_3$-$C_{10}$ cycloalkyl group.

The term "$C_1$-$C_{10}$ heterocycloalkyl group," as used herein, refers to a monovalent monocyclic group having at least one heteroatom selected from N, O, Si, P, and S as a ring-forming atom and 1 to 10 carbon atoms, and examples thereof include a 1,2,3,4-oxatriazolidinyl group, a tetrahydrofuranyl group, and a tetrahydrothiophenyl group. The term "$C_1$-$C_{10}$ heterocycloalkylene group," as used herein, refers to a divalent group having substantially the same structure as the $C_1$-$C_{10}$ heterocycloalkyl group.

The term "$C_3$-$C_{10}$ cycloalkenyl group," as used herein, refers to a monovalent monocyclic group that has 3 to 10 carbon atoms and at least one carbon-carbon double bond in the ring thereof and no aromaticity (e.g., the group and/or molecule is not aromatic), and examples thereof include a cyclopentenyl group, a cyclohexenyl group, and a cycloheptenyl group. The term "$C_3$-$C_{10}$ cycloalkenylene group," as used herein, refers to a divalent group having substantially the same structure as the $C_3$-$C_{10}$ cycloalkenyl group.

The term "$C_1$-$C_{10}$ heterocycloalkenyl group," as used herein, refers to a monovalent monocyclic group that has at least one heteroatom selected from N, O, Si, P, and S as a ring-forming atom, 1 to 10 carbon atoms, and at least one carbon-carbon double bond in its ring. Non-limiting examples of the $C_1$-$C_{10}$ heterocycloalkenyl group include a 4,5-dihydro-1,2,3,4-oxatriazolylgroup, a 2,3-dihydrofuranyl group, and a 2,3-dihydrothiophenyl group. The term "$C_1$-$C_{10}$ heterocycloalkenylene group," as used herein, refers to a divalent group having substantially the same structure as the $C_1$-$C_{10}$ heterocycloalkenyl group.

The term "$C_6$-$C_{60}$ aryl group," as used herein, refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other (e.g., combined together).

The term "$C_1$-$C_{60}$ heteroaryl group," as used herein, refers to a monovalent group having a carbocyclic aromatic system that has at least one heteroatom selected from N, O, Si, P, and S as a ring-forming atom, in addition to 1 to 60 carbon atoms. The term "$C_1$-$C_{60}$ heteroarylene group," as used herein, refers to a divalent group having a carbocyclic aromatic system that has at least one heteroatom selected from N, O, Si, P, and S as a ring-forming atom, in addition to 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be condensed with each other (e.g., combined together).

The term "$C_6$-$C_{60}$ aryloxy group," as used herein, refers to —$OA_{102}$ (wherein $A_{102}$ is the $C_6$-$C_{60}$ aryl group), and the term "$C_6$-$C_{60}$ arylthio group," as used herein, indicates —$SA_{103}$ (wherein $A_{103}$ is the $C_6$-$C_{60}$ aryl group).

The term "monovalent non-aromatic condensed polycyclic group," as used herein, refers to a monovalent group (for example, having 8 to 60 carbon atoms) having two or more rings condensed with each other (e.g., combined together), only carbon atoms as ring-forming atoms, and no aromaticity in its entire molecular structure (e.g., the entire molecule is not aromatic). An example of the monovalent non-aromatic condensed polycyclic group is a fluorenyl group. The term "divalent non-aromatic condensed polycyclic group," as used herein, refers to a divalent group having substantially the same structure as the monovalent non-aromatic condensed polycyclic group.

The term "monovalent non-aromatic condensed heteropolycyclic group," as used herein, refers to a monovalent group (for example, having 1 to 60 carbon atoms) having two or more rings condensed to each other (e.g., combined together), at least one heteroatom selected from N, O, Si, P, and S, other than carbon atoms, as a ring-forming atom, and no aromaticity in its entire molecular structure (e.g., the entire molecule is not aromatic). An example of the monovalent non-aromatic condensed heteropolycyclic group is a carbazolyl group. The term "divalent non-aromatic condensed heteropolycyclic group," as used herein, refers to a divalent group having substantially the same structure as the monovalent non-aromatic condensed heteropolycyclic group.

The term "$C_5$-$C_{60}$ carbocyclic group," as used herein, refers to a monocyclic or polycyclic group having 5 to 60 carbon atoms in which a ring-forming atom is a carbon atom only. The $C_5$-$C_{60}$ carbocyclic group may be an aromatic carbocyclic group or a non-aromatic carbocyclic group. The $C_5$-$C_{60}$ carbocyclic group may be a ring, such as benzene, a monovalent group, such as a phenyl group, or a divalent group, such as a phenylene group. In one or more embodiments, depending on the number of substituents connected to the $C_5$-$C_{60}$ carbocyclic group, the $C_5$-$C_{60}$ carbocyclic group may be a trivalent group or a quadrivalent group.

The term "$C_1$-$C_{60}$ heterocyclic group," as used herein, refers to a group having substantially the same structure as the $C_1$-$C_{60}$ carbocyclic group, except that as a ring-forming atom, at least one heteroatom selected from N, O, Si, P, and S is used in addition to carbon (the number of carbon atoms may be in a range of 1 to 60).

At least one substituent of the substituted $C_5$-$C_{60}$ carbocyclic group, the substituted $C_1$-$C_{60}$ heterocyclic group, the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{60}$ cyclo alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group;

a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_3$-$C_{60}$ cyclo alkoxy group, each substituted with at least one selected from deuterium, —F, —Cl, —Br, —I, a hydroxyl group, a cyano group, a nitro group, an amidino group, a hydrazino group, a hydrazono group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{11})(Q_{12})$, —$B(Q_{11})(Q_{12})$, —$C(=O)(Q_{11})$, —$S(=O)_2(Q_{11})$, and —$P(=O)(Q_{11})(Q_{12})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{21})(Q_{22})$, —$B(Q_{21})(Q_{22})$, —$C(=O)(Q_{21})$, —$S(=O)_2(Q_{21})$, and —$P(=O)(Q_{21})(Q_{22})$; and —$Si(Q_{31})(Q_{32})(Q_{33})$, —$N(Q_{31})(Q_{32})$, —$B(Q_{31})(Q_{32})$, —$C(=O)(Q_{31})$, —$S(=O)_2(Q_{31})$, and —$P(=O)(Q_{31})(Q_{32})$, and $Q_{11}$ to $Q_{13}$, $Q_{21}$ to $Q_{23}$, and $Q_{31}$ to $Q_{33}$ may each independently be selected from hydrogen, deuterium, —F, —Cl, —Br, —I, a hydroxyl group, a cyano group, a nitro group, an amidino group, a hydrazino group, a hydrazono group, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{60}$ cyclo alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, and a terphenyl group.

The term "Ph," as used herein, refers to a phenyl group, the term "Me," as used herein, refers to a methyl group, the term "Et," as used herein, refers to an ethyl group, the term "ter-Bu" or "$Bu^t$," as used herein, refers to a tert-butyl group, and the term "OMe," as used herein, refers to a methoxy group.

The term "biphenyl group," as used herein, refers to "a phenyl group substituted with a phenyl group." In other words, the "biphenyl group" is a substituted phenyl group having a $C_6$-$C_{60}$ aryl group as a substituent.

The term "terphenyl group," as used herein, refers to "a phenyl group substituted with a biphenyl group." In other words, the "terphenyl group" is a phenyl group having, as a substituent, a $C_6$-$C_{60}$ aryl group substituted with a $C_6$-$C_{60}$ aryl group.

* and *' used herein, unless defined otherwise, each refer to a binding site to a neighboring atom in a corresponding formula.

Hereinafter, a compound according to embodiments and an organic light-emitting device according to embodiments will be described in more detail with reference to Synthesis Examples and Examples. The wording "B was used instead of A" used in describing Synthesis Examples refers to that an identical (e.g., substantially identical) molar equivalent of B was used in place of A.

EXAMPLES

Example 1-1

A composition for forming an organic film was prepared by using the compound and the amount shown in Table 1.

TABLE 1

| | Compound name | Used amount |
|---|---|---|
| UV absorber | 2-hydroxy benzotriazole | 0.03 mmol |
| Curable material | Lauryl actylate | 9 mmol |
| | Hexanediol dimethacrylate | 1 mmol |
| Initiator | Diphenyl(2,4,6-trimethylbenzoyl)phosphine oxide (TPO) | 0.03 mmol |

The organic film was applied to a glass substrate to form an organic film having a thickness of about 10 μm by using an ink jet film-forming device (Unijet facility, SG1024), and then, exposed to a light source having a wavelength of about 390 nm, to thereby cure the organic film.

Example 1-2

The composition for forming the organic film used in Example 1-1 was prepared, and then, was applied to a substrate provided with a pixel defined layer and a light-emitting diode to form an organic film having a thickness of about 10 μm by using an ink jet fill-forming device and the compound of Table 1. Then, the substrate was exposed to a light source having a wavelength of about 390 nm, to thereby prepare an electronic apparatus including a thin film encapsulation portion including the organic film.

Comparative Example 1-1

An organic film was formed in substantially the same manner as in Example 1-1, except that the UV absorber was not included in the composition for forming the organic film.

Comparative Example 1-2

An organic film was formed in substantially the same manner as in Example 1-2, except that the UV absorber was not included in the composition for forming the organic film.

Evaluation Example 1-1

Figure 3:
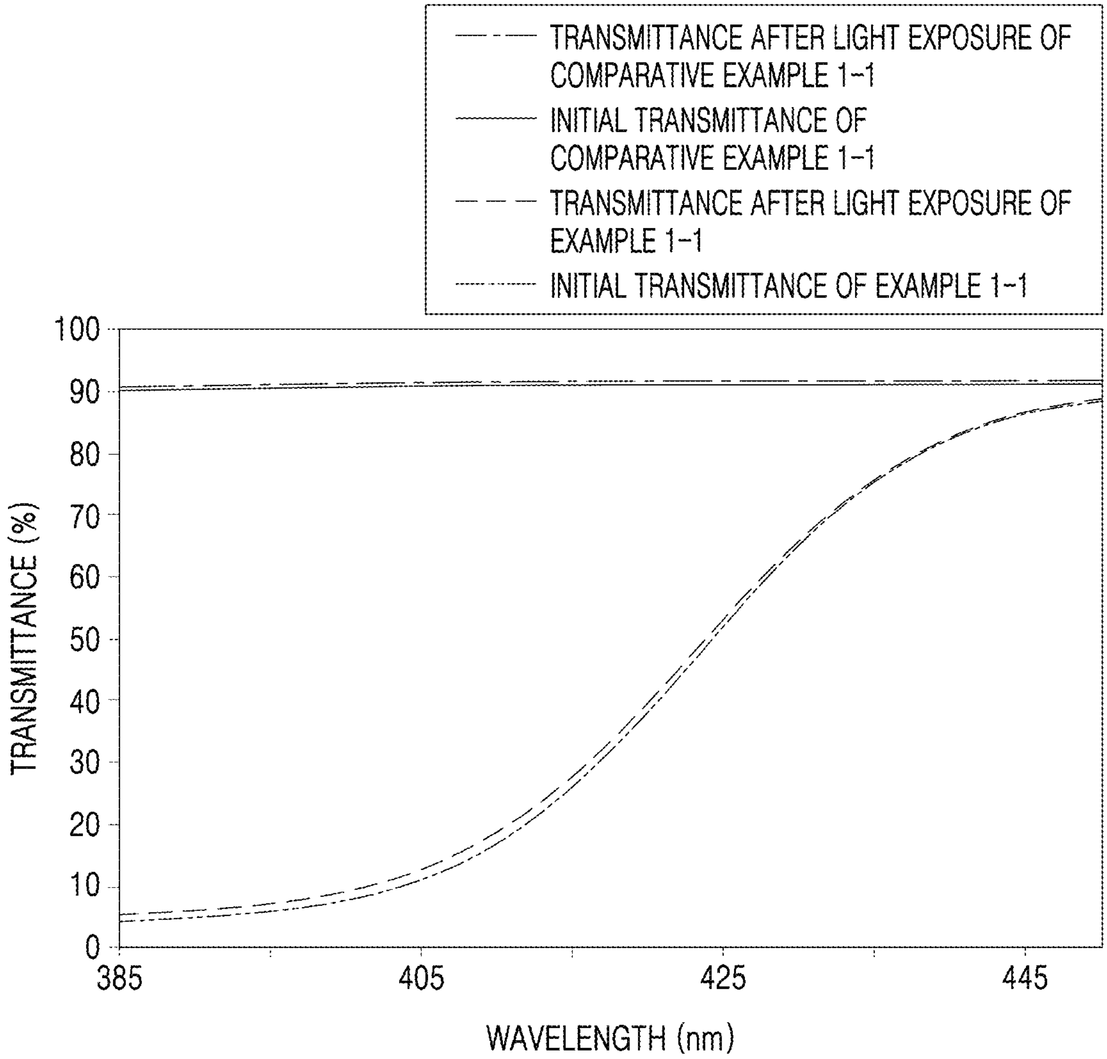
FIG. 3 is a graph showing initial transmittance and post-exposure transmittance of thin film encapsulation portions prepared according to Example 1-1 and Comparative Example 1-1, for light having a wavelength range between about 380 nm and about 400 nm.

The thin film encapsulation portions of Example 1-1 and Comparative Example 1-1 were subjected to measurement of exposed transmittance ("transmittance after light exposure) by using an initial transmittance photolithographic exposure device (ATLAS Company, Ci3000), and the results are shown in FIG. 3.

The photolithographic exposure device was equipped with a xenon Arc lamp, and the temperature inside a chamber was maintained at 40° C. during the exposure time. The exposure conditions include constant lamp intensity (340 nm 0.6 W/2) for 100 hours in total.

Referring to FIG. 3, it was confirmed that the initial average transmittance (5.0%) of the thin film encapsulation portion according to an embodiment at a wavelength range between about 380 nm and about 400 nm was about 18 times lower than that of the thin film encapsulation portion of Comparative Example 1-1 (90.6%), showing excellent UV blocking capability. After exposure to the UV lamp, the photocuring resistance was confirmed by increased amount of transmittance at a wavelength of about 405 nm. For example, at a wavelength of about 405 nm, the thin film encapsulation portion 300 of Example 1-1 showed the initial transmittance of about 11.0%, and the post-exposure transmittance of about 12.5%, and that is, the change in transmittance (a value obtained by subtracting the initial transmittance from the post-exposure transmittance) of about 1.5%. Meanwhile, at a wavelength of about 405 nm, the thin film encapsulation portion of Comparative Example 1-1 showed the initial transmittance of about 90.6% and the post-exposure transmittance of about 91.0%. Although the change in transmittance was small, there was no observable effect of blocking UV light.

Evaluation Example 1-2

Figure 4:
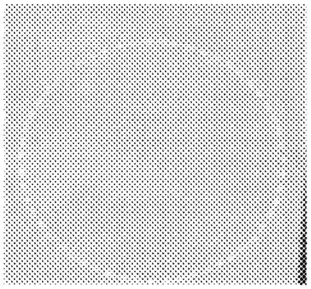
FIG. 4 is a series of images of lightened electronic apparatuses prepared according to Example 1-2 and Comparative Example 1-2 before and after light exposure.
Figure 4:
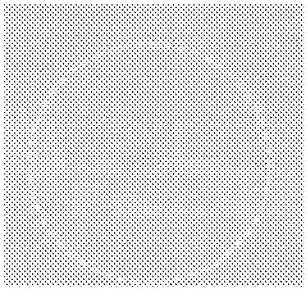
Figure 4:
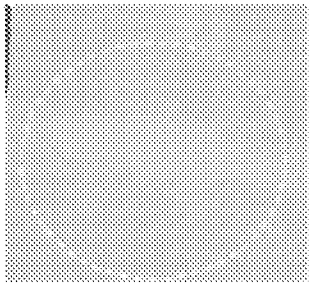
Figure 4:
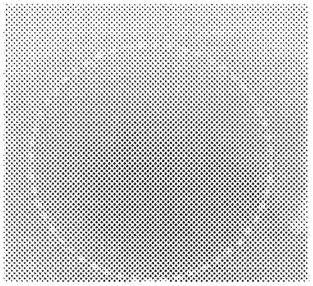

The electronic apparatuses of Example 1-2 and Comparative Example 1-2 were subjected to lightening, and then, measurement of the initial color temperature (Tc) and luminance (L). The same photolithographic exposure device used in Evaluation Example 1-1 was used for exposure, and the color temperature (Tc) and luminance (L) were measured. Then, changes in the color temperature (Tc) and luminance (L) were derived by comparing with the initial values, and the results are shown in Table 2 and FIG. 4.

TABLE 2

| | Example 1-2 | Comparative Example 1-2 |
|---|---|---|
| Changed amount in color temperature (ΔTc) | 30 K | 1500 K |
| Changed amount in luminance (ΔL) | 2% | −22% |

According to the results of Evaluation Example 2, the organic light-emitting display apparatus in which the thin film encapsulation portion includes the organic film including the UV absorber according to an embodiment was able to prevent the deterioration of a light-emitting device caused by outgassing of the pixel defined layer upon exposure to UV light.

Example 2-1

As curable materials, Compound 1-1 (lauryl acrylate) and Compound 1-2 (1,6-hexanediol dimethacrylate) were mixed at a volume ratio of about 9:1. Then, a composition for forming an organic film including 2-hydroxy benzotriazole a UV absorber was used to form a film having a thickness of about 10 μm by using an ink jet printing, followed by being cured, thereby forming an electronic apparatus including a thin-film seating unit sealing the organic light-emitting device on the substrate, the thin-film seating unit including the organic film. The mixture of Compounds 1-1 and 1-2 showed low viscosity of about 10 cP at room temperature (25° C.). Here, diphenyl(2,4,6-trimethylbenzoyl)phosphine oxide was used as a photoinitiator.

Compound 1-1

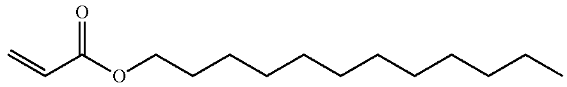

-continued

Compound 1-2

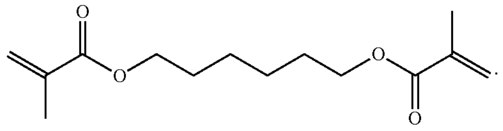

Comparative Example 2-1

As a curable material, an acryl-based polyethylene oxide having a molecular weight of about 1,000 or more and high viscosity of about 5,000 cP at room temperature was used. Then, a thin film encapsulation portion sealing the organic light-emitting device on the substrate was prepared in substantially the same manner as in Example 2-1, except that a slit coating method was used to form a layer having a thickness of 10 μm.

Comparative Example 2-2

A thin film encapsulation portion sealing the organic light-emitting device on the substrate was prepared in substantially the same manner as in Example 2-1, except that an UV absorber was not used in a composition for forming an organic film.

Evaluation Example 2-1: Evaluation of Transmittance of Organic Film

Figure 5:
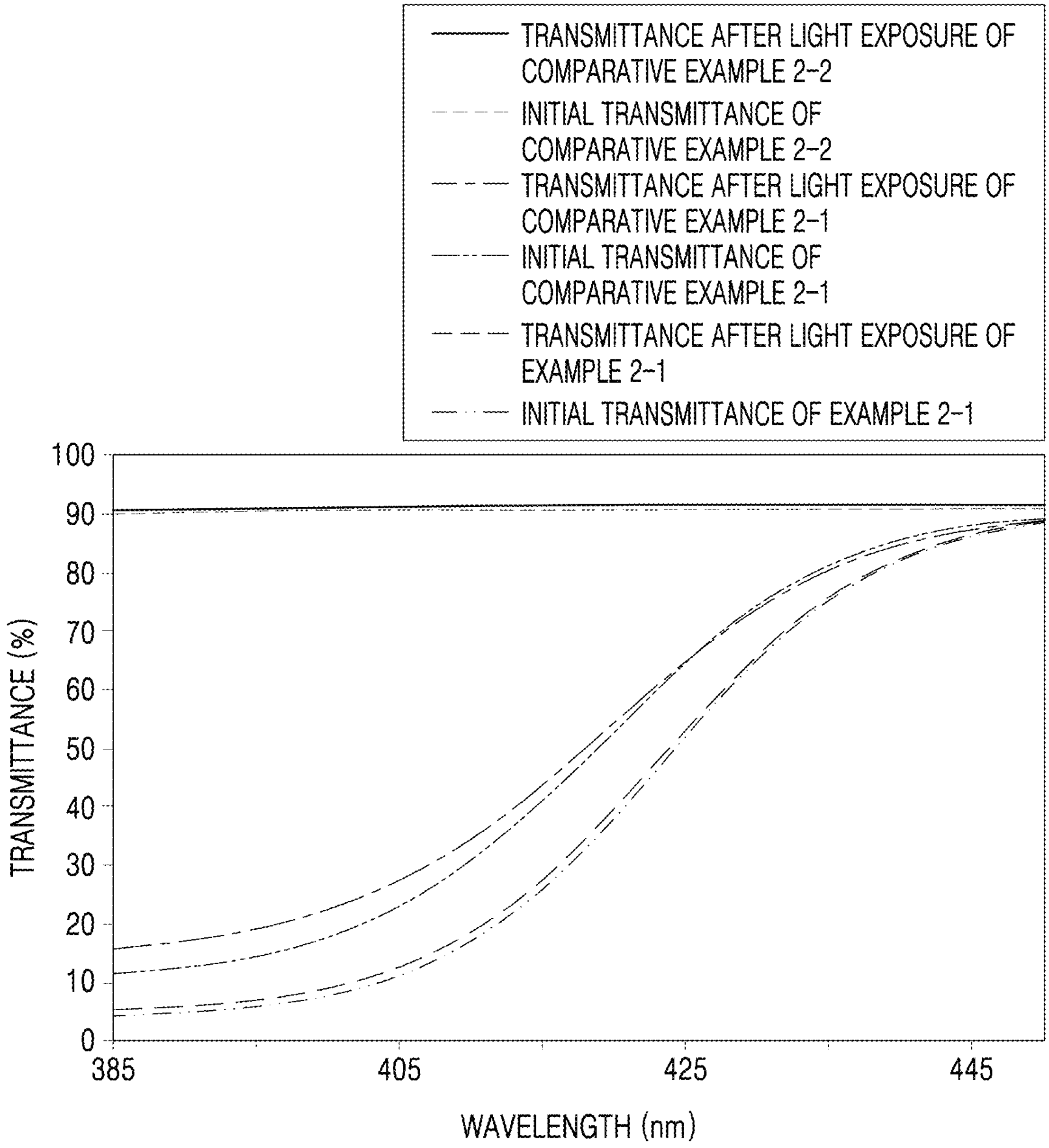
FIG. 5 is a graph showing light exposure-dependent transmittance of electronic apparatuses prepared according to Example 2-1 and Comparative Examples 2-1 and 2-2.

The initial transmittance and the post-exposure transmittance for light at an amount of about 52,000 $Wh/m^2$ for 30 minutes were each measured in the thin film encapsulation portion of the electronic apparatuses of Example 2-1 and Comparative Examples 2-1 and 2-2, and the results are shown in FIG. 5.

Referring to FIG. 5, it was confirmed that the electronic apparatus of Example 2-1 had low transmittance within a wavelength range between about 400 nm and about 430 nm, as compared with the electronic apparatuses of Comparative Examples 2-1 and 2-2, thereby efficiently blocking light having a short wavelength. In addition, the electronic apparatus of Example 2-1 maintained the transmittance of about 90% within the visible ray region.

In addition, it was confirmed that the electronic apparatus of Example 2-1 had excellent photocuring resistance based on the longer time used to increase the transmittance of the thin film encapsulation portion, compared with the electronic apparatus of Comparative Example 2-1. The change in transmittance of the thin film encapsulation portion of the electronic apparatus of each of Example 2-1 and Comparative Example 2-1 was shown in Table 3.

TABLE 3

| | Initial transmittance at 405 nm | Post-exposure transmittance at 405 nm | Change in transmittance at 405 nm (ΔT %@405 nm) |
|---|---|---|---|
| Example 2-1 | 10.95% | 12.50% | 1.5% |
| Comparative Example 2-1 | 22.75% | 27.25% | 4.5% |

Evaluation Example 2-2: Evaluation of Deterioration of Emission Layer

The composition for forming the organic film of Example 2-1 and the composition for forming the organic film of Comparative Example 2-2 were used to manufacture a FHD RGB OLED panel to which the formed organic films were each used as an organic film of the thin film encapsulation portion. To evaluate deterioration of the emission layer of the organic light-emitting device included in each OLED panel, a photolithographic exposure device (Ci3000, ATLAS) was used. The photolithographic exposure device was equipped with a xenon Arc lamp, and was configured to be able to change a temperature inside a chamber. The conditions for evaluating the deterioration of the emission layer include a xenon lamp intensity of about 0.6 $W/m^2$ at a wavelength of about 340 nm, a chamber temperature of about 40° C., and 100 hours of the light exposure time. For each OLED panel, lightening was performed thereon after light exposure, so as to measure the color temperature (Tc) and luminance (L). By comparing with initial values before light exposure, changes in the color temperature (ΔTc) and the luminance (ΔL) were derived, and the results are shown in Table 4. In addition, following the light exposure, the deterioration of the organic light-emitting device included in each OLED panel was observed with naked eyes after the panel was lightened, and the results are shown in FIG. 6.

TABLE 4

| | Example 2-1 | Comparative Example 2-2 |
|---|---|---|
| Changed amount in color temperature (ΔTc) | 30 K | 1500 K |
| Changed amount in luminance (ΔL) | 2% | −22% |

Figure 6:
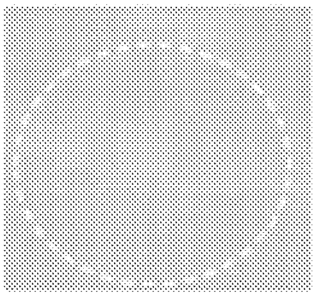
FIG. 6 is a series of images of electronic apparatuses prepared according to Example 2-1 and Comparative Example 2-2 showing deterioration of organic light-emitting devices after light exposure.
Figure 6:
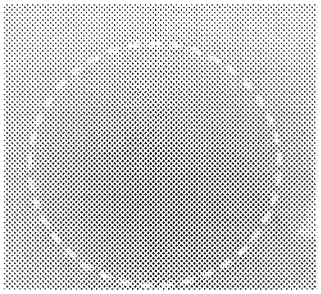

Referring to FIG. 6 and Table 4, in the case of OLED panels where the organic film formed by using the composition for forming the organic film of Example 2-1 was included in the thin film encapsulation portion, it was confirmed that the deterioration of the organic light-emitting device due to exposure to UV light was effectively prevented.

According to the one or more embodiments of the present disclosure, an electronic apparatus that is able to prevent or reduce deterioration of a light-emitting diode upon exposure to UV light associated with outgassing of a pixel defined layer or to prevent or reduce damage to an insulating layer or an emission layer including an organic material may be implemented.

It should be understood that embodiments described herein should be considered in a descriptive sense only and not for purposes of limitation. Descriptions of features or aspects within each embodiment should typically be considered as available for other similar features or aspects in other embodiments.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises," "comprising," "includes," and "including," when used in this specification, specify the presence of the stated features, integers, acts, operations, elements, and/or components, but do not preclude the presence or addition of one or more other features, integers, acts, operations, elements, components, and/or groups thereof. As used herein, the term "and/or" includes any and all combinations of one or more of the associated listed items.

As used herein, the terms "substantially," "about," and similar terms are used as terms of approximation and not as terms of degree, and are intended to account for the inherent deviations in measured or calculated values that would be recognized by those of ordinary skill in the art. Further, the use of "may" when describing embodiments of the present disclosure refers to "one or more embodiments of the present disclosure." As used herein, the terms "use," "using," and "used" may be considered synonymous with the terms "utilize," "utilizing," and "utilized," respectively. Also, the term "exemplary" is intended to refer to an example or illustration.

Also, any numerical range recited herein is intended to include all subranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more embodiments have been described with reference to the figures, it will be understood by those of ordinary skill in the art that various changes in form and details may be made therein without departing from the spirit and scope as defined by the following claims, and equivalents thereof.

What is claimed is:

1. An electronic apparatus comprising:

a substrate;

a pixel defined layer defining a plurality of pixel areas and a plurality of non-pixel areas on the substrate;

a plurality of light-emitting diodes arranged on the plurality of the pixel areas; and a thin film encapsulation portion comprising an organic film and sealing the pixel defined layer or both the plurality of the light-emitting diodes and the pixel defined layer, wherein the thin film encapsulation portion further comprises at least one inorganic film, wherein the thin film encapsulation portion comprises a sealing unit in which the organic film and the inorganic film are stacked, in the number of n, n being an integer of 1 or more, wherein the organic film comprises a cured product of a composition for forming an organic film, the composition comprising a curable material and an ultraviolet (UV) absorber, and wherein the curable material comprises a (meth)acrylate compound.

2. The electronic apparatus of claim 1, wherein the plurality of the light-emitting diodes are arranged on the substrate to be surrounded by the pixel defined layer.

3. The electronic apparatus of claim 1, wherein the inorganic film comprises at least one selected from a metal, a metal halide, a metal nitride, a metal oxide, a metal oxynitride, a silicon nitride, a silicon oxide, and a silicon oxynitride.

4. The electronic apparatus of claim 1, wherein the thin film encapsulation portion further comprises one of a lower inorganic film and a lower organic film that are disposed between the pixel defined layer and the sealing unit, or between the plurality of the light-emitting diodes and the sealing unit.

5. The electronic apparatus of claim 1, wherein at least one of a capping layer and a protection layer is further arranged between the pixel defined layer and the sealing unit, or between the plurality of the light-emitting diodes and the sealing unit.

6. The electronic apparatus of claim 1, wherein the curable material comprises at least one di(meth)acrylate compound and at least one mono(meth)acrylate compound.

7. The electronic apparatus of claim 6, wherein the di(meth)acrylate compound is represented by Formula 1; and is selected from ethylene glycol di(meth)acrylate, diethylene glycol di(meth)acrylate, triethylene glycol di(meth) acrylate, propylene glycol di(meth)acrylate, dipropylene glycol di(meth)acrylate, neopentyl glycol di(meth)acrylate, 1,4-butanediol di(meth)acrylate, 1,6-hexanediol di(meth) acrylate, bisphenol-A di(meth)acrylate, pentaerythritol di(meth)acrylate, and dipentaerythritol di(meth)acrylate:

Formula 1

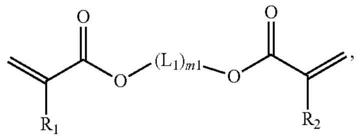

wherein, in Formula 1, $L_1$ is —O—, —S—, $S(=O)_2$—, —C(=O)—, —C(=O)O—, —C(=O)NH—, —N($R_6$)—, —C($R_6$)($R_7$)—, —Si($R_6$)($R_7$)—, or an unbranched $C_6$-$C_{20}$ alkylene group, m1 is an integer of 1 to 10, $R_1$, $R_2$, $R_6$, and $R_7$ are each independently selected from:

hydrogen, deuterium, a $C_1$-$C_{20}$ alkyl group, a $C_2$-$C_{20}$ alkenyl group, a $C_2$-$C_{20}$ alkynyl group, and a $C_1$-$C_{20}$ alkoxy group; and deuterium, —F, —Cl, —Br, —I, a hydroxyl group, a cyano group, an epoxy group, a nitro group, an amidino group, a hydrazino group, a hydrazono group, a substituted or unsubstituted $C_1$-$C_{20}$ alkyl group, and a substituted or unsubstituted $C_1$-$C_{20}$ alkoxy group.

8. The electronic apparatus of claim 6, wherein the mono(meth)acrylate compound is selected from biphenyloxy ethyl (meth)acrylate, methyl (meth)acrylate, ethyl (meth)acrylate, n-propyl (meth)acrylate, isopropyl (meth) acrylate, n-butyl (meth)acrylate, isoamyl (meth)acrylate, isobutyl (meth)acrylate, isooctyl (meth)acrylate, sec-butyl (meth)acrylate, t-butyl (meth)acrylate, n-pentyl (meth)acrylate, 3-methylbutyl (meth)acrylate, n-hexyl (meth)acrylate, 2-ethyl-n-hexyl (meth)acrylate, n-octyl (meth)acrylate, cyclohexyl (meth)acrylate, isobornyl (meth)acrylate, dicyclopentanyl (meth)acrylate, dicyclopentanyloxyethyl (meth) acrylate, isomyristyl (meth)acrylate, lauryl (meth)acrylate, methoxydipropylene glycol (meth)acrylate, methoxytripropylene glycol(meth)acrylate, benzyl(meth)acrylate, 2-hydroxyethyl (meth)acrylate, 2-hydroxypropyl (meth)acrylate, 3-hydroxypropyl (meth)acrylate, 4-hydroxybutyl (meth) acrylate, 5-hydroxypentyl (meth)acrylate, 6-hydroxyhexyl (meth)acrylate, 4-hydroxycyclohexyl (meth)acrylate, neopentylglycol mono(meth)acrylate, 3-chloro-2-hydroxypropyl (meth)acrylate, (1,1-dimethyl-3-oxobutyl) (meth)acrylate, 2-acetoacetoxyethyl (meth)acrylate, 2-methoxyethyl (meth)acrylate, 2-ethoxyethyl (meth)acrylate, neopentylglycol mono(meth)acrylate, ethylene glycol monomethyl ether (meth)acrylate, glycerin mono(meth)acrylate, 2-acryloyloxyethyl phthalate, 2-acryloyloxy 2-hydroxyethyl phthalate, 2-acryloyloxyethyl hexahydrophthalate, 2-acryloyloxy propylphthalate, neopentylglycolbenzoate (meth)acrylate, nonylphenoxypolyethylene glycol (meth)acrylate, nonylphenoxypolypropylene glycol (meth)acrylate, paracumylphenoxyethylene glycol (meth)acrylate, ECH modified phenoxy acrylate, phenoxyethyl (meth)acrylate, phenoxydiethylene glycol (meth)acrylate, phenoxyhexaethylene glycol (meth)acrylate, phenoxytetraethylene glycol (meth)acrylate, polyethylene glycol (meth)acrylate, polyethylene glycol phenylether (meth)acrylate, polyethylene glycol-polypropylene glycol (meth)acrylate, polypropylene glycol (meth) acrylate, stearyl (meth)acrylate, ethoxylated phenol acrylate (Phenol (EO) acrylate), ethoxylated cresol (meth)acrylate, dipropylene glycol (meth)acrylate, ethoxylated phenyl (meth)acrylate, ethoxylated succinate (meth)acrylate, tert-butyl (meth)acrylate, tribromophenyl (meth)acrylate, ethoxylated tribromophenyl (meth)acrylate, tridodecyl (meth)acrylate, and tetrahydrofurfuryl (meth)acrylate.

9. The electronic apparatus of claim 1, wherein the UV absorber comprises an UV-absorbing compound, wherein the UV-absorbing compound comprises at least one UV absorbing unit represented by one selected from Formulae 1-1 to 1-4:

Formula 1-1

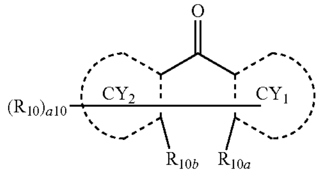

Formula 1-2

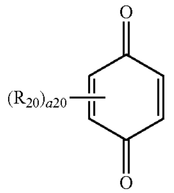

Formula 1-3

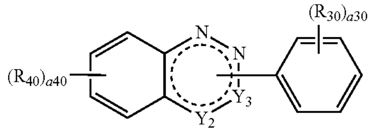

Formula 1-4

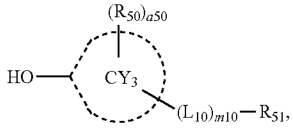

wherein, in Formulae 1-1 to 1-4, $CY_1$ to $CY_3$ are each independently selected from a benzene group, a naphthalene group, an anthracene group, a pyrene group, and a phenanthrene group, $L_{10}$ is —O—, —S—, $S(=O)_2$—, —C(=O)—, —C(=O)O—, —C(=O)NH—, a $C_1$-$C_{30}$ hydrocarbon group, a $C_5$-$C_{60}$ carbocyclic group, or a $C_2$-$C_{30}$ heterocyclic group, m10 is an integer of 0 to 5, wherein $L_{10}$ is a single bond when m10 is 0, $R_{10a}$ and $R_{10b}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, $—N(Q_1)(Q_2)$, $—B(Q_1)(Q_2)$, $—C(=O)(Q_1)$, $—S(=O)_2(Q_1)$, and $—P(=O)(Q_1)(Q_2)$, $R_{10a}$ and $R_{10b}$ are optionally linked to form a $—(Y_1)_{k1}—$ linking group, $Y_1$ is —O—, —S—, or, —C(=O)—, k1 is an integer of 1 to 3, one of $Y_2$ and $Y_3$ is nitrogen (N), and the other one is a single bond, a double bond, or —C(=O)—, $R_{10}$, $R_{20}$, $R_{30}$, $R_{40}$, $R_{50}$, and $R_{51}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cyclo alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, $Si(Q_1)(Q_2)(Q_3)$, $—N(Q_1)(Q_2)$, $—B(Q_1)(Q_2)$, $—C(=O)(Q_1)$, $—S(=O)_2(Q_1)$, and $—P(=O)(Q_1)(Q_2)$, a10 is an integer of 1 to 8, a20 and a40 are each an integer of 1 to 4, a30 is an integer of 1 to 5, a50 is an integer of 1 to 10, at least one of $R_{10}$(s) in the number of a10 is a hydroxyl group, at least one of $R_{20}$(s) in the number of a20 is a hydroxyl group, at least one of $R_{30}$(s) in the number of a30 is a hydroxyl group, and $Q_1$ to $Q_3$ are each independently selected from hydrogen, deuterium, a hydroxyl group, a $C_1$-$C_{60}$ alkyl group, a $C_2$-$C_{60}$ alkenyl group, a $C_2$-$C_{60}$ alkynyl group, a $C_1$-$C_{60}$ alkoxy group, and a $C_6$-$C_{60}$ aryl group.

10. The electronic apparatus of claim 9, wherein the UV-absorbing unit is represented by one selected from Formulae 2-1 to 2-11:

2-1

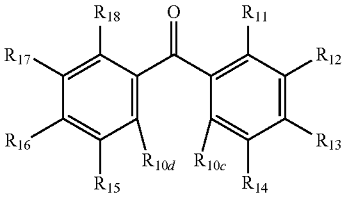

2-2

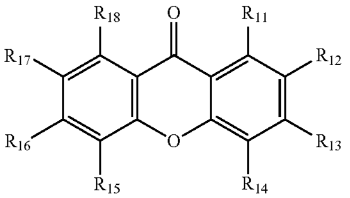

2-3

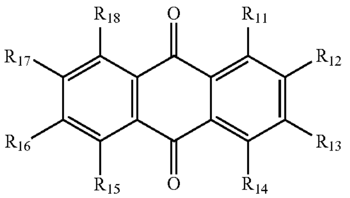

2-4

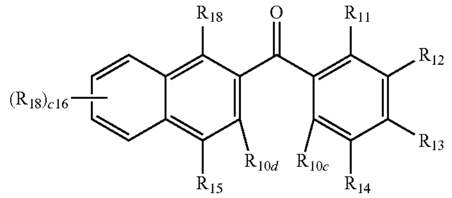

2-5

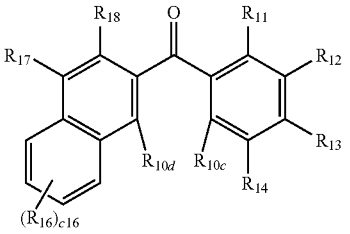

2-6

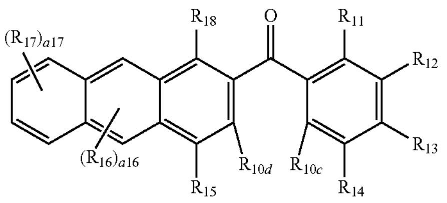

2-7

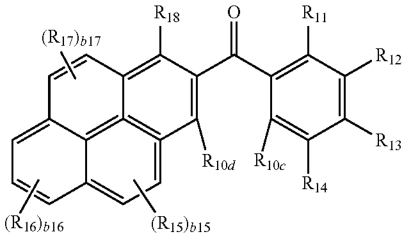

-continued 2-8

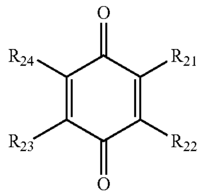

2-9

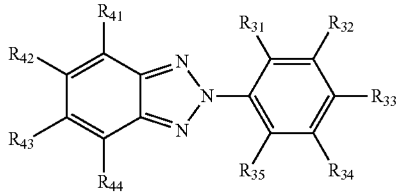

2-10

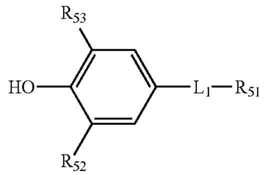

2-11

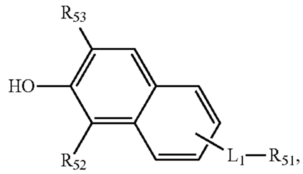

wherein, in Formulae 2-1 to 2-11, $L_1$ is defined the same as $L_{10}$ of claim 9, $R_{10c}$, $R_{10d}$, and $R_{11}$ to $R_{18}$ are respectively defined the same as $R_{10}$ of claim 9, a16 is 1 or 2, a17 is 1, 2, 3, or 4, b15 is 1 or 2, b16 is 1, 2, or 3, b17 is 1 or 2, c16 is 1, 2, 3, or 4, $R_{21}$ to $R_{24}$ are respectively defined the same as $R_{20}$ of claim 9, $R_{31}$ to $R_{35}$ are respectively defined the same as $R_{30}$ of claim 9, $R_{41}$ to $R_{44}$ are respectively defined the same as $R_{40}$ of claim 9, $R_{51}$ to $R_{53}$ are respectively defined the same as $R_{50}$ of claim 9, at least one selected from $R_{11}$ to $R_{18}$, at least one selected from $R_{21}$ to $R_{24}$, and at least one selected from $R_{31}$ to $R_{35}$ are each a hydroxyl group, and

* indicates a binding site to a neighboring atom.

11. The electronic apparatus of claim 1, wherein the UV absorber comprises a first UV-absorbing compound and a second UV-absorbing compound, and a wavelength range of light absorbed by the first UV-absorbing compound is different from that of light absorbed by the second UV-absorbing compound.

12. The electronic apparatus of claim 1, wherein an amount of the UV absorber is in a range of about 0.5 parts to about 5 parts by weight based on 100 parts by weight of the composition for forming the organic film.

13. The electronic apparatus of claim 1, wherein the organic film has a change in transmittance of less than about 1% within a wavelength range between about 380 nm to about 400 nm, when exposed at an exposure amount of 52,000 $Wh/m^2$.

14. An electronic apparatus comprising:

a substrate;

an organic light-emitting device disposed on the substrate and comprising an emission layer; and a thin film encapsulation portion sealing the organic light-emitting device and comprising at least one organic film, wherein the thin film encapsulation portion further comprises at least one inorganic film, wherein the thin film encapsulation portion comprises a sealing unit in which the organic film and the inorganic film are stacked, in the number of n, n being an integer of 1 or more, wherein the emission layer comprises an organometallic compound, and the organic film comprises a cured product of a composition for forming an organic film, the composition comprising a curable material and an ultraviolet (UV) absorber, and wherein the curable material comprises a (meth)acrylate compound.

15. The electronic apparatus of claim 14, wherein the organometallic compound comprises a compound represented by Formula 401:

$$M(L_{401})_{xc1}(L_{402})_{xc2}$$ Formula 401

Formula 402

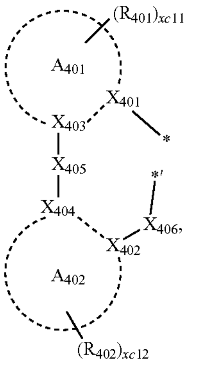

wherein, in Formulae 401 and 402,

M is selected from iridium (Ir), platinum (Pt), palladium (Pd), osmium (Os), titanium (Ti), zirconium (Zr), hafnium (Hf), europium (Eu), terbium (Tb), rhodium (Rh), and thulium (Tm), $L_{401}$ is a ligand represented by Formula 402, xc1 is 1, 2, or 3, and when xc1 is two or more, two or more of $L_{401}$(s) are identical to or different from each other, $L_{402}$ is an organic ligand, xc2 is an integer of 0 to 4, and when xc2 is two or more, two or more of $L_{402}$(s) are identical to or different from each other, $X_{401}$ to $X_{404}$ are each independently nitrogen or carbon, $X_{401}$ and $X_{403}$ are linked via a single bond or a double bond, $X_{402}$ and $X_{404}$ are linked via a single bond or a double bond, $A_{401}$ and $A_{402}$ are each independently a $C_5$-$C_{60}$ carbocyclic group or a $C_1$-$C_{60}$ heterocyclic group, $X_{405}$ is a single bond, *—O—*', *—S—*I, *—C(=O)—*', *—N($Q_{411}$)-*', *—C($Q_{411}$)($Q_{412}$)-*', *—C($Q_{411}$)=C($Q_{412}$)-*', *—C($Q_{411}$)=*', or *=C($Q_{411}$)=*', wherein $Q_{411}$ and $Q_{412}$ are each independently hydrogen, deuterium, a $C_1$-$C_{20}$ alkyl group, a $C_1$-$C_{20}$ alkoxy group, a phenyl group, a biphenyl group, a terphenyl group, or a naphthyl group, $X_{406}$ is a single bond, O, or S, $R_{401}$ and $R_{402}$ are each independently selected from hydrogen, deuterium, —F, —Cl, —Br, —I, a hydroxyl group, a cyano group, a nitro group, an amidino group, a hydrazino group, a hydrazono group, a substituted or unsubstituted $C_1$-$C_{20}$ alkyl group, a substituted or unsubstituted $C_1$-$C_{20}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, —Si($Q_{401}$)($Q_{402}$)($Q_{403}$), —N($Q_{401}$)($Q_{402}$), —B($Q_{401}$)($Q_{402}$), —C(=O)($Q_{401}$), —S(=O)$_2$($Q_{401}$), and —P(=O)($Q_{401}$)($Q_{402}$), wherein $Q_{401}$ to $Q_{403}$ are each independently selected from a $C_1$-$C_{10}$ alkyl group, a $C_1$-$C_{10}$ alkoxy group, a $C_6$-$C_{20}$ aryl group, and a $C_1$-$C_{20}$ heteroaryl group, xc11 and xc12 are each independently an integer of 0 to 10, and

* and *' in Formula 402 each indicate a binding site to M of Formula 401.

16. The electronic apparatus of claim 14, wherein the emission layer emits red phosphorescence having a maximum emission wavelength between the 590 nm and 780 nm.

17. An electronic apparatus comprising:

a substrate;

a pixel defined layer defining a plurality of pixel areas and a plurality of non-pixel areas on the substrate;

a plurality of light-emitting diodes arranged on the plurality of the pixel areas; and a thin film encapsulation portion comprising an organic film and sealing the pixel defined layer or both the plurality of the light-emitting diodes and the pixel defined layer, wherein the thin film encapsulation portion further comprises at least one inorganic film, wherein the thin film encapsulation portion comprises a sealing unit in which the organic film and the inorganic film are stacked, in the number of n, n being an integer of 1 or more, and wherein the organic film comprises a cured product of a composition for forming an organic film, the composition comprising at least one UV absorber.

18. The electronic apparatus of claim 17, wherein:

the plurality of light-emitting diodes comprises at least one emission layer comprising an inorganic material, the inorganic material is a quantum confined semiconductor nanoparticle selected from compounds of Groups II-VI, compounds of Groups III-V, and compounds of Groups IV-VI, compounds of Group IV, compounds of Group IV, and any combination thereof, and an alloy of thereof.

19. The electronic apparatus of claim 17, wherein the inorganic material be a perovskite compound represented by Formula 3:

$$[A][B][X]_3, \quad \text{Formula 3}$$

wherein, in Formula 3,

A is at least one monovalent organic-cation, at least one inorganic-cation, or any combination thereof, B is at least one divalent inorganic-cation, and X is at least one monovalent cation.

* * * * *